(12) United States Patent
Parker et al.

(10) Patent No.: US 11,944,820 B2
(45) Date of Patent: Apr. 2, 2024

(54) NEUROSTIMULATION OF MIXED NERVES

(71) Applicant: Saluda Medical Pty Ltd, Artarmon (AU)

(72) Inventors: John Louis Parker, Artarmon (AU); Gerrit Eduard Gmel, Artarmon (AU)

(73) Assignee: Saluda Medical Pty Ltd, Artarmon (AU)

(*) Notice: Subject to any disclaimer, the term of this patent is extended or adjusted under 35 U.S.C. 154(b) by 623 days.

(21) Appl. No.: 17/050,788

(22) PCT Filed: Apr. 29, 2019

(86) PCT No.: PCT/AU2019/050384
§ 371 (c)(1),
(2) Date: Oct. 26, 2020

(87) PCT Pub. No.: WO2019/204884
PCT Pub. Date: Oct. 31, 2019

(65) Prior Publication Data
US 2021/0121696 A1 Apr. 29, 2021

(30) Foreign Application Priority Data
Apr. 27, 2018 (AU) ................ 2018901410

(51) Int. Cl.
A61N 1/36 (2006.01)
A61N 1/05 (2006.01)
G16H 20/40 (2018.01)

(52) U.S. Cl.
CPC ....... *A61N 1/36139* (2013.01); *A61N 1/0553* (2013.01); *A61N 1/0556* (2013.01);
(Continued)

(58) Field of Classification Search
CPC .............. A61N 1/36139; A61N 1/0553; A61N 1/0556; A61N 1/36003
See application file for complete search history.

(56) References Cited

U.S. PATENT DOCUMENTS 3,724,467 A 4/1973 Avery et al.
3,736,434 A 5/1973 Darrow
(Continued)

FOREIGN PATENT DOCUMENTS

AU 2013277009 B2 1/2016
CN 103648583 A 3/2014
(Continued)

OTHER PUBLICATIONS

"Percutaneous Lead Kit", St. Jude Medical Clinician's Manual, Models 3143, 3146, 3149, 3153, 3156, 3159, 3183, 3186, 3189, published Sep. 2016, 24 pages.
(Continued)

Primary Examiner — Amanda K Hulbert
Assistant Examiner — Philip C Edwards
(74) Attorney, Agent, or Firm — Barnes & Thornburg LLP

(57) ABSTRACT

Neurostimulation of a mixed nerve comprising a plurality of nerve fibre types. An implantable electrode array comprising a plurality of electrodes is positioned proximal to the mixed nerve. An electrical stimulus is delivered from at least one nominal stimulus electrode of the implantable electrode array, in accordance with a set of stimulus parameters. A recording of the electrophysiological response evoked by the electrical stimulus is obtained from at least one nominal recording electrode of the implantable electrode array. The recording is analysed by assessing one or more selected characteristics of the recording, and from the observed selected characteristics a level of recruitment of one or more fibre types recruited by the electrical stimulus is identified. The stimulus parameters are refined in a manner to effect selective recruitment of one or more fibre types relative to other fibre types of the mixed nerve.

37 Claims, 13 Drawing Sheets

(52) U.S. Cl.
CPC ..... *A61N 1/36003* (2013.01); *A61N 1/36007* (2013.01); *A61N 1/3601* (2013.01); *A61N 1/36064* (2013.01); *A61N 1/36071* (2013.01); *A61N 1/36096* (2013.01); *A61N 1/36114* (2013.01); *A61N 1/36157* (2013.01); *A61N 1/36171* (2013.01); *A61N 1/36175* (2013.01); *G16H 20/40* (2018.01)

(56) References Cited

U.S. PATENT DOCUMENTS

| | | |
|---|---|---|
| 3,817,254 A | 6/1974 | Maurer |
| 3,898,472 A | 8/1975 | Long |
| 4,158,196 A | 6/1979 | Crawford, Jr. |
| 4,418,695 A | 12/1983 | Buffet |
| 4,474,186 A | 10/1984 | Ledley et al. |
| 4,628,934 A | 12/1986 | Pohndorf et al. |
| 4,807,643 A | 2/1989 | Rosier |
| 4,856,525 A | 8/1989 | van den Honert |
| 5,113,859 A | 5/1992 | Funke |
| 5,139,020 A | 8/1992 | Koestner et al. |
| 5,143,081 A | 9/1992 | Young et al. |
| 5,156,154 A | 10/1992 | Valenta, Jr. et al. |
| 5,172,690 A | 12/1992 | Nappholz et al. |
| 5,184,615 A | 2/1993 | Nappholz et al. |
| 5,188,106 A | 2/1993 | Nappholz et al. |
| 5,215,100 A | 6/1993 | Spitz |
| 5,324,311 A | 6/1994 | Acken |
| 5,417,719 A | 5/1995 | Hull et al. |
| 5,431,693 A | 7/1995 | Schroeppel |
| 5,458,623 A | 10/1995 | Lu et al. |
| 5,476,486 A | 12/1995 | Lu et al. |
| 5,497,781 A | 3/1996 | Chen et al. |
| 5,638,825 A | 6/1997 | Yamazaki et al. |
| 5,702,429 A | 12/1997 | King et al. |
| 5,758,651 A | 6/1998 | Nygard et al. |
| 5,776,170 A | 7/1998 | Macdonald et al. |
| 5,785,651 A | 7/1998 | Kuhn et al. |
| 5,792,212 A | 8/1998 | Weijand et al. |
| 5,814,092 A | 9/1998 | King |
| 5,895,416 A | 4/1999 | Barreras et al. |
| 5,913,882 A | 6/1999 | King |
| 5,999,848 A | 12/1999 | Gord et al. |
| 6,020,857 A | 2/2000 | Podger |
| 6,027,456 A | 2/2000 | Feler et al. |
| 6,038,480 A | 3/2000 | Hrdlicka et al. |
| 6,066,163 A | 5/2000 | John |
| 6,114,164 A | 9/2000 | Dennis et al. |
| 6,144,881 A | 11/2000 | Hemming et al. |
| 6,157,861 A | 12/2000 | Faltys et al. |
| 6,212,431 B1 | 4/2001 | Hahn et al. |
| 6,246,912 B1 | 6/2001 | Sluijter et al. |
| 6,381,496 B1 | 4/2002 | Meadows et al. |
| 6,449,512 B1 | 9/2002 | Boveja |
| 6,463,328 B1 | 10/2002 | John |
| 6,473,649 B1 | 10/2002 | Gryzwa et al. |
| 6,473,653 B1 | 10/2002 | Schallhorn et al. |
| 6,493,576 B1 | 12/2002 | Dankwart-Eder |
| 6,516,227 B1 | 2/2003 | Meadows et al. |
| 6,522,932 B1 | 2/2003 | Kuzma |
| 6,600,955 B1 | 7/2003 | Zierhofer et al. |
| 6,658,293 B2 | 12/2003 | Vonk et al. |
| 6,675,046 B2 | 1/2004 | Holsheimer |
| 6,782,292 B2 | 8/2004 | Whitehurst |
| 6,895,280 B2 | 5/2005 | Meadows et al. |
| 6,898,582 B2 | 5/2005 | Lange et al. |
| 6,909,917 B2 | 6/2005 | Woods et al. |
| 7,089,059 B1 | 8/2006 | Pless |
| 7,171,261 B1 | 1/2007 | Litvak et al. |
| 7,177,675 B2 | 2/2007 | Suffin et al. |
| 7,206,640 B1 | 4/2007 | Overstreet |
| 7,231,254 B2 | 6/2007 | DiLorenzo et al. |
| 7,286,876 B2 | 10/2007 | Yonce et al. |
| 7,412,287 B2 | 8/2008 | Yonce et al. |
| 7,450,992 B1 | 11/2008 | Cameron |
| 7,634,315 B2 | 12/2009 | Cholette |
| 7,734,340 B2 | 6/2010 | De Ridder |
| 7,742,810 B2 | 6/2010 | Moffitt |
| 7,792,584 B2 | 9/2010 | Van et al. |
| 7,818,052 B2 | 10/2010 | Litvak et al. |
| 7,831,305 B2 | 11/2010 | Gliner |
| 7,835,804 B2 | 11/2010 | Fridman et al. |
| 7,890,182 B2 | 2/2011 | Parramon et al. |
| 7,894,905 B2 | 2/2011 | Pless et al. |
| 8,083,685 B2 | 12/2011 | Fagin et al. |
| 8,190,251 B2 | 5/2012 | Molnar et al. |
| 8,224,459 B1 | 7/2012 | Pianca et al. |
| 8,239,031 B2 | 8/2012 | Fried et al. |
| 8,249,698 B2 | 8/2012 | Mugler et al. |
| 8,332,047 B2 | 12/2012 | Libbus et al. |
| 8,359,102 B2 | 1/2013 | Thacker et al. |
| 8,401,655 B2 | 3/2013 | De Ridder |
| 8,417,342 B1 | 4/2013 | Abell |
| 8,454,529 B2 | 6/2013 | Daly et al. |
| 8,494,645 B2 | 7/2013 | Spitzer et al. |
| 8,515,545 B2 | 8/2013 | Trier |
| 8,588,929 B2 | 11/2013 | Davis et al. |
| 8,670,830 B2 | 3/2014 | Carlson et al. |
| 8,886,323 B2 | 11/2014 | Wu et al. |
| 9,044,155 B2 | 6/2015 | Strahl |
| 9,155,892 B2 | 10/2015 | Parker et al. |
| 9,302,112 B2 | 4/2016 | Bornzin et al. |
| 9,381,356 B2 | 7/2016 | Parker et al. |
| 9,386,934 B2 | 7/2016 | Parker et al. |
| 9,872,990 B2 | 1/2018 | Parker et al. |
| 9,974,455 B2 | 5/2018 | Parker et al. |
| 10,206,596 B2 | 2/2019 | Single et al. |
| 10,278,600 B2 | 5/2019 | Parker et al. |
| 10,368,762 B2 | 8/2019 | Single |
| 10,426,409 B2 | 10/2019 | Single |
| 10,500,399 B2 | 12/2019 | Single |
| 10,568,559 B2 | 2/2020 | Parker et al. |
| 10,588,524 B2 | 3/2020 | Single et al. |
| 10,588,698 B2 | 3/2020 | Parker et al. |
| 10,632,307 B2 | 4/2020 | Parker |
| 10,842,996 B2 | 11/2020 | Baru et al. |
| 10,849,525 B2 | 12/2020 | Parker et al. |
| 10,894,158 B2 | 1/2021 | Parker |
| 10,918,872 B2 | 2/2021 | Parker et al. |
| 11,006,846 B2 | 5/2021 | Parker et al. |
| 11,006,857 B2 | 5/2021 | Parker |
| 11,045,129 B2 | 6/2021 | Parker et al. |
| 11,110,270 B2 | 9/2021 | Parker et al. |
| 11,167,129 B2 | 11/2021 | Parker |
| 11,172,864 B2 | 11/2021 | Parker et al. |
| 11,179,091 B2 | 11/2021 | Karantonis et al. |
| 11,191,966 B2 | 12/2021 | Wah |
| 2002/0055688 A1 | 5/2002 | Katims |
| 2002/0099419 A1 | 7/2002 | Ayal et al. |
| 2002/0193670 A1 | 12/2002 | Garfield et al. |
| 2003/0032889 A1 | 2/2003 | Wells |
| 2003/0045909 A1 | 3/2003 | Gross et al. |
| 2003/0139781 A1 | 7/2003 | Bradley et al. |
| 2003/0153959 A1 | 8/2003 | Thacker et al. |
| 2003/0195580 A1 | 10/2003 | Bradley et al. |
| 2004/0088017 A1 | 5/2004 | Sharma et al. |
| 2004/0116978 A1 | 6/2004 | Bradley |
| 2004/0122482 A1 | 6/2004 | Tung et al. |
| 2004/0158298 A1 | 8/2004 | Gliner |
| 2004/0225211 A1 | 11/2004 | Gozani et al. |
| 2004/0254494 A1 | 12/2004 | Spokoyny et al. |
| 2005/0010265 A1 | 1/2005 | Baru Fassio |
| 2005/0017190 A1 | 1/2005 | Eversmann et al. |
| 2005/0021104 A1 | 1/2005 | DiLorenzo |
| 2005/0065427 A1 | 3/2005 | Magill |
| 2005/0070982 A1 | 3/2005 | Heruth et al. |
| 2005/0075683 A1 | 4/2005 | Miesel et al. |
| 2005/0101878 A1 | 5/2005 | Daly et al. |
| 2005/0107674 A1 | 5/2005 | Parthasarathy et al. |
| 2005/0113877 A1 | 5/2005 | Giardiello et al. |
| 2005/0137670 A1 | 6/2005 | Christopherson et al. |
| 2005/0149154 A1 | 7/2005 | Cohen |
| 2005/0192567 A1 | 9/2005 | Katims |
| 2005/0203600 A1 | 9/2005 | Wallace |

(56) References Cited

U.S. PATENT DOCUMENTS

| | | |
|---|---|---|
| 2005/0209655 A1 | 9/2005 | Bradley et al. |
| 2005/0216064 A1 | 9/2005 | Heruth et al. |
| 2005/0282149 A1 | 12/2005 | Kovacs et al. |
| 2006/0009820 A1 | 1/2006 | Royle et al. |
| 2006/0020291 A1 | 1/2006 | Gozani |
| 2006/0129205 A1 | 6/2006 | Boveja et al. |
| 2006/0135998 A1 | 6/2006 | Libbus et al. |
| 2006/0195159 A1 | 8/2006 | Bradley et al. |
| 2006/0212089 A1 | 9/2006 | Tass |
| 2006/0217782 A1 | 9/2006 | Boveja et al. |
| 2006/0264752 A1 | 11/2006 | Rubinsky et al. |
| 2006/0276722 A1 | 12/2006 | Litvak et al. |
| 2006/0287609 A1 | 12/2006 | Litvak et al. |
| 2007/0021800 A1 | 1/2007 | Bradley et al. |
| 2007/0073354 A1 | 3/2007 | Knudson et al. |
| 2007/0100378 A1 | 5/2007 | Maschino |
| 2007/0178579 A1 | 8/2007 | Ross et al. |
| 2007/0185409 A1 | 8/2007 | Wu et al. |
| 2007/0208394 A1 | 9/2007 | King et al. |
| 2007/0225765 A1 | 9/2007 | King |
| 2007/0225767 A1 | 9/2007 | Daly et al. |
| 2007/0244410 A1 | 10/2007 | Fridman et al. |
| 2007/0250120 A1 | 10/2007 | Flach et al. |
| 2007/0255372 A1 | 11/2007 | Metzler et al. |
| 2007/0265489 A1 | 11/2007 | Borgerding et al. |
| 2007/0282217 A1 | 12/2007 | McGinnis et al. |
| 2007/0287931 A1 | 12/2007 | Dilorenzo |
| 2008/0021292 A1 | 1/2008 | Stypulkowski |
| 2008/0051647 A1 | 2/2008 | Wu et al. |
| 2008/0064947 A1 | 3/2008 | Heruth et al. |
| 2008/0077191 A1 | 3/2008 | Morrell |
| 2008/0097529 A1 | 4/2008 | Parramon et al. |
| 2008/0132964 A1 | 6/2008 | Cohen et al. |
| 2008/0147155 A1 | 6/2008 | Swoyer |
| 2008/0183076 A1 | 7/2008 | Witte et al. |
| 2008/0208304 A1 | 8/2008 | Zdravkovic et al. |
| 2008/0234780 A1 | 9/2008 | Smith et al. |
| 2008/0275527 A1 | 11/2008 | Greenberg et al. |
| 2008/0294221 A1 | 11/2008 | Kilgore |
| 2008/0300655 A1 | 12/2008 | Cholette |
| 2008/0319508 A1 | 12/2008 | Botros et al. |
| 2009/0030337 A1 | 1/2009 | Gozani et al. |
| 2009/0033486 A1 | 2/2009 | Costantino et al. |
| 2009/0058635 A1 | 3/2009 | Lalonde et al. |
| 2009/0082691 A1 | 3/2009 | Denison et al. |
| 2009/0149912 A1 | 6/2009 | Dacey, Jr. et al. |
| 2009/0157155 A1 | 6/2009 | Bradley |
| 2009/0270957 A1 | 10/2009 | Pianca |
| 2009/0281594 A1 | 11/2009 | Wacnik et al. |
| 2009/0287277 A1 | 11/2009 | Conn et al. |
| 2009/0299214 A1 | 12/2009 | Wu et al. |
| 2009/0306491 A1 | 12/2009 | Haggers |
| 2009/0306533 A1 | 12/2009 | Rousche et al. |
| 2010/0010388 A1 | 1/2010 | Panken et al. |
| 2010/0057159 A1 | 3/2010 | Lozano |
| 2010/0058126 A1 | 3/2010 | Chang et al. |
| 2010/0069835 A1 | 3/2010 | Parker |
| 2010/0069996 A1 | 3/2010 | Strahl |
| 2010/0070007 A1 | 3/2010 | Parker |
| 2010/0070008 A1 | 3/2010 | Parker |
| 2010/0100153 A1 | 4/2010 | Carlson et al. |
| 2010/0106231 A1 | 4/2010 | Torgerson |
| 2010/0114237 A1 | 5/2010 | Giftakis et al. |
| 2010/0114258 A1 | 5/2010 | Donofrio et al. |
| 2010/0125313 A1 | 5/2010 | Lee et al. |
| 2010/0125314 A1 | 5/2010 | Bradley et al. |
| 2010/0145222 A1 | 6/2010 | Brunnett et al. |
| 2010/0152808 A1 | 6/2010 | Boggs |
| 2010/0179626 A1 | 7/2010 | Pilarski |
| 2010/0191307 A1 | 7/2010 | Fang et al. |
| 2010/0204748 A1 | 8/2010 | Lozano et al. |
| 2010/0222844 A1 | 9/2010 | Troosters et al. |
| 2010/0222858 A1 | 9/2010 | Meloy |
| 2010/0249643 A1 | 9/2010 | Gozani et al. |
| 2010/0249867 A1 | 9/2010 | Wanasek |
| 2010/0258342 A1 | 10/2010 | Parker |
| 2010/0262208 A1 | 10/2010 | Parker |
| 2010/0262214 A1 | 10/2010 | Robinson |
| 2010/0280570 A1 | 11/2010 | Sturm et al. |
| 2010/0286748 A1 | 11/2010 | Midani et al. |
| 2010/0331604 A1 | 12/2010 | Okamoto et al. |
| 2010/0331926 A1 | 12/2010 | Lee et al. |
| 2011/0004207 A1 | 1/2011 | Wallace et al. |
| 2011/0021943 A1 | 1/2011 | Lacour et al. |
| 2011/0028859 A1 | 2/2011 | Chian |
| 2011/0040546 A1 | 2/2011 | Gerber et al. |
| 2011/0077712 A1 | 3/2011 | Killian |
| 2011/0087085 A1 | 4/2011 | Tsampazis et al. |
| 2011/0093042 A1 | 4/2011 | Torgerson et al. |
| 2011/0106100 A1 | 5/2011 | Bischoff |
| 2011/0130802 A1 | 6/2011 | Libbus et al. |
| 2011/0184488 A1 | 7/2011 | De Ridder et al. |
| 2011/0204811 A1 | 8/2011 | Pollmann-retsch |
| 2011/0224665 A1 | 9/2011 | Crosby et al. |
| 2011/0224749 A1 | 9/2011 | Ben-David et al. |
| 2011/0264165 A1 | 10/2011 | Molnar et al. |
| 2011/0270343 A1 | 11/2011 | Buschman et al. |
| 2011/0288391 A1 | 11/2011 | Rao et al. |
| 2011/0307030 A1 | 12/2011 | John |
| 2011/0313310 A1 | 12/2011 | Tomita |
| 2011/0313483 A1 | 12/2011 | Hincapie et al. |
| 2012/0029377 A1 | 2/2012 | Polak |
| 2012/0059275 A1 | 3/2012 | Fagin et al. |
| 2012/0101552 A1 | 4/2012 | Lazarewicz et al. |
| 2012/0101826 A1 | 4/2012 | Visser et al. |
| 2012/0109004 A1 | 5/2012 | Cadwell |
| 2012/0109236 A1 | 5/2012 | Jacobson et al. |
| 2012/0155183 A1 | 6/2012 | Aritome |
| 2012/0185020 A1 | 7/2012 | Simon et al. |
| 2012/0245481 A1 | 9/2012 | Blanco et al. |
| 2012/0253423 A1 | 10/2012 | Youn et al. |
| 2012/0277621 A1 | 11/2012 | Gerber et al. |
| 2012/0277823 A1 | 11/2012 | Gerber et al. |
| 2012/0310301 A1 | 12/2012 | Bennett et al. |
| 2013/0041449 A1 | 2/2013 | Cela et al. |
| 2013/0053722 A1 | 2/2013 | Carlson et al. |
| 2013/0060302 A1 | 3/2013 | Polefko et al. |
| 2013/0172774 A1 | 7/2013 | Crowder et al. |
| 2013/0289661 A1 | 10/2013 | Griffith et al. |
| 2013/0289683 A1 | 10/2013 | Parker et al. |
| 2014/0046407 A1 | 2/2014 | Ben-ezra et al. |
| 2014/0066803 A1 | 3/2014 | Choi |
| 2014/0142447 A1 | 5/2014 | Takahashi et al. |
| 2014/0194771 A1 | 7/2014 | Parker et al. |
| 2014/0194772 A1 | 7/2014 | Single et al. |
| 2014/0236042 A1 | 8/2014 | Parker et al. |
| 2014/0236257 A1 | 8/2014 | Parker et al. |
| 2014/0243926 A1 | 8/2014 | Carcieri |
| 2014/0243931 A1 | 8/2014 | Parker et al. |
| 2014/0249396 A1 | 9/2014 | Shacham-diamand et al. |
| 2014/0276195 A1 | 9/2014 | Papay et al. |
| 2014/0277250 A1 | 9/2014 | Su et al. |
| 2014/0277267 A1 | 9/2014 | Vansickle et al. |
| 2014/0288551 A1 | 9/2014 | Bharmi et al. |
| 2014/0288577 A1 | 9/2014 | Robinson et al. |
| 2014/0296737 A1 | 10/2014 | Parker et al. |
| 2014/0324118 A1 | 10/2014 | Simon et al. |
| 2014/0350634 A1 | 11/2014 | Grill et al. |
| 2014/0358024 A1 | 12/2014 | Nelson et al. |
| 2015/0018699 A1 | 1/2015 | Zeng et al. |
| 2015/0025597 A1 | 1/2015 | Surth et al. |
| 2015/0032181 A1 | 1/2015 | Baynham et al. |
| 2015/0051637 A1 | 2/2015 | Osorio |
| 2015/0126839 A1 | 5/2015 | Li et al. |
| 2015/0148869 A1 | 5/2015 | Dorvall, II et al. |
| 2015/0164354 A1 | 6/2015 | Parker et al. |
| 2015/0174396 A1 | 6/2015 | Fisher et al. |
| 2015/0238104 A1 | 8/2015 | Tass |
| 2015/0238304 A1 | 8/2015 | Lamraoui |
| 2015/0282725 A1 | 10/2015 | Single |
| 2015/0313487 A1 | 11/2015 | Single |
| 2015/0360031 A1 | 12/2015 | Bornzin et al. |
| 2015/0374999 A1 | 12/2015 | Parker |
| 2016/0082265 A1 | 3/2016 | Moffitt et al. |

(56) References Cited

U.S. PATENT DOCUMENTS

| | | |
|---|---|---|
| 2016/0082268 A1 | 3/2016 | Hershey et al. |
| 2016/0101289 A1 | 4/2016 | Stolen et al. |
| 2016/0106980 A1 | 4/2016 | Sürth et al. |
| 2016/0121124 A1 | 5/2016 | Johanek et al. |
| 2016/0129272 A1 | 5/2016 | Hou et al. |
| 2016/0144189 A1 | 5/2016 | Bakker et al. |
| 2016/0166164 A1 | 6/2016 | Obradovic et al. |
| 2016/0175594 A1* | 6/2016 | Min .................. A61N 1/3615 607/72 |
| 2016/0287126 A1 | 10/2016 | Parker et al. |
| 2016/0287182 A1 | 10/2016 | Single |
| 2016/0367808 A9 | 12/2016 | Simon et al. |
| 2017/0001017 A9 | 1/2017 | Parker et al. |
| 2017/0049345 A1 | 2/2017 | Single |
| 2017/0071490 A1 | 3/2017 | Parker et al. |
| 2017/0135624 A1 | 5/2017 | Parker |
| 2017/0157410 A1 | 6/2017 | Moffitt et al. |
| 2017/0173326 A1 | 6/2017 | Bloch et al. |
| 2017/0173335 A1 | 6/2017 | Min et al. |
| 2017/0173341 A1 | 6/2017 | Johanek et al. |
| 2017/0216587 A1 | 8/2017 | Parker |
| 2017/0361101 A1 | 12/2017 | Single |
| 2018/0071513 A1 | 3/2018 | Weiss et al. |
| 2018/0104493 A1 | 4/2018 | Doan et al. |
| 2018/0110987 A1 | 4/2018 | Parker |
| 2018/0117335 A1 | 5/2018 | Parker et al. |
| 2018/0132747 A1 | 5/2018 | Parker et al. |
| 2018/0132760 A1 | 5/2018 | Parker |
| 2018/0133459 A1 | 5/2018 | Parker et al. |
| 2018/0228391 A1 | 8/2018 | Parker et al. |
| 2018/0228547 A1 | 8/2018 | Parker |
| 2018/0229046 A1 | 8/2018 | Parker et al. |
| 2018/0256052 A1 | 9/2018 | Parker et al. |
| 2019/0001139 A1 | 1/2019 | Mishra et al. |
| 2019/0030339 A1 | 1/2019 | Baru et al. |
| 2019/0125269 A1 | 5/2019 | Markovic et al. |
| 2019/0168000 A1 | 6/2019 | Laird-wah |
| 2019/0216343 A1 | 7/2019 | Single et al. |
| 2019/0239768 A1 | 8/2019 | Karantonis et al. |
| 2019/0307341 A1 | 10/2019 | Parker et al. |
| 2019/0357788 A1 | 11/2019 | Single |
| 2020/0029914 A1 | 1/2020 | Single |
| 2020/0129108 A1 | 4/2020 | Parker et al. |
| 2020/0155240 A1 | 5/2020 | Parker et al. |
| 2020/0215331 A1 | 7/2020 | Single |
| 2020/0282208 A1 | 9/2020 | Parker |
| 2021/0001133 A1 | 1/2021 | Williams et al. |
| 2021/0008373 A1 | 1/2021 | Single et al. |
| 2021/0016091 A1 | 1/2021 | Parker et al. |
| 2021/0162214 A1 | 6/2021 | Parker |
| 2021/0267518 A1 | 9/2021 | Parker et al. |
| 2021/0308449 A1 | 10/2021 | Parker |
| 2021/0315502 A1 | 10/2021 | Parker et al. |
| 2021/0379386 A1 | 12/2021 | Parker et al. |
| 2021/0387005 A1 | 12/2021 | Parker et al. |
| 2021/0387008 A1 | 12/2021 | Single |
| 2021/0393964 A1 | 12/2021 | Single et al. |
| 2022/0007987 A1 | 1/2022 | Huang et al. |
| 2022/0039724 A1 | 2/2022 | Parker et al. |
| 2022/0151535 A1 | 5/2022 | Parker et al. |
| 2022/0151536 A1 | 5/2022 | Karantonis et al. |
| 2022/0168574 A1 | 6/2022 | Wah |
| 2022/0249009 A1 | 8/2022 | Parker et al. |
| 2022/0287620 A1 | 9/2022 | Parker |

FOREIGN PATENT DOCUMENTS

| | | |
|---|---|---|
| CN | 103654762 A | 3/2014 |
| CN | 103842022 A | 6/2014 |
| CN | 104411360 A | 3/2015 |
| EP | 0219084 | 4/1987 |
| EP | 1244496 A1 | 10/2002 |
| EP | 0998958 B1 | 8/2005 |
| EP | 2019716 A | 11/2007 |
| EP | 2243510 A2 | 10/2010 |
| EP | 2443995 A2 | 4/2012 |
| EP | 2520327 A2 | 11/2012 |
| EP | 2707095 A1 | 3/2014 |
| EP | 3229893 A1 | 10/2017 |
| JP | 2006504494 A | 2/2006 |
| JP | 2009512505 A | 3/2009 |
| JP | 2012524629 | 10/2012 |
| JP | 2013500779 A | 1/2013 |
| JP | 2013527784 A | 7/2013 |
| JP | 2013536044 A | 9/2013 |
| JP | 2014522261 A | 9/2014 |
| JP | 2014523261 A | 9/2014 |
| WO | 1983003191 A | 9/1983 |
| WO | 1993001863 A1 | 2/1993 |
| WO | 1996012383 A1 | 4/1996 |
| WO | 2000002623 A1 | 1/2000 |
| WO | 2002036003 A1 | 11/2001 |
| WO | 2002038031 | 5/2002 |
| WO | 2002049500 A2 | 6/2002 |
| WO | 2002082982 A1 | 10/2002 |
| WO | 2003028521 A2 | 4/2003 |
| WO | 2003043690 | 5/2003 |
| WO | 2003103484 | 12/2003 |
| WO | 2004021885 A1 | 3/2004 |
| WO | 2004103455 | 12/2004 |
| WO | 2005032656 A1 | 4/2005 |
| WO | 2005105202 A1 | 11/2005 |
| WO | 2005122887 A2 | 12/2005 |
| WO | 2006091636 A2 | 8/2006 |
| WO | 2007050657 A1 | 5/2007 |
| WO | 2007064936 A1 | 6/2007 |
| WO | 2007127926 A2 | 11/2007 |
| WO | 2007130170 A1 | 11/2007 |
| WO | 2008004204 A1 | 1/2008 |
| WO | 2008049199 A1 | 5/2008 |
| WO | 2009002072 A2 | 12/2008 |
| WO | 2009002579 A1 | 12/2008 |
| WO | 2009010870 A2 | 1/2009 |
| WO | 2009130515 A2 | 10/2009 |
| WO | 2009146427 A1 | 12/2009 |
| WO | 2010013170 A1 | 2/2010 |
| WO | 2010044989 A2 | 4/2010 |
| WO | 2010051392 A1 | 5/2010 |
| WO | 2010051406 A1 | 5/2010 |
| WO | 2010057046 A2 | 5/2010 |
| WO | 2010124139 A1 | 10/2010 |
| WO | 2010138915 A1 | 12/2010 |
| WO | 2011011327 A1 | 1/2011 |
| WO | 2011014570 A1 | 2/2011 |
| WO | 2011017778 A1 | 2/2011 |
| WO | 2011066477 A1 | 6/2011 |
| WO | 2011066478 A1 | 6/2011 |
| WO | 2011112843 A1 | 9/2011 |
| WO | 2011119251 A2 | 9/2011 |
| WO | 2011159545 A2 | 12/2011 |
| WO | 2012016138 A1 | 2/2012 |
| WO | 2012027252 A2 | 3/2012 |
| WO | 2012027791 A1 | 3/2012 |
| WO | 2012155183 A1 | 11/2012 |
| WO | 2012155184 A1 | 11/2012 |
| WO | 2012155185 A1 | 11/2012 |
| WO | 2012155187 A1 | 11/2012 |
| WO | 2012155188 A1 | 11/2012 |
| WO | 2012155189 A1 | 11/2012 |
| WO | 2012155190 A1 | 11/2012 |
| WO | 2012162349 A1 | 11/2012 |
| WO | 2013063111 A1 | 5/2013 |
| WO | 2013075171 A1 | 5/2013 |
| WO | 2013116161 A1 | 8/2013 |
| WO | 2014071445 A1 | 5/2014 |
| WO | 2014071446 A1 | 5/2014 |
| WO | 2014143577 A1 | 9/2014 |
| WO | 2014150001 A1 | 9/2014 |
| WO | 2015070281 A1 | 5/2015 |
| WO | 2015074121 A1 | 5/2015 |
| WO | 2015109239 A1 | 7/2015 |
| WO | 2015143509 A1 | 10/2015 |
| WO | 2015168735 A1 | 11/2015 |

(56) References Cited

FOREIGN PATENT DOCUMENTS

| | | |
|---|---|---|
| WO | 2016011512 A1 | 1/2016 |
| WO | 2016048974 A1 | 3/2016 |
| WO | 2016059556 A1 | 4/2016 |
| WO | 2016077882 A1 | 5/2016 |
| WO | 2016090420 A1 | 6/2016 |
| WO | 2016090436 A1 | 6/2016 |
| WO | 2016115596 A1 | 7/2016 |
| WO | 2016161484 A2 | 10/2016 |
| WO | 2016168798 A1 | 10/2016 |
| WO | WO-2016161484 A2 * 10/2016 ......... A61N 1/36062 |
| WO | 2016191807 A1 | 12/2016 |
| WO | 2016191808 A1 | 12/2016 |
| WO | 2016191815 A1 | 12/2016 |
| WO | 2017053504 A1 | 3/2017 |
| WO | 2017142948 A1 | 8/2017 |
| WO | 2017173493 A1 | 10/2017 |
| WO | 2017210352 A1 | 12/2017 |
| WO | 2017219096 A1 | 12/2017 |
| WO | 2018080753 A1 | 5/2018 |
| WO | 2018119220 A1 | 6/2018 |
| WO | 2018160992 A1 | 9/2018 |
| WO | 2018170141 A1 | 9/2018 |
| WO | 2019178634 A1 | 9/2019 |
| WO | 2019204884 A1 | 10/2019 |
| WO | 2019210371 A1 | 11/2019 |
| WO | 2019231796 A1 | 12/2019 |
| WO | 2020082118 A1 | 4/2020 |
| WO | 2020082126 A1 | 4/2020 |
| WO | 2020082128 A1 | 4/2020 |
| WO | 2020087123 A1 | 5/2020 |
| WO | 2020087135 A1 | 5/2020 |
| WO | 2020124135 A1 | 6/2020 |
| WO | 2021007615 A1 | 1/2021 |
| WO | 2021146778 A1 | 7/2021 |
| WO | 2022040757 A1 | 3/2022 |
| WO | 2022170388 A1 | 8/2022 |

OTHER PUBLICATIONS

International Search Report and Written Opinion for International Application No. PCT/AU2015/050787, Search completed Mar. 16, 2016, dated Mar. 16, 2016, 10 pgs.
International Search Report and Written Opinion for International Application No. PCT/AU2016/050019, Search completed May 4, 2016, dated May 4, 2016, 16 pgs.
International Search Report and Written Opinion for International Application No. PCT/AU2016/050263, Search completed Nov. 16, 2016, dated Nov. 16, 2016, 8 pgs.
International Search Report and Written Opinion for International Application No. PCT/AU2016/050430, Search completed Aug. 16, 2016, dated Aug. 16, 2016, 10 pgs.
International Search Report and Written Opinion for International Application No. PCT/AU2016/050431, Search completed Aug. 16, 2016, dated Aug. 16, 2016, 11 pgs.
International Search Report and Written Opinion for International Application No. PCT/AU2016/050439, Search completed Jul. 15, 2016, dated Jul. 15, 2016, 8 pgs.
International Search Report and Written Opinion for International Application No. PCT/AU2017/050296, Search completed Jul. 28, 2017, dated Jul. 28, 2017, 10 pgs.
International Search Report and Written Opinion for International Application No. PCT/AU2017/050647, Search completed Sep. 29, 2017, dated Sep. 29, 2017, 13 pgs.
International Search Report and Written Opinion for International Application No. PCT/AU2018/050278, Search completed Jun. 18, 2018, dated Jun. 18, 2018, 12 pgs.
International Search Report and Written Opinion for International Application No. PCT/AU2019/050384, Search completed Jun. 25, 2019, dated Jun. 25, 2019, 15 pgs.
International Search Report and Written Opinion for International Application No. PCT/AU2015/050215, Search completed Jul. 30, 2015, dated Jul. 30, 2015, 8 pgs.
International Search Report for Australian Application 2011901829, Search Completed Feb. 6, 2012, dated Feb. 7, 2012, 3pgs.
International Search Report for International Application No. PCT/AU2012/000511, International Filing Date May 11, 2012, Search Completed May 17, 2012, dated May 18, 2012, 4 pgs.
International Search Report for International Application No. PCT/AU2012/000512, International Filing Date May 11, 2012, Search Completed Jul. 10, 2012, dated Jul. 11, 2012, 4 pgs.
International Search Report for International Application No. PCT/AU2012/000513, International Filing Date May 11, 2012, Search Completed May 29, 2012, dated May 30, 2012, 5 pgs.
International Search Report for International Application No. PCT/AU2012/000515, International Filing Date May 11, 2012, Search Completed May 21, 2012, dated Jun. 4, 2012, 5 pgs.
International Search Report for International Application No. PCT/AU2012/000516, International Filing Date May 11, 2012, Search Completed Jul. 11, 2012, dated Jul. 12, 2012, 8 pgs.
International Search Report for International Application No. PCT/AU2012/000517, International Filing Date May 11, 2012, Search Completed Jun. 4, 2012, dated Jun. 6, 2012, 3 pgs.
International Search Report for International Application No. PCT/AU2012/000518, International Filing Date May 11, 2012, Search Completed Jun. 8, 2012, dated Jun. 12, 2012, 4 pgs.
International Type Search Report for International Application No. AU 2015902393, Search completed May 16, 2016, dated May 16, 2016, 8 Pgs.
Japanese Office Action for Application No. 2017-546830, dated Feb. 20, 2020, 5 pages with English translation.
Japanese Office Action for Application No. 2017-553090, dated Mar. 16, 2020, 12 pages with English translation.
Japanese Office Action for Application No. 2018-513699, dated Jun. 8, 2020, 7 pages with English translation.
Massachusetts Institute of Technology, The Compound Action Potential of the Frog Sciatic Nerve, Quantitative Physiology: Cells and Tissues. Fall, 1999, Retrieved from http://umech.mit.edu/freeman/6.021J/2001/lab.pdf on May 22, 2012.
Medtronic, Spinal Cord Stimulation, RestoreSensor Neurostimulator, Features and Specification: Specification, Printed Jun. 16, 2014, 2 pgs.
Medtronic, Spinal Cord Stimulation, RestoreSensor Neurostimulator, Features and Specification: Summary Printed Jun. 16, 2014, 1 pg.
Office Action for Chinese Patent Application No. 201680020725.4, dated Mar. 16, 2020, 8 pgs.
Partial European Search Report for European Application No. 16775966.1, Search completed Oct. 26, 2018, dated Nov. 6, 2018, 11 Pgs.
Written Opinion for International Application No. PCT/AU2012/000511, International Filing Date May 11, 2012, Search Completed May 17, 2012, dated May 18, 2012, 5 pgs.
Written Opinion for International Application No. PCT/AU2012/000512, International Filing Date May 11, 2012, Search Completed Jul. 10, 2012, dated Jul. 11, 2012, 7 pgs.
Written Opinion for International Application No. PCT/AU2012/000513, International Filing Date May 11, 2012, Search Completed May 29, 2012, dated May 30, 2012, 10 pgs.
Written Opinion for International Application No. PCT/AU2012/000515, International Filing Date May 11, 2012, Search Completed May 21, 2012, dated Jun. 4, 2012, 4 pgs.
Written Opinion for International Application No. PCT/AU2012/000516, International Filing Date May 11, 2012, Search Completed Jul. 11, 2012, dated Jul. 12, 2012, 8 pgs.
Written Opinion for International Application No. PCT/AU2012/000517, International Filing Date May 11, 2012, Search Completed Jun. 4, 2012, dated Jun. 6, 2012, 5 pgs.
Written Opinion for International Application No. PCT/AU2012/000518, International Filing Date May 11, 2012, Search Completed Jun. 8, 2012, dated Jun. 12, 2012, 10 pgs.
Medtronic, RestoreSensor Neurostimulator, Retrieved from: http://web.archive.org/web/20150328092923/http://professional.medtronic.com:80/pt/neuro/scs/prod/restore-sensor/features-specifications/index.htm, Capture Date Jul. 9, 2012, Printed on May 11, 2017.

(56) References Cited

OTHER PUBLICATIONS

"Advanced Pain Therapy using Neurostimulation for Chronic Pain", Medtronic RestoreSensor clinical trial paper, Clinical summary, Nov. 2011, p. 32.
"Battelle Neurotechnology—Moving Beyond The Limits In Neurotechnology", Battelle, www.battelle.org, May 2014, pp. 1-2.
"Haptic technology", Wikipedia, Retrieved from: http://en.wikipedia.org/wiki/Haptic_technology, Last modified on Sep. 15, 2014, Printed on Sep. 15, 2014, 5 pgs.
"Implants for surgery, Cardiac pacemakers", IS-1 standard ISO 5841-3-2000, Oct. 15, 2000.
"Neural Bypass Technology Enables Movement in Paralyzed Patient", Posted on Jul. 29, 2014, 6 a.m. in Brain chips/computer interface, pp. 1-2.
"Spinal Cord Stimulation, About Spinal Cord Stimulation", Medtronic, Retrieved from: http://professional.medtronic.com/pt/neuro/scs/edu/about/index.htm, Printed on Jun. 16, 2014, 2 pgs.
"Wide bandwidth BioAmplifier", http://www.psylab.com/html/default_bioamp.htm, Printed Jan. 30, 2014, 1-3 pages.
Alam et al., "Evaluation of optimal electrode configurations for epidural spinal cord stimulation in cervical spinal cord injured rats", Journal of Neuroscience Methods, Mar. 2015, 28 pgs.
Al-Ani et al., "Automatic removal of high-amplitude stimulus artefact from neuronal signal recorded in the subthalamic nucleus", Journal of Neuroscience Methods, vol. 198, Issue 1, 2011, pp. 135-146.
Andreassen, S. et al. "Muscle Fibre Conduction Velocity in Motor Units of the Human Anterior Tibial Muscle: a New Size Principle Parameter", J. Physiol, (1987), 391, pp. 561-571.
Andy, "Parafascicular-Center Median Nuclei Stimulation for Intractable Pain and Dyskinesia (Painful—Dyskinesia)", Stereotactic and Functional Neurosurgery, Appl. Neurophysiol., 43, No. 3-5, 1980, pp. 133-144.
Bahmer et al., "Application of triphasic pulses with adjustable phase amplitude ratio (PAR) for cochlear ECAP recording: I. Amplitude growth functions", Journal of Neuroscience Methods, Clinical Neuroscience, 2012, vol. 205, pp. 202-211.
Bahmer et al., "Effects of electrical pulse polarity shape on intra cochlear neural responses in humans: Triphasic pulses with cathodic second phase", Hearing Research, 2013, vol. 306, pp. 123-130.
Balzer et al., "Localization of cervical and cervicomedullary stimulation leads for pain treatment using median nerve somatosensay evoked potential collision testing", Journal of Neurosurgery, Jan. 2011, vol. 114, No. 1, pp. 200-205.
Blum, A. R. "An Electronic System for Extracellular Neural Stimulation and Recording", Dissertation, Georgia Institute of Technology, Aug. 2007, Retrieved from http://smartech.gatech.edu/handle/1853/16192 on Jan. 30, 2012.
Matzner et al., "Na+ Conductance and the Threshold for Repetitive Neuronal Firing", Brain Research 597, No. 1 (Nov. 27, 1992), pp. 92-98, doi:10.1016/0006-8993(92)91509-D.
McGill, Kevin et al., "On the Nature and Elimination of Stimulus Artifact in Nerve Signals Evoked and Recorded Using Surface Electrodes", IEEE Transactions on Biomedical Engineering, vol. BME-29, No. 2, Feb. 1982, pp. 129-137.
Melzack et al., "Pain mechanisms: a new theory", Science, New York, New York, vol. 150, No. 3699, Nov. 19, 1965, pp. 971-979.
Miles et al., "An Electrode for Prolonged Stimulation of the Brain", Proc. 8th Meeting World Soc. Stereotactic and Functional Neurosurgery, Part III, Zurich, 1981, Appl. Neurophysiol, 45, 1982, pp. 449-445.
Misawa et al., "Neuropathic Pain Is Associated with Increased Nodal Persistent Na(+) Currents in Human Diabetic Neuropathy", Journal of the Peripheral Nervous System: JPNS, 14, No. 4 (Dec. 2009): 279-284.
Nordin et al., "Ectopic Sensory Discharges and Paresthesiae in Patients with Disorders of Peripheral Nerves, Dorsal Roots and Dorsal Columns", Pain 20, No. 3 (Nov. 1984): 231-245, doi:10.1016/0304-3959(84)90013-7.
Oakley et al., "Spinal Cord Stimulation: Mechanisms of Action", Spine 27, No. 22, Nov. 15, 2002, pp. 2574-2583.
Oakley et al., "Transverse Tripolar Spinal Cord Stimulation: Results of an International Multicenter Study", Neuromodulation, vol. 9, No. 3, 2006, pp. 192-203.
Obradovic et al., "Effect of pressure on the spinal cord during spinal cord stimulation in an animal model", Poster, 18th Annual Meeting of the North American Neuromodulation Society, Dec. 11-14, 2014, Las Vegas.
Oh et al., "Long-term hardware-related complications of deep brain stimulation", Neurosurgery, vol. 50, No. 6, Jun. 2002, pp. 1268-1274, discussion pp. 1274-1276.
Olin et al., "Postural Changes in Spinal Cord Stimulation Perceptual Thresholds", Neuromodulation, vol. 1 , No. 4, 1998, pp. 171-175.
Opsommer, E. et al. "Determination of Nerve Conduction Velocity of C-fibres in Humans from Thermal Thresholds to Contact Heat (Thermode) and from Evoked Brain Potentials to Radiant Heat (CO2 Laser)", Neurophysiologie Clinique 1999, vol. 29, pp. 411-422.
Orstavik, Kristin et al. "Pathological C-fibres in patients with a chronic painful condition", Brain (2003), 126, 567-578.
Ouyang et al., "Compression Induces Acute Demyelination and Potassium Channel Exposure in Spinal Cord", Journal of Neurotrauma 27, No. 6, Jun. 2010, 1109-1120, doi:10.1089/neu.2010.1271.
Parker et al., "Closing the Loop in Neuromodulation Therapies: Spinal Cord Evoked Compound Action Potentials During Stimulation for Pain Management (230).", 2011, In 15th Annual Meeting, North American Neuromodulation Society (p. 48). Presented at the North American Neuromodulation Society, Las Vegas.
Parker et al., "Compound Action Potentials Recorded in the Human Spinal Cord During Neurostimulation for Pain Relief", Pain, vol. 153, 2012, pp. 593-601.
Parker et al., "Electrically Evoked Compound Action Potentials Recorded From the Sheep Spinal Cord", Neuromodulation, vol. 16, 2013, pp. 295-303.
Penar et al., "Cortical Evoked Potentials Used for Placement of a Laminotomy Lead Array: A Case Report", Neuromodulation: Technology at the Neural Interface, accessed Apr. 19, 2011, doi:10.1111/j.1525-1403.2011.00352.x.
Rattay, "Analysis of Models for External Stimulation of Axons", IEEE Transactions on Biomedical Engineering, vol. BME-33, No. 10, Oct. 1986, pp. 974-977.
Richter et al., "EMG and SSEP Monitoring During Cervical Spinal Cord Stimulation", Journal of Neurosurgical Review 2011, Southern Academic Press, 1(S1), 2011, pp. 61-63.
Ridder et al., "Burst Spinal Cord Stimulation for Limb and Back Pain", World Neurosurgery, 2013, 9 pgs.
Ross et al., "Improving Patient Experience with Spinal Cord Stimulation: Implications of Position-Related Changes in Neurostimulation", Neuromodulation 2011; e-pub ahead of print. DOI: 10.1111/j.1525-1403.2011.00407.x, 6 pages.
Roy, S. H. et al., "Effects of Electrode Location on Myoelectric Conduction Velocity and Median Frequency Estimates", J. Appl. Physiol. 61 (4), 1986, pp. 1510-1517.
Sayenko et al., "Neuromodulation of evoked muscle potentials induced by epidural spinal-cord stimulation in paralyzed individuals", Journal of Neurophysiology, vol. 111, No. 5, 2014, pp. 1088-1099, First published Dec. 11, 2013.
Schmidt et al., "Gating of tactile input from the hand", Exp Brain Res, 1990, 79, pp. 97-102.
Siegfried et al., "Bilateral Chronic Electrostimulation of Ventroposterolateral Pallidum: A New Therapeutic Approach for Alleviating all Parkinsonian Symptoms", Neurosurgery, 35, No. 6, Dec. 1994, pp. 1126-1130.
Siegfried et al., "Intracerebral Electrode Implantation System", Journal of Neurosurgery, vol. 59, No. 2, Aug. 1983, pp. 356-359.
Srinivasan, S "Electrode/Electrolyte Interfaces: Structure and Kinetics of Charge Transfer", Fuel Cells, 2006, Chapter 2, 67 Pages.
Struijk, "The Extracellular Potential of a Myelinated Nerve Fiber in an Unbounded Medium and in Nerve Cuff Models", Biophysical Journal vol. 72 Jun. 1997 2457-2469.

(56) References Cited

OTHER PUBLICATIONS

Struijk et al, "Paresthesia Thresholds in Spinal Cord Stimulation: A Comparison of Theoretical Results with Clinical Data", IEEE Transactions on Rehabilitation Engineering, vol. 1, No. 2, Jun. 1993, pp. 101-108.
Struijk et al., "Excitation of Dorsal Root Fibers in Spinal Cord Stimulation: a Theoretical Study", IEEE Transactions on Biomedical Engineering, Jul. 1993, vol. 40, No. 7, pp. 632-639.
Sufka et al., "Gate Control Theory Reconsidered", Brain and Mind, 3, No. 2, 2002, pp. 277-290.
Tamura et al., "Increased Nodal Persistent Na+ Currents in Human Neuropathy and Motor Neuron Disease Estimated by Latent Addition", Clinical Neurophysiology 117, No. 11 (Nov. 2006): 2451-2458, doi:10.1016/j.clinph.2006.07.309.
Tasker, "Deep Brain Stimulation is Preferable to Thalamotomy for Tremor Suppression", Surgical Neurology, 49, No. 2, 1998, pp. 145-153.
Taylor et al., "Spinal Cord Stimulation for Chronic Back and Leg Pain and Failed Back Surgery Syndrome: A Systematic Review and Analysis of Prognostic Factors", Spine, vol. 30, No. 1, 2004, pp. 152-160.
Texas Instruments, "Precision, Low Power Instrumentation Amplifiers", Texas Instruments SBOS051B Oct. 1995, Revised Feb. 2005, 20 pgs.
Tomas et al., "Dorsal Root Entry Zone (DREZ) Localization Using Direct Spinal Cord Stimulation Can Improve Results of the DREZ Thermocoagulation Procedure for Intractable Pain Relief", Pain, 2005, vol. 116, pp. 159-163.
Tronnier et al., "Magnetic Resonance Imaging with Implanted Neurostimulators: An In Vitro and In Vivo Study", Jan. 1999, Neurosurgery, vol. 44(1), p. 118-125 (Year: 1999).
Tscherter et al., "Spatiotemporal Characterization of Rhythmic Activity in Rat Spinal Cord Slice Cultures", European Journal of Neuroscience 14, No. 2 (2001), pp. 179-190.
Van Den Berg et al., "Nerve fiber size-related block of action currents by phenytoin in mammalian nerve", Epilepsia, Nov. 1994, 35(6), pp. 1279-1288.
Villavicencio, Alan T. "Laminectomy versus Percutaneous Electrode Placement for Spinal Cord Stimulation," Neurosurgery, vol. 46 (2), Feb. 2000, pp. 399-405.
Vleggeert et al., Lankamp "Electrophysiology and morphometry of the Aalpha- and Abeta-fiber populations in the normal and regenerating rat sciatic nerve", Experimental Neurology, vol. 187, No. 2, Jun. 1, 2004, Available online Apr. 2, 2004, pp. 337-349.
Woessner, "Blocking Out the Pain, Electric Nerve Block Treatments for Sciatic Neuritis", Retrieved from: http://www.practicalpainmanagement.com/pain/spine/radiculopathy/blocking-out-pain, Last updated Jan. 10, 2012.
Wolter et al., "Effects of sub-perception threshold spinal cord stimulation in neuropathic pain: A randomized controlled double-blind crossover study", European Federation of International Association for the Study of Pain Chapters, 2012, pp. 648-655.
Wu et al., "Changes in Aβ Non-nociceptive Primary Sensory Neurons in a Rat Model of Osteoarthritis Pain", Molecular Pain 6, No. 1 (Jul. 1, 2010): 37, doi:10.1186/1744-8069-6-37.
Xie et al., "Functional Changes in Dorsal Root Ganglion Cells after Chronic Nerve Constriction in the Rat", Journal of Neurophysiology 73, No. 5 (May 1, 1995): 1811-1820.
Xie et al., "Sinusoidal Time-Frequency Wavelet Family and its Application in Electrograstrographic Signal Analysis", Proceedings of the 20th Annual International Conference of the IEEE Engineering in Medicine and Biology Society, vol. 20, No. 3, Oct. 29, 1998, pp. 1450-1453.
Yamada et al., "Extraction and Analysis of the Single Motor Unit F-Wave of the Median Nerve", EMG Methods for Evaluating Muscle and Nerve Function, InTech, 2012, 15 pgs.
Yearwood, T. L. "Pulse Width Programming in Spinal Cord Stimulation: a Clinical Study", Pain Physician. 2010. vol. 13, pp. 321-335.

Yingling et al., "Use of Antidromic Evoked Potentials in Placement of Dorsal Cord Disc Electrodes", Applied Neurophysiology, 1986, vol. 49, pp. 36-41.
Yuan, S. et al. "Recording monophasic action potentials using a platinum-electrode ablation catheter", Europace. Oct. 2000; 2(4):312-319.
European Search Report for European Application 12785619.3 Search Completed Oct. 13, 2014, dated Oct. 23, 2014, 7 pgs.
European Search Report for European Application 12785669.8 Search Completed Sep. 22, 2014, dated Sep. 29, 2014, 5 pgs.
European Search Report for European Application No. 15861444.6, Search completed Jul. 13, 2018, dated Jul. 23, 2018, 8 pgs.
Extended European Search Report for EP Application 12785483.4 completed Sep. 16, 2014, 7 pgs.
Extended European Search Report for European Application No. 11820923.8, report completed Dec. 9, 2013, report dated Dec. 17, 2013, 6 pgs.
Extended European Search Report for European Application No. 13852669.4, Search completed Jun. 8, 2016, dated Jun. 22, 2016, 09 pgs.
Extended European Search Report for European Application No. 14861553.7, Search completed Jun. 8, 2017, daated Jun. 19, 2017, 8 pgs.
Extended European Search Report for European Application No. 14863597.2, Search completed Jun. 6, 2017, dated Jun. 13, 2017, 9 pgs.
Extended European Search Report for European Application No. 15768956.3, Search completed Oct. 3, 2017, dated Oct. 10, 2017, 8 pgs.
Extended European Search Report for European Application No. 15789515.2, Search completed Dec. 4, 2017, dated Jan. 30, 2018, 7 pgs.
Extended European Search Report for European Application No. 16739680.3, Search completed Jun. 1, 2018, dated Jun. 12, 2018, 9 pgs.
Extended European Search Report for European Application No. 16802237.4, Search completed Dec. 11, 2018, dated Dec. 19, 2018, 9 pgs.
Extended European Search Report for European Application No. 16802238.2, Search completed Oct. 17, 2018, dated Oct. 24, 2018, 8 pgs.
Extended European Search Report for European Application No. 17778477.4, report completed Nov. 12, 2019, dated Nov. 20, 2019, 7 pgs.
Extended European Search Report for European Application No. 17814341.8, report completed Dec. 12, 2019, report dated Jan. 2, 2020, 8 pgs.
Extended European Search Report for European Application No. 13853514.1, Search completed Jun. 8, 2016, dated Jun. 15, 2016, 07 pgs.
International Preliminary Report for International Application No. PCT/AU2017/050296, dated Oct. 9, 2018, 7 pgs.
International Preliminary Report for International Application No. PCT/AU2017/050647, dated Dec. 25, 2018, 8 pgs.
International Preliminary Report on Patentability for International Application No. PCT/AU2011/001127, Report dated Mar. 5, 2013, 9 pgs.
International Preliminary Report on Patentability for International Application No. PCT/AU2012/000511, Report dated Nov. 19, 2013, 6 pgs.
International Preliminary Report on Patentability for International Application No. PCT/AU2012/000512, Report dated Nov. 19, 2013, 8 pgs.
International Preliminary Report on Patentability for International Application No. PCT/AU2012/000513, Report dated Nov. 19, 2013, 11 pgs.
International Preliminary Report on Patentability for International Application No. PCT/AU2012/000515, Report dated Nov. 19, 2013, 5 pgs.
International Preliminary Report on Patentability for International Application No. PCT/AU2012/000516, Report dated Nov. 19, 2013, 9 pgs.

(56) References Cited

OTHER PUBLICATIONS

International Preliminary Report on Patentability for International Application No. PCT/AU2012/000517, Report dated Nov. 19, 2013, 6 pgs.
International Preliminary Report on Patentability for International Application No. PCT/AU2012/000518, Report dated Nov. 19, 2013, 11 pgs.
International Preliminary Report on Patentability for International Application No. PCT/AU2012/001441, Report dated May 27, 2014, 10 pgs.
International Preliminary Report on Patentability for International Application No. PCT/AU2013/001279, Report dated May 12, 2015, 6 pgs.
International Preliminary Report on Patentability for International Application No. PCT/AU2013/001280, Report dated May 12, 2015, 6 pgs.
International Preliminary Report on Patentability for International Application No. PCT/AU2014/001049, Report dated May 17, 2016, 5 pgs.
International Preliminary Report on Patentability for International Application No. PCT/AU2014/050369, Report dated May 24, 2016, 8 pgs.
International Preliminary Report on Patentability for International Application No. PCT/AU2015/050135, Report dated Oct. 4, 2016, 13 pgs.
International Preliminary Report on Patentability for International Application No. PCT/AU2015/050215, Report dated Nov. 8, 2016, 4 pgs.
International Preliminary Report on Patentability for International Application No. PCT/AU2015/050422, Report dated Jan. 31, 2017, 8 pgs.
International Preliminary Report on Patentability for International Application No. PCT/AU2015/050724, Report dated May 23, 2017, 5 pgs.
International Preliminary Report on Patentability for International Application No. PCT/AU2015/050753, Report dated Jun. 13, 2017, 7 pgs.
International Preliminary Report on Patentability for International Application No. PCT/AU2015/050787, Report dated Jun. 13, 2017, 6 pgs.
International Preliminary Report on Patentability for International Application No. PCT/AU2016/050019, Report dated Jul. 25, 2017, 9 pgs.
International Preliminary Report on Patentability for International Application No. PCT/AU2016/050263, Report dated Oct. 10, 2017, 9 pgs.
International Preliminary Report on Patentability for International Application No. PCT/AU2018/050278, dated Sep. 29, 2020, 7 pgs.
International Preliminary Report on Patentability for International Application No. PCT/AU2019/050384, dated Oct. 27, 2020, 8 pgs.
International Search Report & Written Opinion for International Application No. PCT/AU2013/001280, Search Completed Jan. 16, 2014, dated Jan. 16, 2014, 8 Pgs.
International Search Report & Written Opinion for International Application PCT/AU2013/001279, Search Completed Jan. 9, 2014, dated Jan. 9, 2014, 9 Pgs.
International Search Report and Written Opinion for International Application No. PCT/AU2011/001127, date completed Nov. 11, 2011, dated Nov. 15, 2011, 13 pgs.
International Search Report and Written Opinion for International Application No. PCT/AU2012/001441, International Filing Date Nov. 23, 2012, Search Completed Feb. 26, 2013, dated Feb. 26, 2013, 14 pgs.
International Search Report and Written Opinion for International Application No. PCT/AU2014/001049, Search completed Feb. 10, 2015, dated Feb. 10, 2015, 8 pgs.
International Search Report and Written Opinion for International Application No. PCT/AU2014/050369, Search completed Feb. 20, 2015, dated Feb. 20, 2015, 14 pgs.
International Search Report and Written Opinion for International Application No. PCT/AU2015/050135, Search completed Jun. 30, 2015, dated Jun. 30, 2015, 26 pgs.
International Search Report and Written Opinion for International Application No. PCT/AU2015/050422, Search completed Oct. 14, 2015, dated Oct. 14, 2015, 17 pgs.
International Search Report and Written Opinion for International Application No. PCT/AU2015/050724, Search completed May 9, 2016, dated May 9, 2016, 8 pgs.
International Search Report and Written Opinion for International Application No. PCT/AU2015/050753, Search completed Feb. 10, 2016, dated Feb. 10, 2016, 10 pgs.
Borg et al., "Conduction velocity and refractory period of single motor nerve fibres in antecedent poliomyelitis", Journal of Neurology, Neurosurgery, and Psychiatry, vol. 50, 1987, pp. 443-446.
Brown et al., "Impact of Deep Brain Stimulation on Upper Limb Askinesia in Parkinson's Disease", Annals of Neurology, 45, No. 4, 1999, pp. 473-488.
Budagavi et al., "Modelling of compound nerve action potentials health and disease", Engineering in Medicine and Biology Society, 1992 14th Annual International Conference of the IEEE. vol. 6. IEEE, 1992, pp. 2600-2601.
Coquery et al., "Backward and forward masking in the perception of cutaneous stimuli", Perception & Psychophysics, 1973, vol. 13.No. 2, pp. 161-163.
Dawson, G. D. "The relative excitability and conduction velocity of sensory and motor nerve fibres in man", Journal of Physiology, 1956, vol. 131(2), pp. 436-451.
De Ridder et al., "Burst Spinal Cord Stimulation toward Paresthesia-Free Pain Suppression", Nuerosurgery-online.com, May 2010, vol. 66, No. 8, pp. 986-990.
Devergnas et al., A "Cortical potentials evoked by deep brain stimulation in the subthalamic area", Frontiers in System Neuroscience, May 13, 2011, vol. 5, Article 30, 2011, doi:10.3389/fnsys.2011.00030.
Dijkstra, E. A. "Ultrasonic Distance Detection for a Closed-Loop Spinal Cord Stimulation System", Proceedings—19th International Conference—IEEE/EMBS Oct. 30-Nov. 2, 1997, Chicago, IL, 4 pgs.
Dillier, N et al., "Measurement of the electrically evoked compound action potential via a neural response telemetry system", Ann. Otol. Rhinol. Laryngol., vol. 111, No. 5, May 2002, pp. 407-414.
Doiron et al., "Persistent Na+ Current Modifies Burst Discharge by Regulating Conditional Backpropagation of Dendritic Spikes", Journal of Neurophysiology 89, No. 1 (Jan. 1, 2003): 324-337, doi:10.1152/jn.00729.2002.
England et al., "Increased Nos. of Sodium Channels Form Along Demyelinated Axons", Brain Research, vol. 548, No. 1-2, May 10, 1991, pp. 334-337.
Fagius, J. et al. "Sympathetic Reflex Latencies and Conduction Velocities in Normal Man", Journal of Neurological Sciences, 1980, vol. 47, pp. 433-448.
Falowski et al., "Spinal Cord Stimulation: an update", Neurotherapeutics: The Journal of the American Society for Experimental NeuroTherapeutics, vol. 5, No. 1, Jan. 2008, pp. 86-99.
Fisher, "F-Waves—Physiology and Clinical Uses", TheScientificWorldJournal, (2007) vol. 7, pp. 144-160.
Franke et al., Felix "An Online Spike Detection and Spike Classification Algorithm Capable of Instantaneous Resolution of Overlapping Spikes", Journal of Computational Neuroscience, 2010, vol. 29, No. 1-2, pp. 127-148.
French et al., "Information transmission at 500 bits/s by action potentials in a mechanosensory neuron of the cockroach", Neuroscience Letters, vol. 243, No. 1-3, Feb. 1, 1998, pp. 113-116.
Fuentes et al., "Spinal Cord Stimulation Restores Locomotion in Animal Models of Parkinson's Disease", Science, vol. 323, No. 5921, Mar. 20, 2009, pp. 1578-1582.
Gad et al., "Development of a multi-electrode array for spinal cord epidural stimulation to facilitate stepping and standing after a complete spinal cord injury in adult rats", Journal of NeuroEngineering and Rehabilitation 2013, vol. 10, No. 2, 18 pgs., http://www.jneuroengrehab.com/content/10/1/2.

(56) References Cited

OTHER PUBLICATIONS

George et al., "Vagus nerve stimulation: a new tool for brain research and therapy", Biological Psychiatry 47, No. 4, Feb. 15, 2000, pp. 287-295.

Gnadt et al., "Spectral Cancellation of Microstimulation Artifact for Simultaneous Neural Recording In Situ", IEEE Transactions on Biomedical Engineering, Oct. 2003, Date of Publication: Sep. 23, 2003, vol. 50, No. 10, pp. 1129-1135, DOI: 10.1109/TBME.2003.816077.

Goodall, E. V. "Modeling Study of Activation and Propagation delays During Stimulation of Peripheral Nerve Fibres with a Tripolar Cuff Electrode", IEEE Transactions on Rehabilitation Engineering, vol. 3, No. 3, Sep. 1995, pp. 272-282.

Gorman et al., "ECAP Mapping of the Spinal Cord: Influence of Electrode Position on Aβ Recruitment", (2012).,In 16th Annual Meeting. Presented at the North American Neuromodulation Society, Las Vegas, NV.

Gorman et al., "Neural Recordings for Feedback Control of Spinal Cord Stimulation: Reduction of Paresthesia Variability.", 2013, In International Neuromodulation Society 11th World Congress. Presented at the International Neuromodulation Society 11th World Congress, Berlin, Germany, 2 pgs.

Hallstrom et al, "Distribution of lumbar spinal evoked potentials and their correlation with stimulation-induced paresthesiae", Electroencephalography and Clinical Neurophysiology, Mar.-Apr. 1991, vol. 80, No. 2, pp. 126-139, doi:10.1016/0168-5597(91)90150-V.

Harper, A. A. et al., "Conduction Velocity is Related to Morphological Cell Type in Rat Dorsal Root Ganglion Neurones", J. Physiol, (1985), vol. 359, pp. 31-46.

He et al., "Perception threshold and electrode position for spinal cord stimulation", Pain, vol. 59, (1994), pp. 55-63.

Herreras, "Local Field Potentials: Myths and Misunderstandings", Frontiers in Neural Circuits, Dec. 15, 2016, vol. 10, Article 1101, 16 pgs., doi:10.3389/fncir.2016.00101.

Holsheimer et al., "Optimum Electrode Geometry for Spinal Cord Stimulation: the Narrow Bipole and Tripole", Medical and Biological Engineering and Computing, 1997, vol. 35, No. 5, pp. 493-497.

Holsheimer et al., "Significance of the Spinal Cord Position in Spinal Cord Stimulation", Acta Neurochir (1995) [Suppl] 64: pp. 119-124.

Holsheimer et al., "Spinal Geometry and Paresthesia Coverage in Spinal Cord Stimulation", Neuromodulation, 1998, vol. 1, No. 3, pp. 129-136.

Huff, Terry B. et al., "Real-Time CARS Imaging Reveals a Calpain-Dependent Pathway for Paranodal Myelin Retraction during High-Frequency Stimulation", PLoS ONE, vol. 6, issue 3 (Mar. 3, 2011): e17176, 11 pgs., doi:10.1371/journal.pone.0017176.

Jeffrey et al., "A reliable method for intracranial electrode implantation and chronic electrical stimulation in the mouse brain", BMC Neuroscience. Biomed Central, London, GB, vol. 14, No. 1, Aug. 6, 2013, pp. 1-8.

Kent et al., "Instrumentation to Record Evoked Potentials for Closed-Loop Control of Deep Brain Stimulation", Conf. Proc. IEEE Eng. Med Biol. Sol, Aug. 2012, pp. 6777-6780, doi:10.1109/IEMBS.20113.6091671.

Kent et al., AR "Recording evoked potentials during deep brain stimulation: development and validation of instrumentation to suppress the stimulus artefact", J Neural Eng., Jun. 2012, vol. 9, No. 3, 036004, doi: 10.1088/1741-2560/9/3/036004.

Kim et al., "A Wavelet-Based Method for Action Potential Detection From Extracellular Neural Signal Recording With Low Signal-to-Noise Ratio", IEEE Transactions on Biomedical Engineering, Aug. 2003, vol. 50. No. 8, pp. 999-1011.

Kim et al., "Cell Type-specific Changes of the Membrane Properties of Peripherally-axotomized Dorsal Root Ganglion Neurons in a Rat Model of Neuropathic Pain", Neuroscience, vol. 86, No. 1, May 21, 1998, pp. 301-309, doi:10.1016/S0306-4522(98)00022-0.

Kopelman et al., "Attempted Reversible Sympathetic Ganglion Block by an Implantable Neurostimulator", Interactive CardioVascular and Thoracic Surgery, Feb. 7, 2012, vol. 14, Issue 5, pp. 605-609, doi:10.1093/icvts/ivr137.

Krames et al., "Neuromodulation", 1st Edition, Academic Press, 2009, pp. 540-541.

Krarup, Christian "Compound sensory action potential in normal and pathological human nerves", Muscle & Nerve, Apr. 2004, vol. 29, No. 4, pp. 465-483.

Krishnan et al., "Excitability Differences in Lower-Limb Motor Axons During and After Ischemia", Muscle & nerve, vol. 31, No. 2 (2005), pp. 205-213.

Kumar et al., "Deep Brain Stimulation for Intractable Pain: a 15-Year Experience", Neurosurgery, Apr. 1997, vol. 40, No. 4, pp. 736-747.

Kumar et al., "Double-blind evaluation of subthalamic nucleus deep brain stimulation in advanced Parkinson's disease", by the American Academy of Neurology, 51, No. 3, Sep. 1, 1998, pp. 850-855.

Kumar et al., "Globus Pallidus Deep Brain Stimulation for Generalized Dystonia: Clinical and PET Investigation", Neurology, Sep. 11, 1999, vol. 53, No. 4, pp. 871-874, doi:10.1212/WNL.53.4.871.

Laird et al., "A Model of Evoked Potentials in Spinal Cord Stimulation", IEEE Engineering in Medicine & Biology Society, 35th Annual Conference. Osaka, Japan: Jul. 3-7, 2013, pp. 6555-6558.

Lempka, Scott "The Electrode-Tissue Interface During Recording and Stimulation in the Central Nervous System", Thesis, 155 pgs., published May 2010.

Levy et al., "Incidence and Avoidance of Neurologic Complications with Paddle Type Spinal Cord Stimulation Leads", Neuromodulation, Sep. 2011, vol. 14, No. 15, pp. 412-422, https://doi.org/10.1111/j.1525-1403.2011.00395.x.

Li, S. et al., "Resonant antidromic cortical circuit activation as a consequence of high-frequency subthalamic deep-brain stimulation", J Neurophysiol. Dec. 2007; 98(6), pp. 3525-3537, First published Oct. 10, 2007. doi:10.1152/jn.00808.2007.

Ma et al., "Similar Electrophysiological Changes in Axotomized and Neighboring Intact Dorsal Root Ganglion Neurons", Journal of Neurophysiology 89, No. 3 (Mar. 1, 2003): 1588-1602, doi:10.1152/jn.00855.2002.

Macefield, "Spontaneous and Evoked Ectopic Discharges Recorded from Single Human Axons", Muscle & Nerve 21, No. 4, Apr. 1998, pp. 461-468.

Mahnam et al., "Measurement of the current-distance relationship using a novel refractory interaction technique", J. Neural Eng. 6(2): 036005, published May 20, 2009, 22 pgs.

Markandey, Vishal "ECG Implementation on the TMS320C5515 DSP Medical Development Kit (MDK)", Texas Instruments Application Report Jun. 2010, 35 pgs.

Extended European Search Report for European Application 18910394.8 Search Completed Oct. 7, 2021, dated Oct. 15, 2021, 8 pgs.

Extended European Search Report for European Application No. 16802238.2, dated Jan. 14, 2022, 7 Pgs.

Extended European Search Report for European Application No. 19793420.1, Search completed Dec. 6, 2021, dated Dec. 17, 2021, 9 Pgs.

International Search Report and Written Opinion for International Application No. PCT/AU2020/050725, Search completed Oct. 19, 2020, dated Oct. 19, 2020, 8 Pgs.

Parker et al., "Electrically evoked compound action potential recording in peripheral nerves", Bioeletron. Med., vol. 1, No. 1, 2018, pp. 71-83, ISSN 2059-1500.

Australian Examination Report for Application No. 2019283936, dated Apr. 1, 2021, 7 pages.

International Search Report for International Application No. PCT/AU2019/051151, International Filing Date Oct. 22, 2019, Search Completed Feb. 24, 2020, dated Feb. 24, 2020, 9 pgs.

International Search Report for International Application No. PCT/AU2019/051160, International Filing Date Oct. 23, 2019, Search Completed Jan. 28, 2020, dated Jan. 28, 2020, 13 pgs.

International Search Report for International Application No. PCT/AU2019/051163, International Filing Date Oct. 23, 2019, Search Completed Jan. 21, 2020, dated Jan. 31, 2020, 8 pgs.

(56) References Cited

OTHER PUBLICATIONS

International Search Report for International Application No. PCT/AU2019/051197, International Filing Date Oct. 30, 2019, Search Completed Jan. 21, 2020, dated Jan. 21, 2020, 15 pgs.
International Search Report for International Application No. PCT/AU2019/051210, International Filing Date Nov. 2, 2019, Search Completed Feb. 4, 2020, dated Feb. 4, 2020, 10 pgs.
Japanese Office Action for Application No. 2018-552138, dated Mar. 1, 2021, 7 pages with English translation.
"Evoke 12C Percutaneous Leads", Saluda Medical, specifications available in the "Evoke Surgical Guide", version 6, http://www.saludamedical.com/manuals/, retrieved May 2017.
Bratta et al., "Orderly Stimulation of Skeletal Muscle Motor Units with Tripolar Nerve Cuff Electrode", IEEE Transactions on Biomedical Engineering, vol. 36, No. 8, 1989.
Celestin et al., "Pretreatment Psychosocial Variables as Predictors of Outcomes Following Lumbar Surgery and Spinal Cord Stimulation: A Systematic Review and Literature Synthesis", American Academy of Pain Medicine, 2009, vol. 10, No. 4, pp. 639-653. doi:10.1111/j.1526-4637.2009.00632.X.
Cong et al., "A 32-channel modular bi-directional neural interface system with embedded DSP for closed-loop operation", 40th European Solid State Circuits Conference (ESSCIRC), 2014, pp. 99-102.
Connolly et al., "Towards a platform for prototyping control systems for optimization of neuromodulation therapies", IEEE Biomedical Circuits and Systems Conference (BioCAS), 2015, pp. 1-4.
Delgado et al., "Measurement and interpretation of electrokinetic phenomena", Pure Appl. Chem., 2005, vol. 77, No. 10, pp. 1753-1805.
Fitzpatrick et al., "A Nerve Cuff Design for the Selective Activation and Blocking of Myelinated Nerve Fibers", IEEE Engineering in Medicine and Biology Society, vol. 13, No. 2, 1991.
Howell et al., "Evaluation of Intradural Stimulation Efficiency and Selectivity in a Computational Model of Spinal Cord Stimulation", PLOS ONE, DOI:10.1371/journal.pone.0114938, Dec. 23, 2014.
Jones et al., "Scaling of Electrode-Electrolyte Interface Model Parameters In Phosphate Buffered Saline", IEEE Transactions on Biomedical Circuits and Systems, 2015, vol. 9, No. 3, pp. 441-448.
North et al., "Prognostic value of psychological testing in patients undergoing spinal cord stimulation: a prospective study", Neurosurgery, Aug. 1, 1996, vol. 39, Issue 2, pp. 301-311. https://doi.org/10.1097/00006123-199608000-00013.
Peterson et al., "Stimulation artifact rejection in closed-loop, distributed neural interfaces", ESSCIRC, 42nd European Solid-State Circuits Conference, Lausanne, 2016, pp. 233-235.
Rijkhoff et al., "Acute Animal Studies on the Use of Anodal Block to Reduce Urethral Resistance in Sacral Root Stimulation", IEEE Transactions on Rehabilitation Engineering, vol. 2, No. 2, 1994.
Rijkhoff et al., "Orderly Recruitment of Motoneurons in an Acute Rabbit Model", Annual International Conference of the IEEE Engineering in Medicine and Biology Society, vol. 20, No. 5, 1998.
Scott et al., "Compact Nonlinear Model of an Implantable Electrode Array for Spinal Cord Stimulation (SCS)", IEEE Transactions on Biomedical Circuits and Systems, 2014, vol. 8, No. 3, pp. 382-390.
Stanslaski et al., "Design and Validation of a Fully Implantable, Chronic, Closed-Loop Neuromodulation Device with Concurrent Sensing and Stimulation", IEEE Transactions on Neural Systems and Rehabilitation Engineering, Jul. 2012, Date of Publication: Jan. 23, 2012, vol. 20, No. 4, pp. 410-421, DOI: 10.1109/TNSRE.2012.2183617.
Zhou et al., "A High Input Impedance Low Noise Integrated Front-End Amplifier for Neural Monitoring", IEEE Transactions on Biomedical Circuits and Systems, 2016, vol. 10, No. 6, pp. 1079-1086.
International Search Report and Written Opinion for International Application No. PCT/AU2019/051385, Search completed Mar. 24, 2020, dated Mar. 24, 2020, 8 Pgs.
Abrard et al., "A time-frequency blindsignal separation methodapplicable to underdetermined mixtures of dependent sources", Signal Processing 85 (2005) 1389-1403.
Casey et al., "Separation of Mixed Audio Sources by Independent Subspace Analysis", Mitsubishi Electric Research Laboratories (2001).
Jang et al, "Single Channel Signal Separation Using Time-Domain Basis Functions", IEEE Signal Processing Letters, Jun. 2003, vol. 10, No. 6.
Jang et al., "A Maximum Likelihood Approach to Single-channel Source Separation", Journal of Machine Learning Research 4 (2003) 1365-1392.
Laird-Wah, "Improving Spinal Cord Stimulation: Model-Based Approaches to Evoked Response Telemetry", UNSW, Aug. 2015.
Mannan et al., "Identification and Removal of Physiological Artifacts From Electroencephalogram Signals: A Review", IEEE Access, May 31, 2018, vol. 6, pp. 30630-30652, https://doi.org/10.1109/ACCESS.2018.2842082.
Niazy et al., "Removal of FMRI environment artifacts from EEG data using optimal basis sets", NeuroImage 28 (2005) 720-737.
Takahashi et al, "Classification of neuronal activities from tetrode recordings using independent component analysis", Neurocomputing, (2002), vol. 49, Issues 1-4, 289-298.
Zhang et al., "Automatic Artifact Removal from Electroencephalogram Data Based on a Priori Artifact Information", BioMed research international. 2015. 720450. Aug. 25, 2015 DOI: https://doi.org/10.1155/2015/720450.
Kent, "Characterization of Evoked Potentials During Deep Brain Stimulation in the Thalamus", Dissertation, Duke University. Retrieved from https://hdl.handle.net/10161/8195, 2013.
Communication Pursuant to Article 94(3) EPC, for European Patent Application No. 14861553.7, dated Nov. 4, 2022, 8 Pgs.
Extended European Search Report for European Application 19876581.0 Search Completed Jun. 7, 2022, dated Jun. 15, 2022, 7 pgs.
Extended European Search Report for European Application No. 19875139.8, Search completed Jun. 7, 2022, dated Jun. 15, 2022, 8 Pgs.
Extended European Search Report for European Application No. 19899138.2, Search completed Jul. 26, 2022, dated Aug. 3, 2022, 09 Pgs.
International Search Report and Written Opinion for International Application No. PCT/AU2021/050043, Search completed Mar. 29, 2021, dated Mar. 29, 2021, 11 Pgs.
Abraira et al., "The Cellular and Synaptic Architecture of the Mechanosensory Dorsal Horn", Cell 168, Jan. 12, 2017, 295-310.
Islam et al., "Methods for artifact detection and removal from scalp EEG: A review", Neurophysiologie Clinique—Clinical Neurophysiology, vol. 46, No. 4, pp. 287-305, XP029804850, ISSN: 0987-7053, DOI: 10.1016/J.NEUCLI.2016.07.002, 2016.
Li et al., "Therapeutic Deep Brain Stimulation in Parkinsonian Rats Directly Influences Motor Cortex", Neuron, vol. 76, No. 5, pp. 1030-1041, XP0289601 09, ISSN: 0896-6273, 001: 10.1 016/J.NEURON.2012.09.032, 2012.
Shepherd et al., "Electrical stimulation of the auditory nerve: II. Effect of stimulus waveshape on single fibre response properties", Hearing Research, 1999, 130, 171-188.

\* cited by examiner

Figure 11a
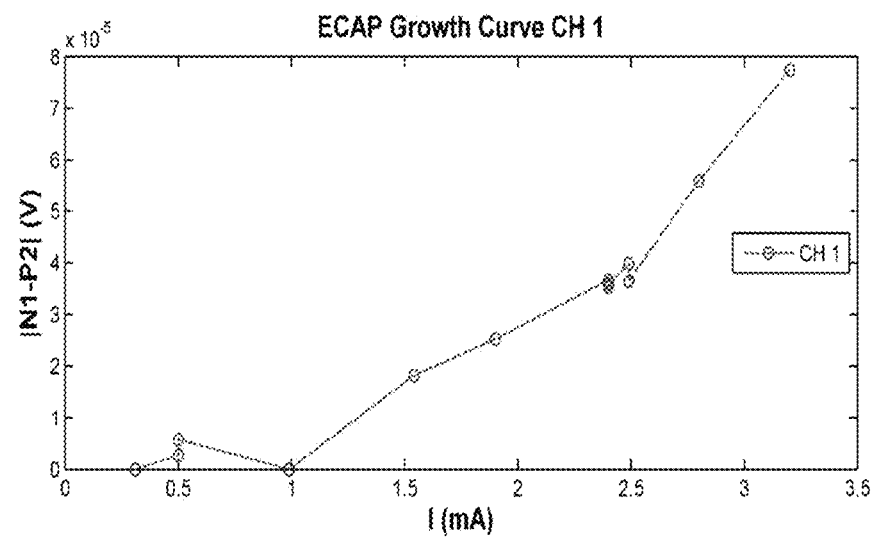
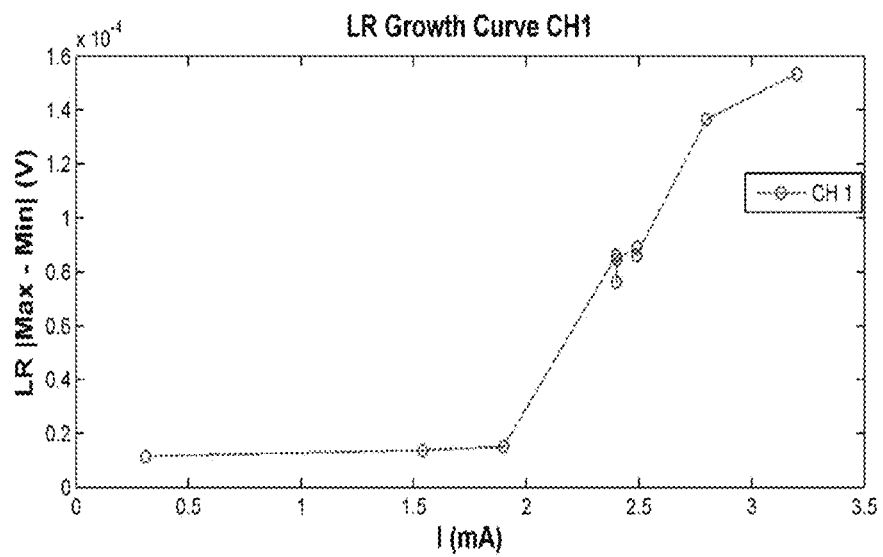
Figure 11b

NEUROSTIMULATION OF MIXED NERVES

CROSS-REFERENCE TO RELATED APPLICATIONS

This application is a national stage of Application No. PCT/AU2019/050384, filed Apr. 29, 2019, which claims the benefit of Australian Provisional Patent Application No. 2018901410 filed Apr. 27, 2018, which is incorporated herein by reference.

TECHNICAL FIELD

The present invention relates to neuromodulation delivered to mixed nerve fibres comprising multiple fibre types, and in particular to a method and device for assessing recruitment of a desired subset of the fibre types from electrophysiological response measurements.

BACKGROUND OF THE INVENTION

There are a range of situations in which it is desirable to apply electrical stimuli to a nerve in order to give rise to a compound action potential (CAP). A neuromodulation system applies an electrical pulse to tissue in order to generate a therapeutic effect. Such a system typically comprises an implanted electrical pulse generator, and a power source such as a battery that may be rechargeable by transcutaneous inductive transfer. An electrode array is connected to the pulse generator, and is positioned adjacent the target neural pathway(s). An electrical pulse applied to the neural pathway by an electrode causes the depolarisation of neurons, and generation of propagating action potentials.

Almost all applications of neuromodulation are applied to nerves containing more than one type of fibre (referred to herein as a "mixed nerve"). It is often the case that a large proportion of the fibres of a mixed nerve, when stimulated, do not produce an effect that is directly and immediately perceivable by the subject or an outside observer (such as a surgeon or clinician). For example, stimulation of fibres of the autonomic nervous system is often not perceptible by the subject.

A control problem, facing neuromodulation systems of all types, is achieving neural recruitment at a sufficient level required for therapeutic effect, but at minimal expenditure of energy. The power consumption of the stimulation paradigm employed has a direct effect on battery requirements which in turn affects the device's physical size and lifetime. For rechargeable systems, increased power consumption results in more frequent charging and, given that batteries only permit a limited number of charging cycles, ultimately this reduces the implanted lifetime of the device.

One example of neuromodulation of a mixed nerve is sacral nerve stimulation (SNS), in which stimulation frequencies are typically low (<20 Hz) and the charge can be quite high (for example, each stimulus may comprise a current of up to 7 mA or more, at pulse widths of 210 us). SNS has been shown to be therapeutically effective for faecal incontinence (FI), Urinary Retention (UR), Urinary Urge Incontinence (UUI, also referred to as overactive bladder (OAB)), intractable constipation, and chronic pelvic pain, with further indications likely.

The mechanisms of SNS are still poorly understood and various theories have been proposed. For existing sacral nerve neuromodulators, following implantation the process of adjusting the stimulus amplitude and frequency is a trial and error procedure, with muscle contractions in the form of the motor response of the pelvic floor, anal sphincter, and/or the toe being used as a proxy for therapeutic efficacy. In this testing method the stimulus amplitude is turned up until a muscle response is visually sighted intraoperatively. The amplitude is then reduced below sensation threshold and set to that level for ongoing operation, but how much reduction is adequate to avoid undesirable motor responses or paraesthesia while still maintaining appropriate therapeutic effect is poorly known. This method relies on a theory that SNS acts to re-establish sphincter control through stimulation of the efferent motor fibres, or via an afferent reflex arc. One theory is that SNS induces a reflex inhibitory effect on the detrusor muscle of the urinary bladder through afferent and efferent fibres in the sacral nerves. Another proposed mechanism, especially for genitourinary disorders is via inhibition of bladder contractions via afferent or central mechanisms.

To have a SNS device operating continuously at amplitude levels just below the muscle or paraesthesia recruitment threshold involves a considerable power drain on the implant battery.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed before the priority date of each claim of this application.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

In this specification, a statement that an element may be "at least one of" a list of options is to be understood that the element may be any one of the listed options, or may be any combination of two or more of the listed options.

SUMMARY OF THE INVENTION

According to a first aspect, the present invention provides a method of neurostimulation of a mixed nerve comprising a plurality of nerve fibre types, the method comprising:

positioning an implantable electrode array proximal to a mixed nerve comprising a plurality of nerve fibre types, the implantable electrode array comprising a plurality of electrodes;

delivering an electrical stimulus from at least one nominal stimulus electrode of the implantable electrode array, the electrical stimulus being delivered in accordance with a set of stimulus parameters;

obtaining from at least one nominal recording electrode of the implantable electrode array a recording of the electrophysiological response evoked by the electrical stimulus;

analysing the recording of the electrophysiological response by assessing one or more selected characteristics of the recording, and identifying from the observed selected characteristics a level of recruitment of one or more fibre types recruited by the electrical stimulus; and refining the stimulus parameters in a manner to effect selective recruitment of one or more fibre types relative to other fibre types of the mixed nerve.

According to a second aspect, the present invention provides a non-transitory computer readable medium for neurostimulation of a mixed nerve comprising a plurality of nerve fibre types, comprising instructions which, when executed by one or more processors, causes performance of the following:

delivering an electrical stimulus from at least one nominal stimulus electrode of an implantable electrode array proximal to a mixed nerve comprising a plurality of nerve fibre types, the implantable electrode array comprising a plurality of electrodes, the electrical stimulus being delivered in accordance with a set of stimulus parameters;

obtaining from at least one nominal recording electrode of the implantable electrode array a recording of the electrophysiological response evoked by the electrical stimulus;

analysing the recording of the electrophysiological response by assessing one or more selected characteristics of the recording, and identifying from the observed selected characteristics a level of recruitment of at least a first fibre type recruited by the electrical stimulus; and refining the stimulus parameters in a manner to effect selective recruitment of one or more fibre types relative to other fibre types of the mixed nerve.

According to a third aspect the present invention provides a neurostimulation device comprising:

an implantable electrode array configured to be implanted proximal to a mixed nerve comprising a plurality of nerve fibre types, the implantable electrode array comprising a plurality of electrodes; and a control unit configured to deliver an electrical stimulus from at least one nominal stimulus electrode of the implantable electrode array, the electrical stimulus being delivered in accordance with a set of stimulus parameters; the control unit further configured to obtain from at least one nominal recording electrode of the implantable electrode array a recording of the electrophysiological response evoked by the electrical stimulus; the control unit further configured to analyse the recording of the electrophysiological response by assessing one or more selected characteristics of the recording, and identify from the observed selected characteristics a level of recruitment of one or more fibre types recruited by the electrical stimulus, and the control unit further configured to refine the stimulus parameters in a manner to effect selective recruitment of one or more fibre types relative to other fibre types of the mixed nerve.

Importantly, the present invention thus utilises one or more recordings of electrically evoked electrophysiological response(s) obtained from a nerve proximal to a stimulation site as a means to selectively deliver neurostimulation to a selected fibre type selected from a plurality of fibre types existing in the nerve.

Throughout this specification, the term "electrophysiological response" is to be understood as including one or more neural responses (CAPs), myoelectric responses (such as motor unit action potentials and compound muscle action potentials (CMAPs)), and/or interneuron activity (the firing of neurons that do not possess long axonal projections such as sensory fibres). A neural response evoked by an applied stimulus is also referred to herein as an evoked compound action potential (ECAP). In addition to a neural response, a recording of an electrophysiological response to a stimulus can also include myoelectric activity, also referred to in some instances herein as a late response.

Some embodiments of the present invention may additionally or alternatively be advantageous over past approaches which target for example activation of a particular muscle, or muscle group, such as the anal sphincter, such as by intraoperative observation of muscle activation for the purpose of assessing the proximity of the stimulus electrode to the mixed nerve. By seeking muscle activation alone, or a proxy thereof, as the goal of neurostimulation, such past approaches are blind as to which fibre types are recruited by the stimuli, so long as muscle activation is observed. In contrast to such past approaches, the present invention's approach of targeting one or more specific fibre types on the basis of observed electrophysiological response measurements avoids the obfuscating effect of the propagation of the stimulated neural response away from the stimulus site to a muscle, as such propagation typically passes a range of neural branches, synapses, terminations, and further involves muscle fibre activation by motor neurons, all of which results in muscle observations being at least partly blinded to the nature of the neural recruitment occurring at the stimulus site. Moreover the present invention's approach of targeting specific fibre types on the basis of observed electrophysiological response measurements further opens the possibility of, in some embodiments, delivering therapy on the basis of recruitment of fibres unrelated to muscle activation and thus wholly undetectable by muscle observations. For example neuromodulation of fibres of the autonomic nervous system may not be perceptible by the patient nor by external clinical observation. Such embodiments of the present invention thus recognise that in order to optimise neuromodulation of a mixed nerve, an objective measure of the recruited fibres needs to be used.

In some embodiments of the invention, the stimulus parameters which are refined to effect selective recruitment of one or more fibre types may comprise any one or more of: intraoperative electrode placement; intraoperative electrode array type selection, including lead, paddle or cuff array selection; stimulus frequency; stimulus amplitude; stimulus waveform; stimulus pulse width; stimulus electrode(s) selection, including interposition of a stimulus site between electrodes by way of current steering; stimulus shape (biphasic, triphasic, etc); stimulus polarity (monopolar, bipolar, tripolar, etc), stimulus electrode size, stimulus electrode shape, and the like.

In some embodiments of the invention, the stimulus parameters are refined in a manner to effect selective recruitment of one or more desired fibre types while further effecting selective non-recruitment or diminished recruitment of at least one non-selected fibre type.

The one or more selected characteristics of the recording from which the level of recruitment of at least the first fibre type recruited by the electrical stimulus is identified may comprise any one or more of: one or more ECAP inflexion points; one or more ECAP peak positions; one or more ECAP peak amplitudes; ECAP propagation velocity; propagation or non-propagation of an electrophysiological response as observed at a recording site; ECAP duration; refractory period; strength-duration curve characteristics including chronaxie or rheobase; growth curve characteristics including threshold and slope; number of ECAP peaks with increasing stimulus current; presence, amplitude and/or latency of a late response, amplitude and shape of the electrophysiological response with varying stimulus frequency.

For example, in embodiments where the selected characteristic is conduction velocity, the fibre type recruited may be determined from a priori knowledge of the linear relationship between the diameter of a myelinated fibre and the conduction velocity.

In embodiments where the selected characteristic is conduction velocity, the conduction velocity may be measured by determining a propagation time from the stimulus site to a single measurement electrode a known distance from the stimulus site. More preferably, the conduction velocity may be measured by observing a neural response at a first measurement electrode and at a second measurement electrode, and determining a propagation time between the first and second measurement electrodes. Determining conduction velocity from two or more measurement electrodes allows inspection of particular elements of the ECAP waveform, such as a peak arrival time or a zero crossing arrival time of the ECAP, improving accuracy of the conduction velocity determination and in turn improving accuracy of identification of the recruited fibre type.

In some embodiments of the present invention, with prior knowledge of the morphology of neural responses under different fibre distributions, models can be used to solve the reverse problem of retrieving the fibre distribution from one or more obtained recordings of electrophysiological responses evoked by electrically stimulating a mixed nerve. For example the teachings of the present Applicant's International Patent Publication No. WO2016161484 (PCT/AU2016/050263) relating to fibre distribution modelling may be applied to this purpose.

The selected characteristic may be determined by assessment of recordings obtained from two or more spaced apart measurement electrodes, the recordings being of a single electrophysiological response event. Obtaining spatially distinct recordings of the same electrophysiological response for example allows determination of whether, relative to the vicinity of the recording electrodes, the selected characteristics of the recordings are a propagating neural response upon the mixed nerve or a non-propagating response such as myoelectric activity in the far field of the electrodes, thereby assisting fibre type determination. While it is to be noted that recordings obtained in the close vicinity of an activated muscle will observe a propagating CMAP, present embodiments of the invention will typically utilise an electrode array implanted distally from affected muscles so that myoelectric activity will in such embodiments be observed as a non-propagating component of the recordings of the electrophysiological response.

In embodiments where the selected characteristic is a non-propagating characteristic of the recording, an existence of such a non-propagating component in the recording, such as a component arising 4-10 ms after stimulus, may be taken to arise from the myoelectric activity produced by the stimulus by, for example, stimulating motor neurons. The muscle activation may thus be deduced to arise from activation of Aα efferent fibres, which having a high conduction velocity may not be directly observable in the recordings, as Aα responses may have concluded at the recording electrode before the stimulus is complete or before stimulus artefact has settled sufficiently to permit direct observation of Aα fibre responses. However, selective Aα recruitment may be observed by reference to the non-propagating component arising 4-10 ms after stimulus in the recording (for SNS, at least). The amplitude of such a non-propagating component may thus be taken as a measure of the number of Aα fibres recruited, permitting selective recruitment of Aα fibres.

Further embodiments of the invention may provide for differentiation of a mode of activation of one or more recruited fibre types. For example, without intending to be limited by theory, it is noted that activation of Aα fibres may be the result of either direct activation by the electrical stimulus, or the result of indirect activation via a reflex arc such as the H-reflex elicited when stimulating Ia proprioceptive fibres. The mode of activation can be difficult to ascertain given that Ia fibres have substantially the same conduction velocity as Aα fibres and thus cannot be distinguished by this measure. However, it is further noted that with increasing stimulation frequency Aα fibre activation by the H-reflex will decline at relatively low frequencies such as at around 30 Hz stimulation rate, whereas direct Aα fibre activation does not decline until a higher stimulation frequency is reached. Accordingly, some embodiments of the invention may provide for identifying a mode of activation of one or more fibre types, by applying varied stimulation rates, identifying a threshold frequency above which activation declines, and determining from the threshold frequency a mode of activation.

In some embodiments the selected characteristic may comprise a propagating response arising in the recording less than 1 ms after the stimulus and/or having a conduction velocity in the range 80-120 m/s, taken to indicate activation of Aα fibres.

In some embodiments the selected characteristic may comprise a propagating response arising in the recording less than 6 ms after the stimulus and/or having a conduction velocity in the range 3-15 m/s, taken to indicate activation of B fibres.

In some embodiments the selected characteristic may comprise a propagating response arising in the recording less than 6 ms after the stimulus and/or having a conduction velocity in the range 0.5-2 m/s, and/or having a duration of over 10 ms, taken to indicate activation of C fibres.

In some embodiments the selected characteristic may comprise a propagating response arising in the recording within 3 ms after the stimulus and/or having a conduction velocity in the range 30-80 m/s, taken to indicate activation of Aβ fibres.

In some embodiments the selected characteristic may correspond to any fibre type of interest based on known characteristics of such a fibre type, as defined by any suitable fibre classification system.

In some embodiments, more than one selected characteristic of the recording of the electrophysiological response may be assessed in order to determine a level of recruitment of each of one or more fibre types recruited by the electrical stimulus. For example, a level of recruitment of motor fibres may be determined by reference to both an amplitude of a late response in the recording, and also by reference to whether the late response is non-propagating between multiple recording electrodes.

In some embodiments, two or more fibre types may be targeted for example for the purpose of more effectively treating a single condition, and/or to simultaneously treat two or more co-existing or comorbid conditions, for example where each fibre type is therapeutic in relation to a respective condition. For example, one of a sympathetic nerve fibre type and a parasympathetic nerve fibre type may be targeted to excite activity of a selected organ or body system at a first time, and the other of the sympathetic nerve fibre type and the parasympathetic nerve fibre type may be targeted to inhibit activity of the selected organ or body system at a second time.

A plurality of selected characteristics, or in some embodiments all of the above described selected characteristics, may be monitored in the recording(s) of the electrophysiological response(s). In some embodiments a machine learning classifier may be applied in order to classify observed electrophysiological responses by fibre type(s) present.

In some embodiments of the invention, the electrode array comprises a single implantable lead. In some embodiments of the invention, the electrode array comprises a plurality of electrode leads connected to a single implantable pulse generator (IPG).

In some embodiments of the invention, the at least one nominal recording electrode, and the at least one nominal stimulus electrode, are positioned adjacent to a single branch of the mixed nerve, being a segment of the mixed nerve in which no neural branching or neural merging occurs upon the nerve between the nominal recording electrode(s) and the nominal stimulus electrode(s).

In some embodiments of the invention, the nominal recording electrode(s) and the nominal stimulus electrode(s) are positioned less than 60 mm apart. In some embodiments of the invention, the nominal recording electrode(s) and the nominal stimulus electrode(s) are positioned less than 30 mm apart. In some embodiments of the invention, the nominal recording electrode(s) and the nominal stimulus electrode(s) are positioned less than 20 mm apart. Positioning the recording electrodes close to the stimulus site is advantageous in improving understanding of the recruitment of the one or more fibre types resulting from the stimulus, before the nerve response passes to another vertebral segment or passes a synapse or ganglion, for example.

A mixed nerve is defined herein as including a nerve comprising at least two fibre types. Fibre types are defined herein as fibres having distinct diameter, conduction velocity, myelination, efference or afference, nervous sub-system (e.g. sympathetic, parasympathetic) or other such distinguishable characteristic. For example the fibre types may be distinct based on comprising two or more of A$\alpha$, A$\beta$, A$\gamma$, A$\delta$, B, and C fibre types, or Ia, Ib, II, III and IV fibre types. The mixed nerve may comprise part of the central nervous system, or a part of the peripheral nervous system. The mixed nerve may comprise part of the somatic nervous system, or part of the autonomic nervous system, or both. The mixed nerve may be wholly afferent or wholly efferent, or may comprise both afferent and efferent fibres. The mixed nerve may comprise fibres which carry sensory information, motor information, or both. The mixed nerve may comprise fibres which are part of one or more of the sympathetic nervous system, the parasympathetic nervous system and the enteric nervous system.

It is further to be understood herein that the mixed nerve may comprise more than one nerve, such as a plurality of adjacent nerves comprising a plurality of nerve fibre types. Thus, some embodiments of the invention may comprise determining which nerve within a plurality of adjacent nerves contains the fibres that a given neuromodulation applications aims to stimulate. The plurality of adjacent nerves may comprise a nerve plexus, such as the sacral plexus or the brachial plexus. Electrode placement and stimulus parameters can in such embodiments then be adapted to optimally recruit the desired fibre types while minimising recruitment of undesired fibre types. For example, although generally consistent, the human anatomy can differ from person to person and some differences in innervation is common. While past approaches may operate for example on an anatomical assumption that a given site, such as the S3 foramen, is a most appropriate site for neuromodulation, the present invention instead provides for an objective determination of which stimulus site is most effectively recruiting one or more fibres types of interest, so that a location of stimulation may be refined accordingly. Such embodiments of the present invention therefore allow personalised therapies to be developed that take into consideration the subject's anatomy.

The mixed nerve may comprise the vagus nerve. In such embodiments the first fibre type preferentially recruited may comprise parasympathetic fibres, such as B fibres, to provide a therapy for a brain related condition such as refractory epilepsy or depression. Additionally or alternatively vagus nerve stimulation may be configured to preferentially recruit B fibres in order to serve a therapeutic effect in the periphery or viscera such as an anti-inflammatory effect, for example to influence the spleen to alter the immune response, such as to treat Crohn's disease or rheumatoid arthritis, or a condition of the liver.

Additionally or alternatively, in embodiments targeting the vagus nerve, the stimulation may be configured to reduce or avoid recruitment of any one or more of: A$\beta$ fibres to avoid tingling throat side effects; A$\alpha$ fibres to avoid hoarseness and voice alteration (difficulty speaking, dysphonia, etc) side effects; C fibres to avoid pain side effects, and A$\delta$ fibres to avoid pain side effects. Preferred embodiments selectively recruit each of these plurality of fibre types of the vagus nerve only to a degree which is therapeutic while avoiding or minimising side effects.

In some embodiments one or more fibre types of the vagus nerve may be targeted in order to treat one or more of: obesity, epilepsy, paced stomach (gastric reflux), pancreatitis, diabetes, inflammatory bowel disease, rheumatoid arthritis, Crohn's disease, fibromyalgia, other inflammatory disease, depression, sepsis, or pain (fibromyalgia, migraines).

In some embodiments one or more proprioceptive or motor fibre types of the dorsal roots and/or dorsal columns may be targeted in order to treat one or more of spasticity, Parkinson's disease, or other motor control disorders.

In some embodiments one or more fibre types may be targeted in order to treat a disorder of the autonomic nervous system, such as dysregulation of the bladder, the digestive system, the heart or the blood vessels.

In some embodiments one or more fibre types of the phrenic nerve may be targeted in order to treat a breathing disorder to induce paced diaphragm contractions.

In some embodiments one or more fibre types of the tibial nerve may be targeted in order to treat bladder control disorders.

In some embodiments one or more motor fibre types may be targeted through functional electrical stimulation in order to treat a motor control dysfunction or to effect rehabilitation.

In some embodiments the relative activation of the post-synaptic dorsal column pathway and the primary sensory afferents may be optimised in order to treat neuropathic pain.

The mixed nerve may in some embodiments comprise the sacral nerve. In such embodiments the first fibre type preferentially recruited may comprise parasympathetic fibres, or other fibre types. Sacral nerve stimulation may be provided to selected fibre types to provide a therapy for one or more of faecal incontinence (FI), Urinary Retention (UR), Urinary Urge Incontinence (UUI, also referred to as overactive bladder (OAB)), intractable constipation, and chronic pelvic pain.

The mixed nerve may in some embodiments comprise a preganglionic mixed nerve such as the vagus nerve, a ventral root, or the sacral nerve. Such embodiments are advantageous in permitting stimulation to occur at a site which is relatively easy to access, and at which relatively low stimulation intensity is required, while selectively recruiting only the fibres of interest. This is in contrast to past approaches targeting post-ganglionic C nerves which are difficult to access and which require high stimulus intensity.

In some embodiments the mixed nerve may comprise a root of a spinal nerve such as a ventral root. The ventral root may comprise motor fibres and parasympathetic fibres. The stimulation may in some embodiments be configured in order to preferentially recruit the motor fibres of the ventral root in order to directly activate motor neuron fibre(s) of interest.

The stimulation may in some embodiments be configured in order to preferentially recruit parasympathetic and/or sympathetic fibres of a preganglionic mixed nerve. Parasympathetic stimulation may be targeted to any one or more of the heart, larynx, trachea, bronchi, oesophagus, stomach, liver, pancreas, small intestine, spleen, large intestine or kidney, all originating from the 10th cranial nerve, also referred to as the vagus nerve. Parasympathetic stimulation may be targeted to any one or more of the large intestine, bladder, and genitalia all originating from the sacral segments of the spinal cord. Sympathetic nerve stimulation may be targeted to the heart and/or larynx by stimulating the sympathetic fibres in one or more of the ventral roots of thoracic segments T1-T4. Sympathetic nerve stimulation may be targeted to the stomach, liver, pancreas, adrenal gland, spleen, and/or small intestine by stimulating the sympathetic fibres in one or more of the ventral roots of thoracic segments T5-T12. Sympathetic nerve stimulation may be targeted to the kidney, bladder, genitalia, and/or lower intestine by stimulating the sympathetic fibres in one or more of the ventral roots of thoracic segments T11-T12 and the lumbar segments L1-L3. For example, some embodiments may provide sympathetic and parasympathetic stimulation of the liver by stimulating the sympathetic fibres in the thoracic ventral roots T5-T12 and the parasympathetic fibres originating in the vagus nerve.

In some embodiments of the invention refining the stimulus parameters comprises a clinical fitting process of stimulus parameters by clinician trial and error or the like. Refining the stimulus parameters may in some embodiments comprise intraoperative repositioning of the electrodes.

Refining the stimulus parameters in other embodiments may comprise an automated feedback process administered by a processor of the implanted device.

Some embodiments may spatially target the selected fibre type, by applying a supramaximal stimulus from a first electrode to recruit all fibres of the nerve, and observing the recruited responses at selected circumferential positions by using a selected electrode segment for recording at the selected circumferential position, analysing the recorded response to determine one or more fibre types which are adjacent to that position, and subsequently applying stimuli from the selected electrode segment at times when it is desired to recruit the one or more fibre types so identified. Other embodiments may spatially target the selected fibre type by using a selected electrode segment at a selected circumferential position to apply stimuli which are only just above a stimulus threshold to recruit fibres proximal to that segment, observing recruited responses at a second electrode, and analysing the recordings to determine the type of fibres being recruited by the stimuli from the selected electrode segment. Such embodiments may survey multiple electrode segments in this manner to determine the fibre type(s) adjacent to all such electrode segments. Other embodiments may apply equivalent spatial targeting by using electrodes which spatially differ other than in a circumferential manner, such as in a grid pattern or any other form of spatial electrode variations which permit distinct electrodes to recruit distinct subgroups of fibres.

In some embodiments the device is fully implantable and comprises an implantable pulse generator configured to deliver the stimuli via the stimulus electrodes, and to capture and analyse the recordings of the evoked electrophysiological responses to effect fibre type targeting. In alternative embodiments, the electrode array alone may be temporarily implantable, with an external control device effecting the fibre type targeting.

It is to be appreciated that a time of occurrence of electrophysiological responses in a recording is generally referred to herein by reference to an amount of time after the stimulus. However, this amount of time depends on both the conduction velocity of the fibre(s) being observed, and the distance of the respective recording electrode from the stimulus site. It is to be understood that time periods presented herein may be particularly applicable to a single implanted lead having recording electrodes spaced about 6 mm, 12 mm and 18 mm from the stimulus electrode. However, alternative electrode array geometries and configurations may provide electrodes at other distances from the stimulus site, and a simple calculation based on conduction velocity allows an alternative expected time of arrival of responses of each given fibre type to be determined, and such alternatives are within the scope of the present invention. Similarly, where a late response arising from far field activation of a muscle is a selected characteristic of interest, a time of occurrence of the late response will depend on a distance from the stimulus site to the muscle, and variations in a time of occurrence of such a late response are thus also simply determined from the stimulus site and associated anatomy, and such variations in the time of occurrence of the late response are within the scope of the present invention.

In some embodiments of the device of the third aspect of the invention the control unit is further configured to refine the stimulus parameters in a manner to effect selective recruitment of one or more fibre types relative to other fibre types of the mixed nerve. In some embodiments of the device of the third aspect of the invention the device is an implantable device, while in other embodiments the device may be an external device for trial or intraoperative use.

BRIEF DESCRIPTION OF THE DRAWINGS

An example of the invention will now be described with reference to the accompanying drawings, in which:

FIG. 11a illustrates measurements of the growth curve of the neural Aβ response of the same human SNS patient as FIG. 10. FIG. 11b illustrates measurements of the late response growth curve.

DESCRIPTION OF THE PREFERRED EMBODIMENTS

Figure 1:
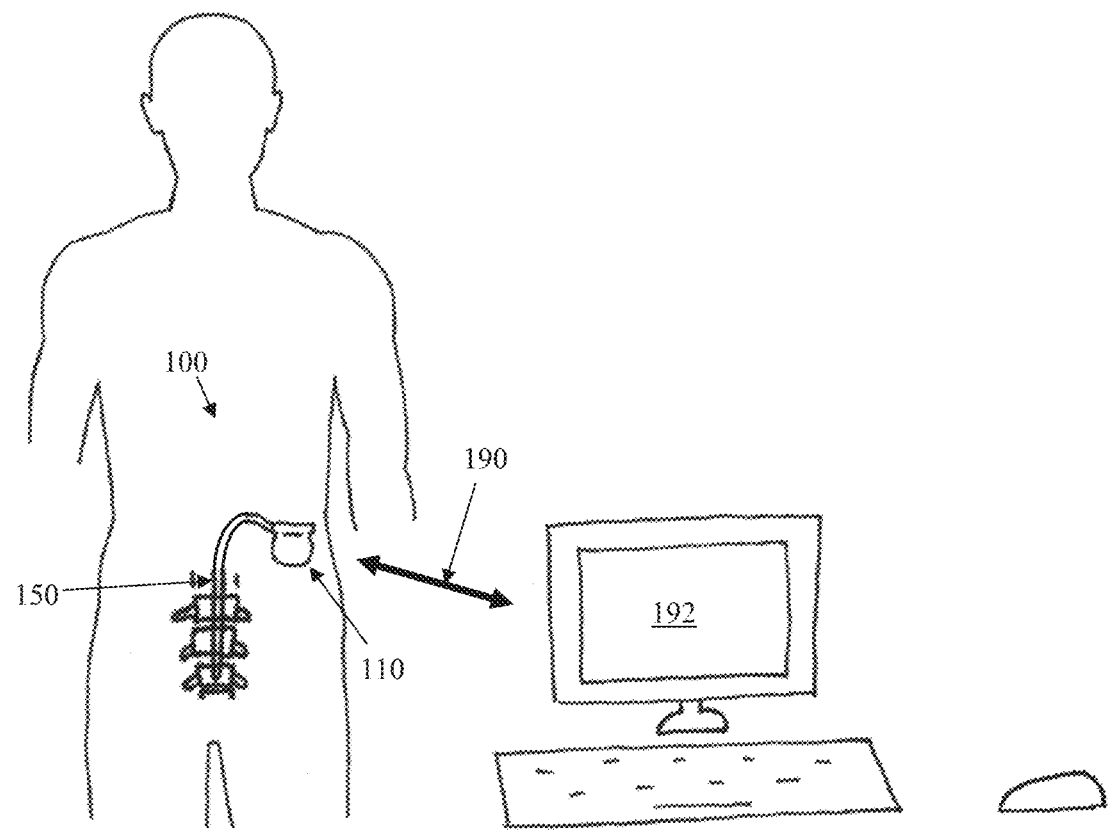
FIG. 1 schematically illustrates an implanted sacral nerve stimulator.

FIG. 1 schematically illustrates an implanted sacral nerve stimulator 100. Stimulator 100 comprises an electronics module 110 implanted at a suitable location in the patient's lower abdominal area or posterior superior gluteal region, and an electrode assembly 150 implanted within the sacrum and connected to the module 110 by a suitable lead. Numerous aspects of operation of implanted neural device 100 are reconfigurable by an external control device 192. Moreover, implanted neural device 100 serves a data gathering role, with gathered data being communicated to external device 192.

Figure 2:
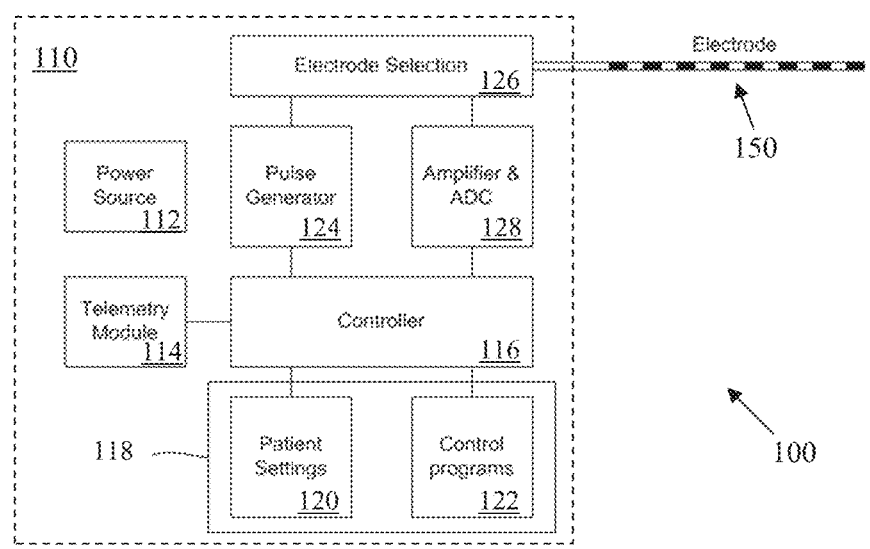
FIG. 2 is a block diagram of the implanted neurostimulator.

FIG. 2 is a block diagram of the implanted neurostimulator 100. Module 110 contains a battery 112 and a telemetry module 114. In embodiments of the present invention, any suitable type of transcutaneous communication 190, such as infrared (IR), electromagnetic, capacitive and inductive transfer, may be used by telemetry module 114 to transfer power and/or data between an external device 192 and the electronics module 110.

Module controller 116 has an associated memory 118 storing patient settings 120, control programs 122 and the like. Controller 116 controls a pulse generator 124 to generate stimuli in the form of current pulses in accordance with the patient settings 120 and control programs 122. Electrode selection module 126 switches the generated pulses to the appropriate electrode(s) of electrode array 150, for delivery of the current pulse to the tissue surrounding the selected electrode(s). Other electrode arrays may also be provided and may be similarly addressed by electrode selection module 126, for example as in the case of FIGS. 5 and 6, discussed further below. Thus, one or more electrodes of array 150 may be selected to serve as nominal stimulus electrodes at a given time, while one or more electrodes of the array 150 may be selected to serve as nominal sense electrodes at a given time, even though the electrodes may be physically the same and may serve a different role at other times. Measurement circuitry 128 is configured to capture measurements of neural responses sensed at sense electrode(s) of the electrode array as selected by electrode selection module 126. Such measurements will often comprise differential measurements between two sense electrodes upon array 150. However the measurements may additionally or alternatively be obtained from a single sense electrode of array 150 electrically referenced to a reference electrode upon a case of the module 110, or referenced to a system ground of the controller 116, for example. The sense electrodes are also referred to herein as recording electrodes.

Figure 3:
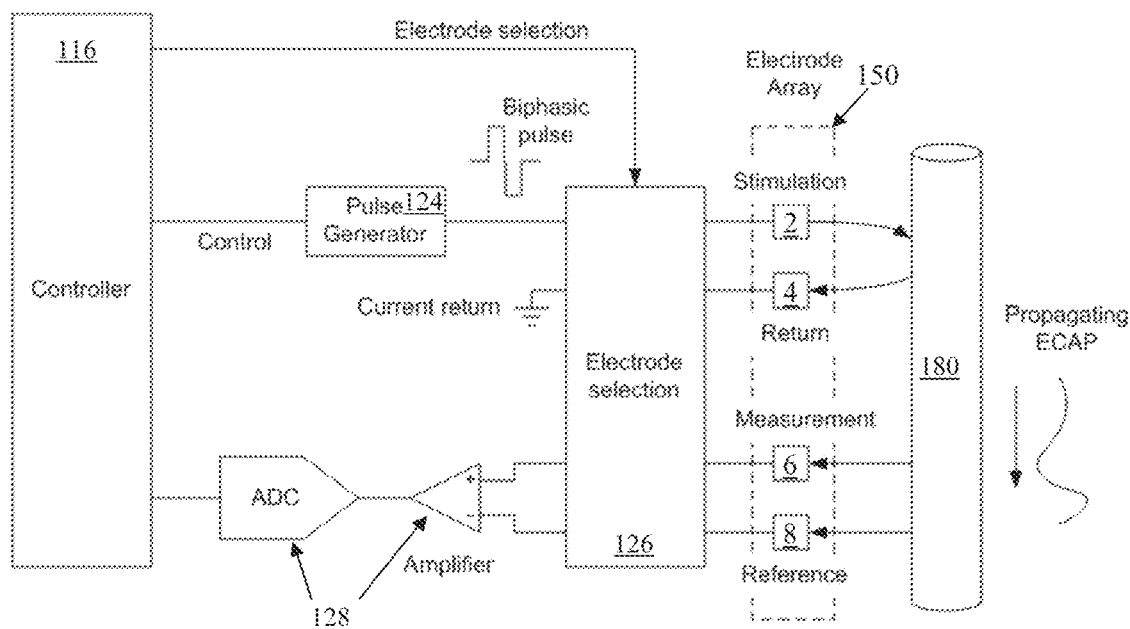
FIG. 3 is a schematic illustrating interaction of the implanted stimulator with a nerve.

FIG. 3 is a schematic illustrating interaction of the implanted stimulator 100 with a nerve 180, in this case the sacral nerve however alternative embodiments may be positioned adjacent any desired neural tissue including a peripheral nerve, visceral nerve, spinal nerve or a brain structure. Electrode selection module 126 selects a stimulation electrode 2 of electrode array 150 to deliver an electrical current pulse to surrounding tissue including nerve 180, and also selects a return electrode 4 of the array 150 for stimulus current recovery to maintain a zero net charge transfer.

Delivery of an appropriate stimulus to the nerve 180 evokes a neural response comprising a compound action potential which will propagate along the nerve 180 as illustrated, for therapeutic purposes which in the case of a sacral nerve stimulator might be to stimulate motor function of desired muscle fibres of the detrusor. To this end the stimulus electrodes are used to deliver stimuli at <20 Hz.

The device 100 is further configured to sense the existence and intensity of compound action potentials (CAPs) propagating along nerve 180, whether such CAPs are evoked by the stimulus from electrodes 2 and 4, or otherwise evoked. To this end, any electrodes of the array 150 may be selected by the electrode selection module 126 to serve as measurement electrode 6 and measurement reference electrode 8. Signals sensed by the measurement electrodes 6 and 8 are passed to measurement circuitry 128, which for example may operate in accordance with the teachings of International Patent Application Publication No. WO2012155183 by the present applicant, the content of which is incorporated herein by reference.

Figure 4:
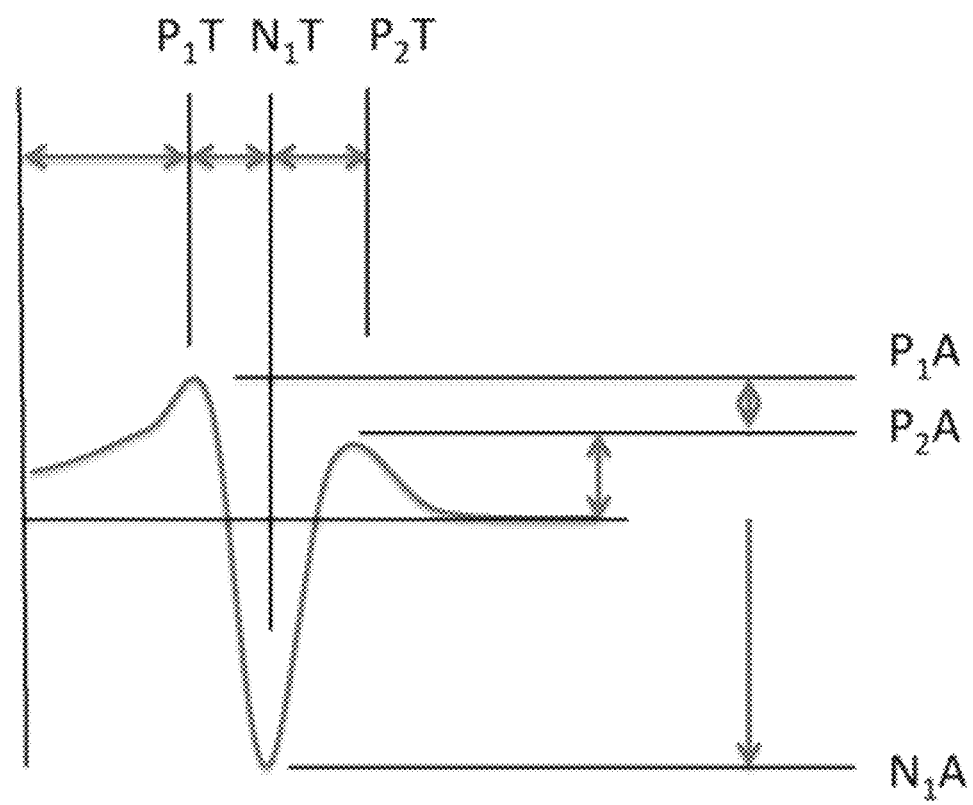
FIG. 4 illustrates the typical form of an electrically evoked compound action potential (ECAP) of a healthy subject.

FIG. 4 illustrates the typical form of an electrically evoked compound action potential (ECAP) when comprised of the contributions from action potentials of recruited fibres with similar properties. The shape and duration of the compound action potential shown in FIG. 4 is predictable because it is a result of the ion currents produced by the ensemble of axons generating action potentials in response to stimulation. The action potentials generated among a large number of fibres sum to form a compound action potential (CAP). The CAP is the sum of responses from a large number of single fibre action potentials. The CAP recorded is the result of a large number of different fibres depolarising. The propagation velocity of the action potential on each fibre is determined largely by the diameter of that fibre. The CAP generated from the firing of a group of similar fibres is measured as a positive peak potential P1, then a negative peak N1, followed by a second positive peak P2. This is caused by the region of activation passing the recording electrode as the action potentials propagate along the individual fibres. An observed electrically evoked CAP signal from Aβ fibres will typically have a maximum amplitude in the range of microvolts and a duration of 2-3 ms.

The CAP profile takes a typical form and can be characterised by any suitable parameter(s) of which some are indicated in FIG. 4. Depending on the polarity of recording, a normal recorded profile may take an inverse form to that shown in FIG. 4, i.e. having two negative peaks N1 and N2, and one positive peak P1.

In almost all neuromodulation applications, a single class of fibre response is desired, but the stimuli can recruit action potentials on other classes of fibres which cause unwanted side effects. Moreover, the difficulty of recording evoked neural responses has led to conventional solutions using proxy indicators such as observations of muscle contractions, without any knowledge of actual fibre type recruitment.

Figure 8A:
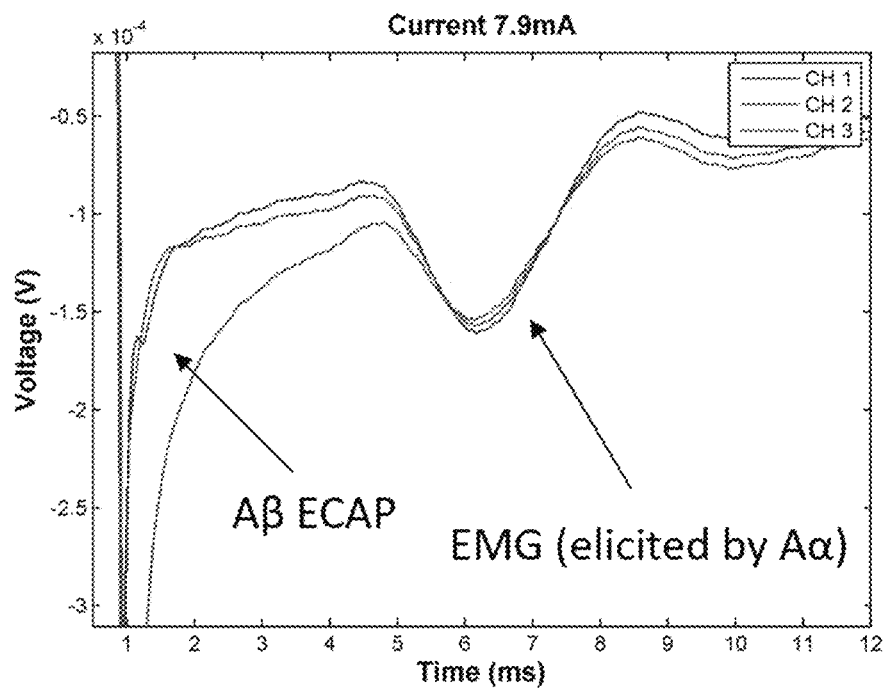
FIGS. 8a and 8b show electrophysiological responses obtained from the S3 sacral nerves of 2 human patients undergoing SNS therapy, from differing recording electrodes along the lead
Figure 8B:
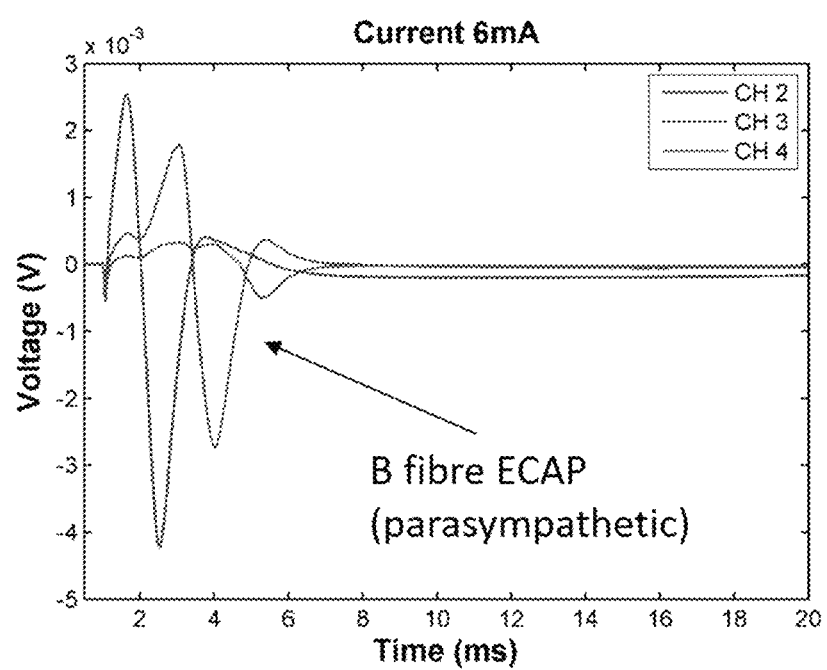

In accordance with the present embodiment, the CAP evoked by a given stimulus can be characterised by the parameters of the inflexion points in the curves of FIG. 4, FIG. 8a or FIG. 8b, for example. The positions and amplitudes of the peaks can be used alone or in combination to generate a correlation between them and the state and severity of a CNS disorder. Other electrophysiological data can be used to supplement the ECAP data. For instance, masker-probe studies can be used to determine the refractory period and the relative refractory period. The measurement of refractory periods allows an estimate of the frequency response of the fibres being stimulated. In particular, a shorter refractory period correlates with higher conduction velocity, thus allowing a determination of which fibre type(s) was/were recruited to give rise to the observed ECAP, and can thus provide a guide for setting stimulation frequency parameters. All these neurophysiological properties can be used to identify the stimulated nerves and can be used to guide fibre type targeting and stimulus parameter selection.

Almost all major nerves in the periphery are of mixed nature, meaning that the nerve contains fibres of various types and functions that run together. The peripheral nerves bundle together at various stages and form the spinal nerves (such as the S3 nerve, which is the main target for SNS). Before joining the spinal cord, the spinal nerves split up into the ventral and dorsal roots. In simplified terms, the ventral roots contain mostly a variety of efferent fibres, and the dorsal roots contain mostly a variety of afferent fibres. Mixed nerves therefore can contain both afferent and efferent axons. Another example of a mixed nerve is the vagus nerve (VN) which contains motor fibres, sympathetic fibres, parasympathetic fibres, and sensory fibres.

Figure 5:
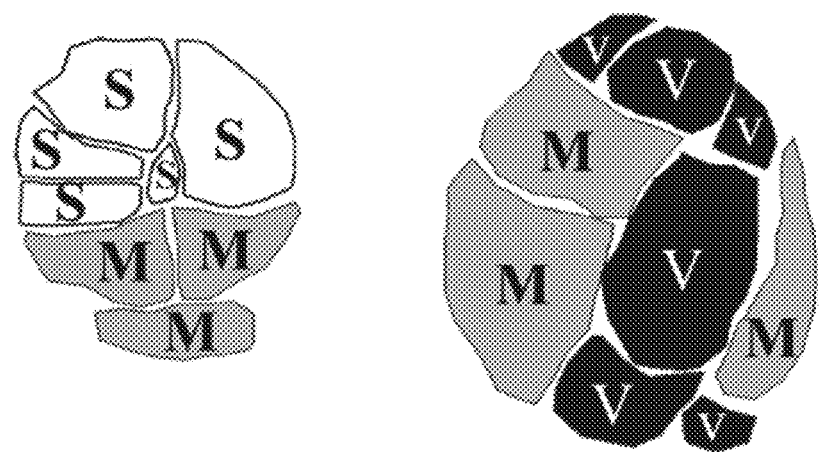
FIG. 5 is a schematic representation of the functional separation of fibres in the ventral rootlets of a human S2 nerve in cross-section.

Mixed nerves are heterogenous collections of fascicles, and it has been shown that the fascicles bundle nerve fibres that serve similar functions and share common physiological properties. This separation of function can be observed from the rootlets which form the dorsal and ventral roots of each spinal nerve. FIG. 5 is a schematic representation of the functional separation of fibres in the ventral rootlets of a human S2 nerve in cross-section. The root consists of 2 rootlets. Three different nerve distribution patterns arise: the somatic type (S) with predominant large, thickly myelinated fibres and absence of parasympathetic fibres; the vegetative type (V) with abundance of parasympathetic fibres; and the mixed type (M). Note the topographic aggregation of the fascicles of vegetative and somatic types. The fascicles with predominance of parasympathetic fibres are concentrated in the right rootlet of either root. In contrast, purely somatic fascicles are found in the left rootlets. It appears that the nerve fibres do not simply follow a random distribution, but rather some sort of functional organization.

Stimulation of any given subsection of a mixed nerve, for example by applying stimuli only from one side of the nerve at an amplitude which only recruits fibres in fascicles proximal to the stimulus electrode, will therefore activate a particular portion of fibres that serve a distinct function. The present invention recognises that targeting the appropriate fibres of a mixed nerve is of great importance for many neuromodulation applications.

Figure 6:
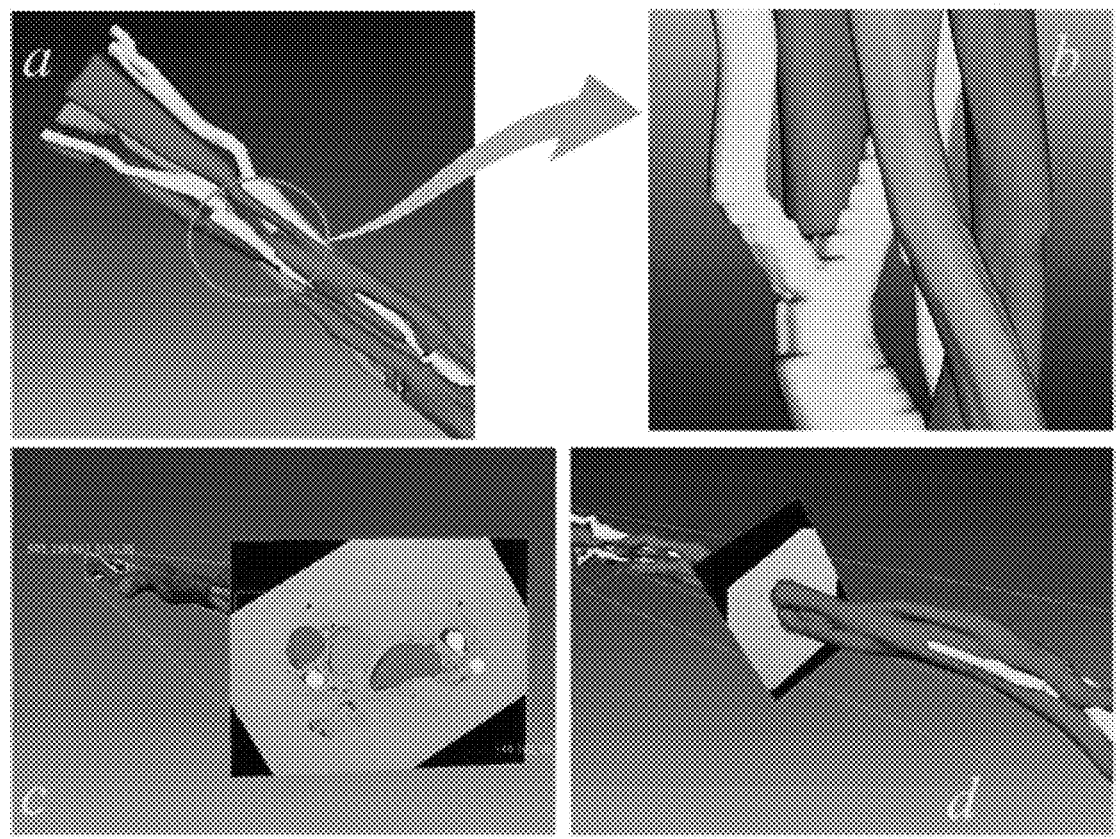
FIG. 6, which is a three-dimensional (3D) reconstruction of median nerve fascicles.

However, such targeting is in essence impossible from a purely anatomical approach, because the course of each fascicle in a mixed nerve varies along the nerve. The fascicles can cross, merge, and split. An example of this from the median nerve is given in FIG. 6, which is a three-dimensional (3D) reconstruction of median nerve fascicles. FIG. 6a is a 3D model of a median nerve at an arbitrary position, showing some changing patterns of different functional fascicles. Green represents motor nerve fascicles, yellow represents sensory nerve fascicles, and purple represents mixed (sensory and motor) nerve fascicles. FIG. 6b is an enlarged partial view of FIG. 6a, while FIG. 6c presents one transverse cross section image.

FIG. 6 demonstrates that fibre type targeting is difficult to address based only on anatomy because a desired fibre type takes significantly varying positions within the nerve at different parts of the nerve. Further, inter-patient variability of the content and disposition of fascicles within a nerve exists. These changes occur on scales which are significantly smaller than a typical neurostimulation electrode spacing, as typical implanted electrode arrays utilise electrodes which are 3 mm long, and are 4 mm apart from each other, i.e. positioned on a 7 mm pitch. However, in the space of 7 mm along the nerve shown in FIG. 6, any given nerve fascicle could take any or all positions within the bundle making it impossible to selectively target that fascicle based on surrounding anatomical orientations. Simplistically utilising smaller electrodes would not resolve these uncertainties.

Nevertheless, the present invention recognises that nerve fibres can be classified based on their physiological properties, such as myelination state and diameter. These properties result in differences in electrophysiological properties that allow the classification of stimulated nerve fibres through measures of, among others, the conduction velocity of the generated action potentials, their refractory period, and their strength-duration curves. For example, a linear relationship exists between the diameter of a myelinated fibre and the conduction velocity. A range of nerve fibre type classification systems exist, however regardless of nomenclature or classification used throughout this document, it is to be understood that it is the measures of differences in electrophysiological properties which permit differentiation of fibre types in accordance with the present invention, irrespective of nomenclature.

Figure 7:
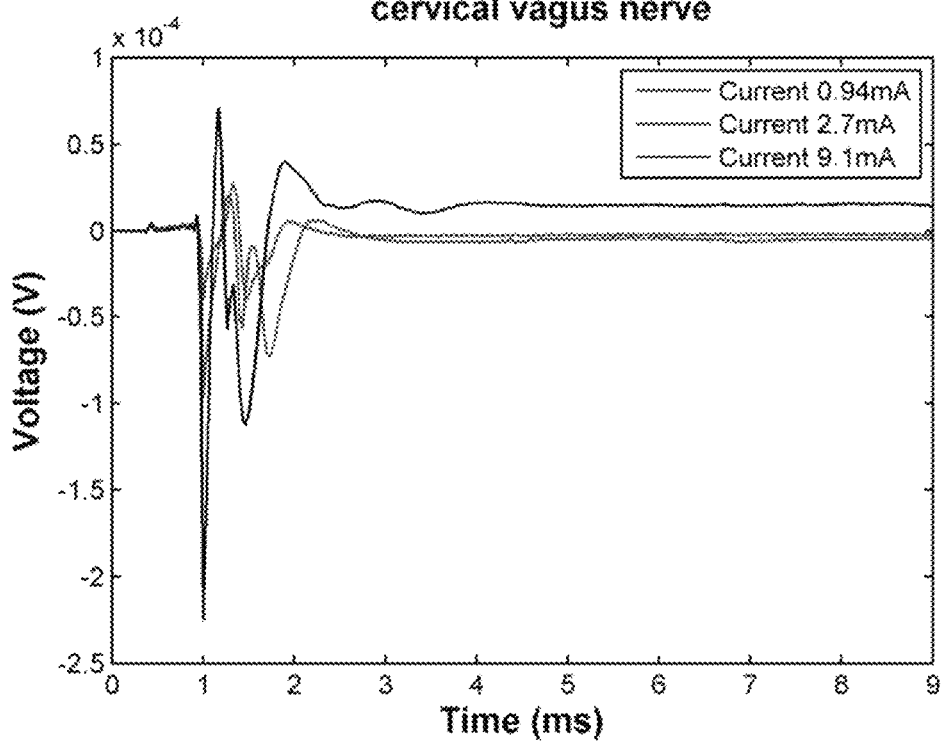
FIG. 7 shows the neural responses recorded from the cervical vagus nerve of a pig from a recording cuff electrode, at varying stimulus amplitude

FIG. 7 shows the neural responses recorded from the cervical vagus nerve of a pig from a recording cuff electrode which was located about 25 mm away from the stimulating cuff electrode around the same nerve, for various currents.

FIGS. 8a and 8b show electrophysiological responses obtained from the S3 sacral nerves of 2 human patients undergoing SNS therapy. Although the electrodes were placed using the same surgical technique for each human patient, the observed responses were markedly different between FIG. 8a and FIG. 8b. The sacral responses of FIGS. 8a and 8b were obtained by stimulating from standard cylindrical electrodes therefore preferentially activating the fibres on the side of the nerve which was in closest proximity with the electrode. Note that in FIGS. 8a and 8b the three channels recorded denoted CHn, were obtained from consecutive electrodes along the lead with increasing distance from the stimulus electrode on the same lead (6 mm, 12 mm and 18 mm from stimulus, respectively), so that neural responses propagating as action potentials along a nerve occur later in time on the channels from more distal recording electrodes, whereas non-propagating signals are not spaced apart in time across the respective channels, allowing the present invention to distinguish neural responses from other electrophysiological activity. Note also that in FIG. 8a electrode 4 was used for stimulation, so that CH3 was closest to the stimulus site and CH1 was furthest from the stimulus site, in contrast to FIG. 8b in which electrode 1 was used for stimulation so that CH2 was closest to the stimulus site and CH4 was furthest from the stimulus site. The response amplitude in FIG. 8b is noted to be tens of times larger than that of FIG. 8a, despite a slightly smaller stimulus. Such variation is common in practice and may well be attributed to differences in the position of each respective electrode array relative to the nerve. The large amplitude responses in FIG. 8b illustrate how much power saving can be achieved by applying the present invention in order to reduce the stimulus as much as possible to the minimum level where the desired therapeutic effect is achieved, which may also have a further benefit of avoiding inappropriately high recruitment levels which may be painful, injurious, or could cause unwanted side effects.

In contrast the vagal responses of FIG. 7 were obtained by stimulating from cuff electrodes surrounding the nerve, so that all fibre types were recruited based on their thresholds independently of their location around the circumference of the nerve. This difference in recruitment based on nerve fascicle position explains the difference in the responses obtained from the vagus and the sacral nerves as seen when comparing FIG. 7 on the one hand to FIGS. 8a and 8b on the other hand.

In particular, in FIG. 7, at low currents only larger fibre types are recruited and the observed ECAP exhibits few peaks. As the current is increased, smaller fibres are recruited and the resulting ECAP starts to display additional peaks, in addition to the expected increase in peak amplitude.

On the other hand in FIG. 8a we observe an Aβ ECAP in the timeframe around 1-2 ms, and a myoelectric response. The ECAP in the timeframe around 1-2 ms can be specifically identified as an Aβ ECAP because of the conduction velocity and the distance of each respective recording electrode from the stimulus site. Further, the signal component observed in the timeframe around 4-10 ms can be specifically associated with an Aα response (either from direct activation or via a reflex arc by means of for example Ia fibre activation). While the fast conduction velocity of the Aα response mean that this neural response itself is obscured in the very early part of the recording (e.g. in the period <1 ms), the existence of an Aα response can nevertheless be noted because of the existence of the non-propagating signal component observed in the timeframe around 4-10 ms, which is an electrical field resulting from muscle activation and which therefore must arise due to Aα activation as this is the role of Aα fibres. In FIG. 8b we observe B fibres (most likely preganglionic parasympathetic efferents) dominating the response, and again this observed component of the recording can be specifically identified as a B fibre response because of the observed conduction velocity of the response past the three spaced recording electrodes being used. Although therefore likely to be B fibres, the responses could also stem from Aδ fibres, and it is again to be noted that the nomenclature used is not taken to be limiting to the fibre type differentiation enabled by the present invention.

The sympathetic and parasympathetic systems serve complementary roles in the modulation of visceral function. As a rule of thumb, the parasympathetic fibres are responsible for "rest or digest" response whereas the sympathetic fibres are responsible for "fight or flight" response. In the case of micturition for example, parasympathetic nerves excite the bladder and relax the urethra, whereas the sympathetic fibres inhibit the bladder body and excite the bladder base and urethra. In the case of bladder innervation, the preganglionic sympathetic fibres exit the spinal cord in the ventral roots at the rostral lumbar segments, the preganglionic parasympathetic fibres exit the spinal cord through the ventral roots of the sacral nerves. Accordingly, in some embodiments the present invention recognises that selectively targeting these fibre types may be of utility in therapy for incontinence, in contrast to prior approaches of targeting remote muscle responses as a proxy for therapy. Such embodiments of the invention may thus provide techniques for measuring evoked compound action potentials (ECAPs) from the sacral nerve to improve SNS both by better targeting the appropriate nerves, and by applying closed-loop stimulation in chronic implants based on the ECAP observations.

Figure 9:
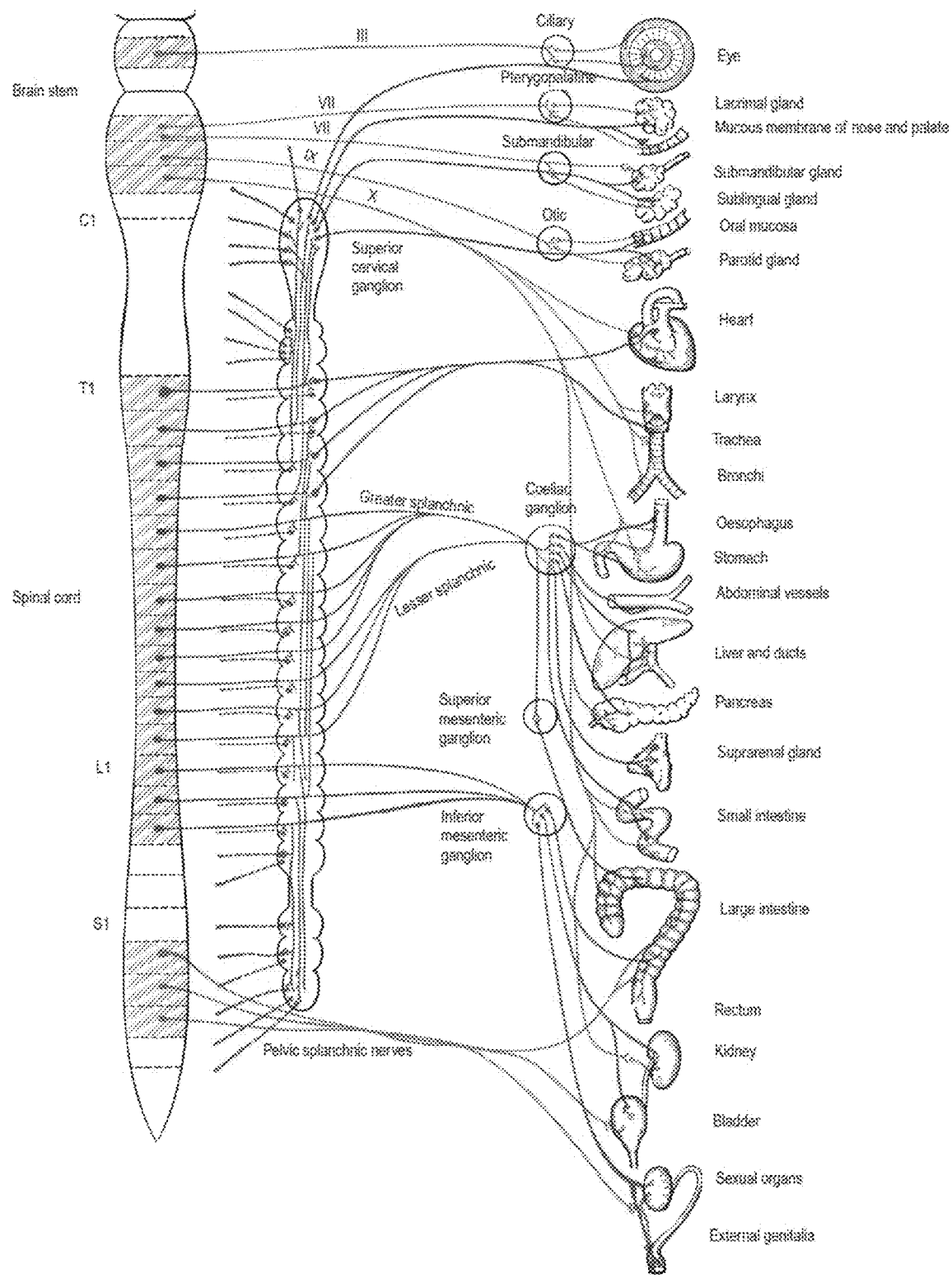
FIG. 9 illustrates sympathetic and parasympathetic nerve pathways which form part of mixed nerve neural pathways upon which the approach of the present invention may be applied.

More generally, other embodiments of the invention may apply a similar targeted approach to neuromodulation upon any mixed nerve of the body in order to provide therapy for dysfunction associated with any such nerve. FIG. 9 illustrates a multiplicity of such sympathetic (red) and parasympathetic (blue) efferent pathways, which form part of mixed nerves upon which the approach of the present invention may be applied. The interrupted red lines indicate postganglionic rami to the cranial and spinal nerves.

Note that parasympathetic innervation of the heart, larynx, oesophagus, stomach, liver, pancreas, intestine, and kidney all originate from the 10th cranial nerve, also referred to as the vagus nerve. Parasympathetic innervation of the intestine, bladder, and genitalia originates from the sacral segments of the spinal cord. Note that the upper and lower parts of the large intestine are innervated from different parts, the upper part from the vagus nerve, the lower part from the sacral nerves.

The sacral nerve is a mixed nerve containing the full spectrum of fibre types and functions. It contains C fibres as well as myelinated fibres ranging from B (parasympathetic) to Aα motor neurons and carries both afferent as well as efferent neural signals. The sacral nerve is not homogenous and is made up of rootlets, further subdivided into fascicles, which preserve some degree of functional separation of the fibre types.

Nerve fibres are classified by their function as well as their physical properties (mostly myelination state and fibre diameter). It is important to note that this separation of physical properties and function is not absolute, and neural signals of a variety of functions are carried via fibres of similar properties (there are more functions than there are classes of fibres). As a rule of thumb, the diameter of myelinated fibres (in μm) is correlated to the conduction velocity (in m/s) by a factor of about 6. Thanks to this property, it is possible to use ECAPs measured from SNS electrodes to determine conduction velocity, and in turn to determine which fibres are being recruited by the stimulation paradigm. This can improve the therapy on 2 levels: aetiology-specific targeting of the appropriate nerves as well as closed-loop feedback control to maintain a stable therapy and improve effectiveness.

As the sacral nerves are non-homogeneous mixed nerves, the location of the lead with respect to the nerve fibres plays a large role in determining which fibre types are activated by SNS. Without intending to be being limited by theory, the recordings of the electrophysiological response made from SNS electrodes can differentiate whether muscle efferents, sensory afferents, somatic afferents and efferents, parasympathetic fibres, or C fibres are being activated. Both the ECAP properties as well as the late response properties can be used to determine which fibres are activated by the stimulation.

For example, in FIG. 8a the presence of a non-propagating late response indicates activation of Aα efferents (either directly or indirectly), and the presence of an Aβ response indicates sensory fibres are activated. In FIG. 8b, the presence of a B fibre response can indicate the activation of parasympathetic fibres. Due to the segmented nature of the sacral nerve (separation into fascicles in which bundles of fibres with similar function are clustered), the responses observed from SNS are not homogeneous (see FIG. 8). Further, inter-patient variability in the sacral plexus likely leads to variations in fibre types present in each sacral nerve.

Figure 10A:
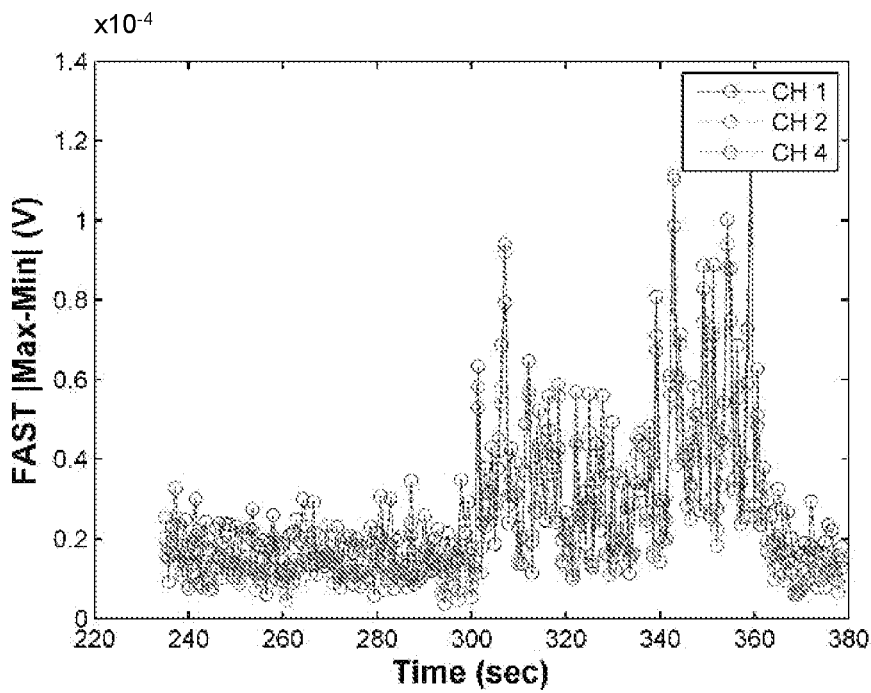
FIGS. 10a and 10b illustrate changes in amplitude of the Aβ response, and changes in amplitude of the late response, respectively, over time.
Figure 10B:
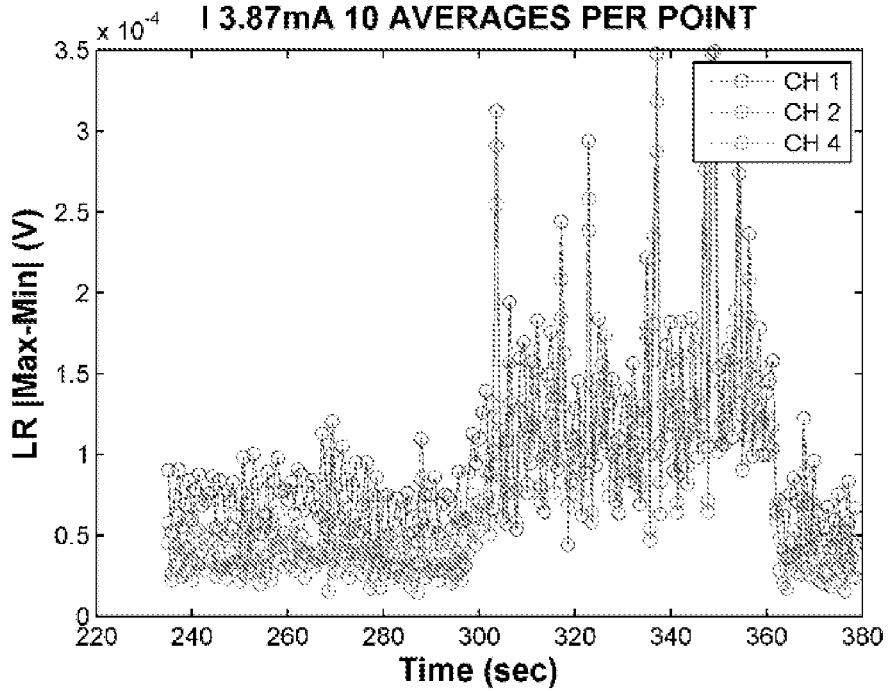

Independently of the type of response observed with SNS, changes in the patient's body posture as well as internal mechanisms that cause a movement of the electrode with respect to the nerve are reflected in a change in the amplitude of the neural response. FIG. 10a illustrates changes in amplitude of the Aβ response (example in FIG. 8a around 1-2 ms), denoted FAST in FIG. 10a. FIG. 10b illustrates changes in amplitude of the myoelectric response (example in FIG. 8a around 4-10 ms), denoted LR in FIG. 10b. This data was obtained for a patient undergoing a SNS trial in the S3 sacral nerve root. The patient was sitting at the beginning of the experiment of FIG. 10, stood up at around 300 seconds, and sat back down at around 360 seconds. The increase in amplitude of the neural responses, which approximately doubled from sitting to standing, was felt as an increase in paraesthesia sensation by the patient. A similar increase in amplitude was observed in the myoelectric response.

FIG. 11a illustrates measurements of the growth curve of the neural Aβ response of the same human SNS patient as FIG. 10. FIG. 11b illustrates measurements of the myoelectric response growth curve. The growth curve herein refers to measures of electrophysiological response amplitude in response to increasing stimulus intensity. Where a recording of an electrophysiological response comprises multiple components, such as comprising both an ECAP and a myoelectric response, separate growth curves of each such component may be obtained. Both the Aβ response of FIG. 11a and the myoelectric response of FIG. 11b display threshold behaviour, in that for the application of stimuli at current levels below a certain threshold, no response arises. The threshold in FIG. 11a by inspection appears around 1.5 mA, while the threshold in FIG. 11b by inspection appears at around 2 mA. Above the respective threshold each growth curve exhibits a linear section in which linearly increasing the stimulus current leads to an approximately linear increase in both the neural Aβ response and the myoelectric response. Both curves are expected to plateau at higher stimulus amplitudes as maximum recruitment is achieved, however these higher stimulus values were not applied in this experiment as it would have been painful to the patient. FIG. 11 thus illustrates that the myoelectric and Aβ responses each have a linear part which can be separately or jointly exploited by a feedback loop operating within the respective linear range shown in FIG. 11.

Figure 11C:
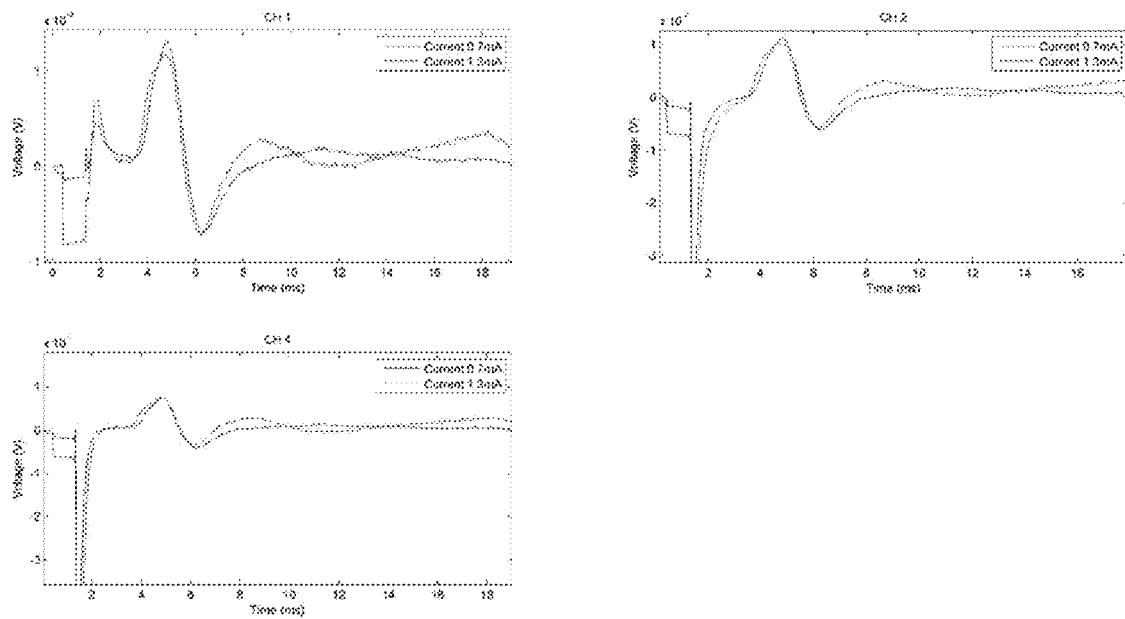
FIG. 11c illustrates recordings from a human patient.
Figure 11D:
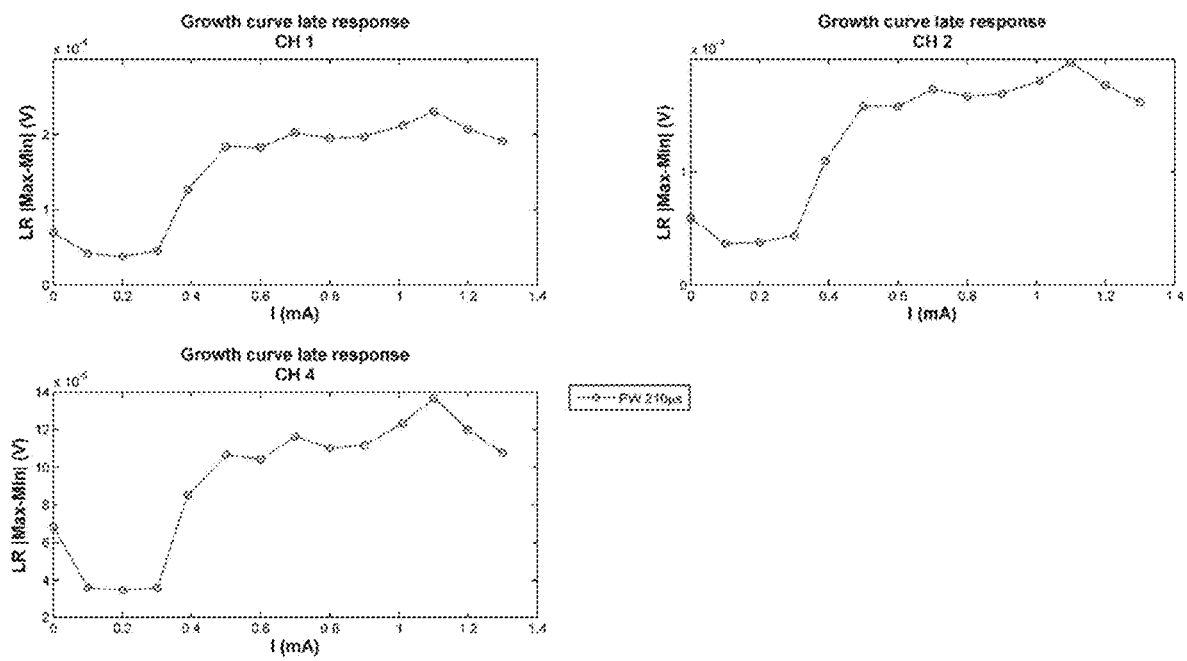
FIG. 11d shows the growth curve for the late response.

FIG. 11c illustrates recordings from a human patient treated for urinary incontinence with S3 sacral nerve stimulation. Clear late responses are visible on all recording channels CH1, CH2 and CH4, during the time period around 3-10 ms, at both 0.7 mA stimulation and 1.3 mA stimulation. A fast response (ECAP) is not visible in these recordings as the stimulus pulse width obscures the ECAP. FIG. 11d shows the growth curve for the late response amplitude in response to increasing stimulus amplitude, as measured at each respective recording electrode. As seen in FIG. 11d, this is an example of a plateauing myoelectric response.

Figure 11E:
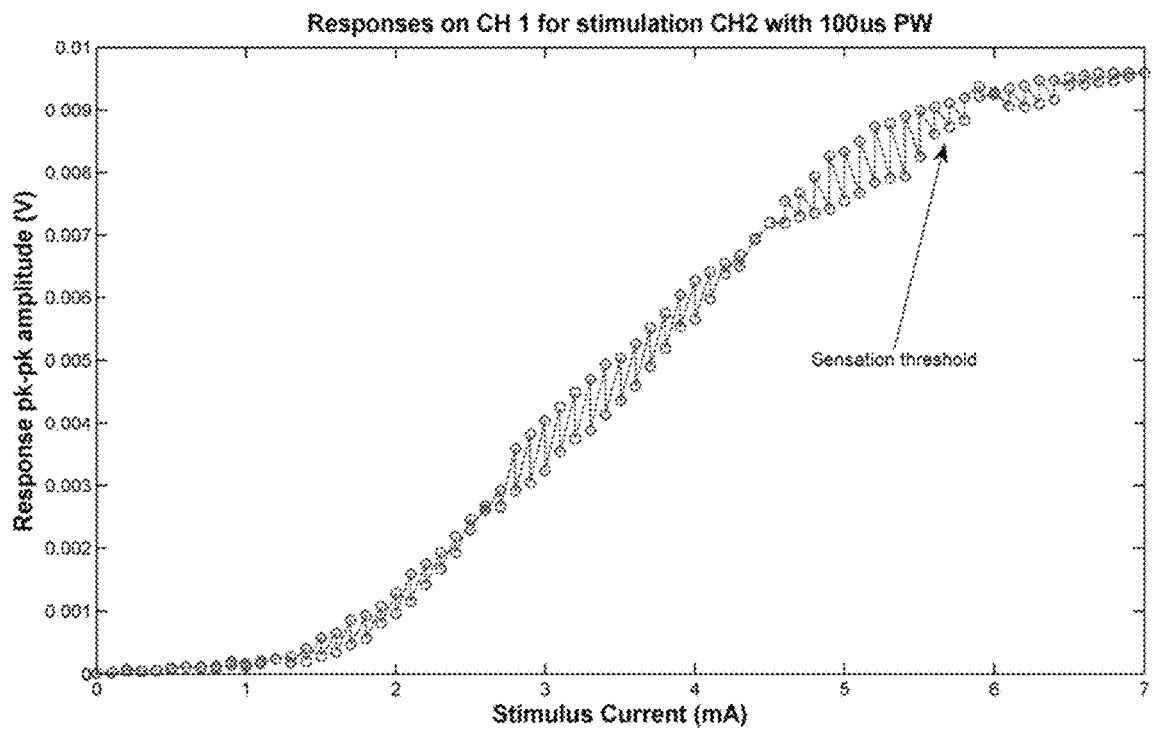
FIG. 11e shows the growth curve of a B fibre response in one patient with an arrow marking the current threshold for stimulus perception.

Such recordings enable a useful range of stimulation to be ascertained, as no therapeutic benefit occurs below the threshold, and no additional fibres are recruited beyond the plateau in the growth curve. FIG. 11e is a plot of a plateauing growth curve for a slow response thought to be a B fibre response. Indicated on the curve is the part of the growth curve at which the patient started to feel the stimulation. Notably, this patient threshold was at the plateau of this B fibre response, meaning that the slow B fibre response observed in FIG. 11e was not linked to sensation, and that a first fibre type was recruited without recruiting others.

Some embodiments may further provide for staged fibre targeting, whereby in a first stage of operation a level of recruitment of a desired fibre type is monitored and maintained within a desired range of the curve of FIGS. 11a, 11b or 11e, and wherein a second stage of operation is adopted when recruitment or observation of the desired fibre type is lost (as can be common with postural changes or lead migration), in which a recruitment of a secondary fibre type is instead monitored and maintained within a desired range so as to ensure continued neural recruitment in general even when recruitment of the selected fibre type in particular becomes untraceable. An alternative response to a loss of recruitment or observation of the desired fibre type may be to trigger any other suitable event, such as a warning signal or an automatic reprogramming procedure. Additionally, linearity testing may be undertaken in response to a loss of recruitment or observation of the desired fibre type, whereby the stimulation amplitude is varied to explore whether the recruitment responds linearly; absence of a linear response of recruitment to such stimulus amplitude variations may indicate a loss of therapeutic efficacy which may be used to trigger reprogramming or a warning signal or the like.

Figure 12:
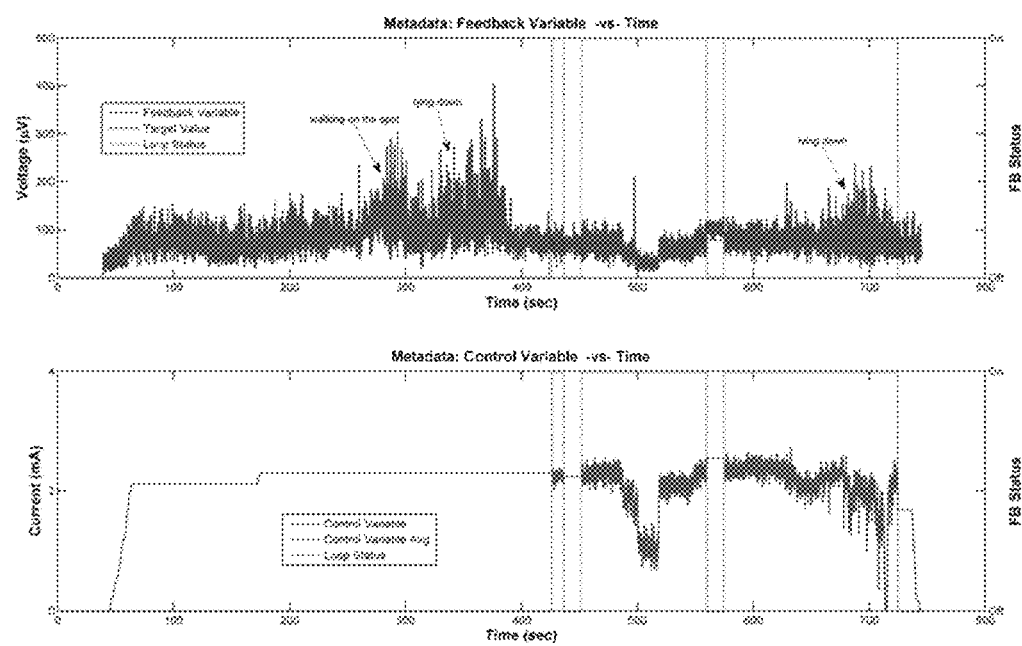
FIG. 12 illustrates changes in the amplitude of myoelectric responses observed in a human SNS patient over time.

As noted in relation to FIG. 8b, it is also possible to identify recruitment of, and selectively target recruitment of, B fibres of the autonomic nervous system. The myoelectric response may similarly be targeted. FIG. 12 illustrates changes in the amplitude of myoelectric responses observed in a human SNS patient over time (upper trace), together with the associated control variable (lower trace) over a period of time covering both open and closed loop modes. FIG. 12 thus illustrates successful closed loop control based on a myoelectric response.

Equipped with these insights, embodiments of the invention may thus provide for aetiology specific fibre targeting in a mixed nerve. For example, in the case of SNS, instead of relying on past approaches utilising muscle responses without knowledge of fibre types recruited, targeting and programming can be performed using the invention. Aetiology specific fibre targeting in a mixed nerve recognises that in most cases when stimulating a mixed nerve, only a subset of fibres are relevant to the condition being treated by stimulation. Stimulating all fibres of the mixed nerve will inevitably lead to unwanted side effects or inefficient stimulation.

In the broadest sense, these particular embodiments optimise neuromodulation therapy on a mixed nerve by using electrophysiological measurements to selectively target a subset of fibre types in a mixed nerve. This will consist in optimising the stimulus parameters such that the responses of desired fibre types are obtained whilst minimising the responses of unwanted fibre types. In the ideal case, only the desired fibres will be activated by the device, although in many embodiments simply achieving preferential targeting of the desired fibre type(s) and/or preferentially minimising recruitment of other fibre types may nevertheless deliver the benefits of the present invention.

In one embodiment, this invention proposes a device that can stimulate and record electrophysiological signals obtained from electrodes placed near a mixed nerve. The neural response can then be analysed to indicate the nature of the stimulated fibres. In an example, the electrophysiological response may indicate the presence or absence of specific nerve fibres. Based on the desired therapeutic outcome, this information is used to optimise the therapy. For example, various parameters for administering the therapy such as, but not limited to, stimulation waveform and lead position may be adjusted to recruit the desired fibre types. In some cases, several causes can be treated simultaneously, each requiring stimulation of a different subset of fibres (such as B fibres for incontinence and sensory fibres for pelvic pain, both located in the sacral nerve). In this case, the method and device will use electrophysiological measurements to continuously optimise the delivered stimulation regime, in order to elicit responses of the desired fibres while minimising the responses from unwanted fibres.

Figure 14:
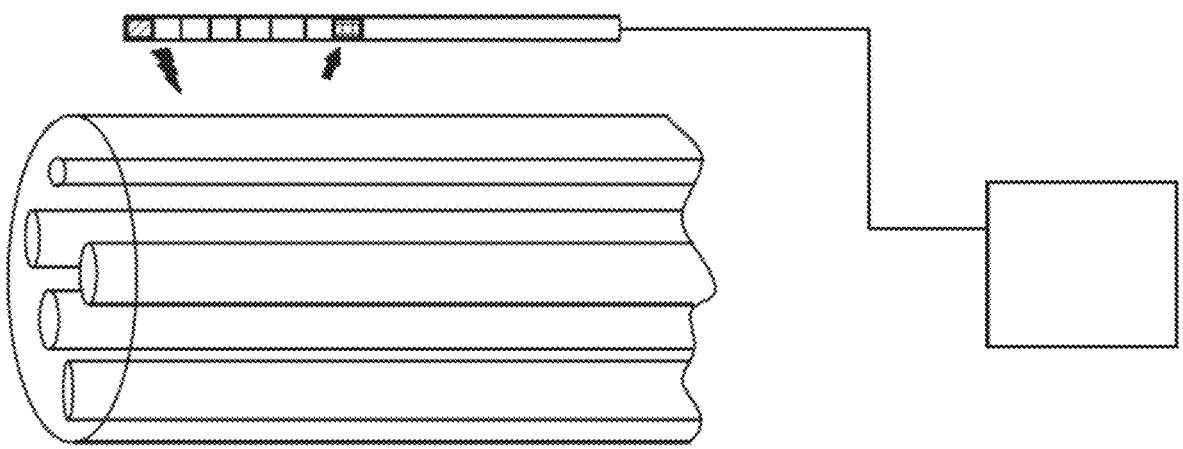
FIG. 14 illustrates an embodiment of the invention employing a single electrode lead for fibre type targeting.

In one embodiment, shown in FIG. 14, we propose a method consisting of 2 or more electrodes implanted near a target mixed nerve of which only a subset of fibres are desired stimulus targets, and an implantable control unit device capable of recording the electrophysiological response to the stimulation. The stimulated fibre populations are assessed via the recorded response and the electrode placement, the electrode selection, as well as the stimulus parameters (including, but not limited to, pulse width, stimulus frequency, stimulus waveform, stimulus amplitude) are optimised such that the desired fibre types are preferentially targeted. Additionally, the recorded responses can be used to optimise stimulus parameters in order to minimise power consumption. As long as the desired responses are observed, the parameters requiring the least power to achieve this should be used. In one SNS trial, B fibres were observed to be fully recruited at a stimulus amplitude which was only around a quarter of the amplitude being used as defined by reference to the past approach of the muscle activation threshold. This observation indicates that therapeutic benefits provided by B fibre recruitment could be achieved at a fraction of the power of current state of the art SNS techniques which operate blind to fibre type.

The characteristics of the neural response (evoked compound action potential, or ECAP) are used in order to assess which fibre types are activated by the stimulus paradigm. Without being limited by theory, the ECAP characteristics that can be used to assess the type of the stimulated fibres includes the conduction velocity (including latency), strength-duration characteristics, and the refractory period. Additionally, myoelectric responses (Late Responses (LRs)) can be used as a proxy measure for Aα efferent activation (either directly or indirectly) based on their presence and latency.

For example, in the case of sacral nerve stimulation, targeting parasympathetic fibres (lightly myelinated B type fibres), the electrodes are placed near the S3 sacral nerve as shown in FIG. 14. A first electrode is used for stimulation and neural recordings are obtained from 1 or more electrodes of the same array, close to the target nerve. The conduction velocity of the stimulated fibres is obtained from the neural recordings and the electrodes are placed such that the B fibres response is maximised and all other responses minimised. Further, the stimulation parameters are varied such that the B fibre responses are maximised and all other responses minimised.

Figure 13:
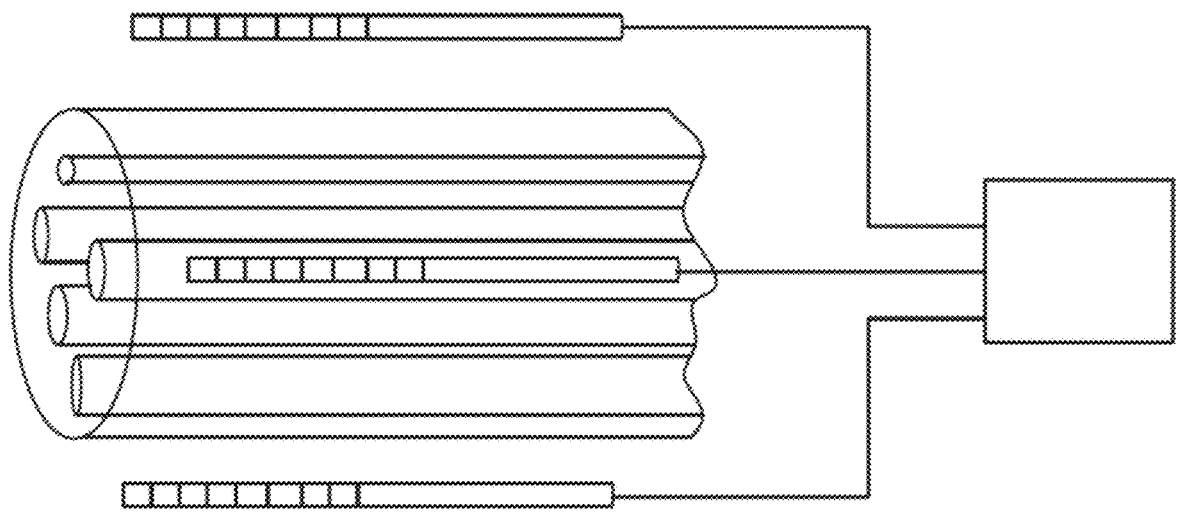
FIG. 13 illustrates an embodiment of the invention employing multiple electrode leads for fibre type targeting.
Figure 15:
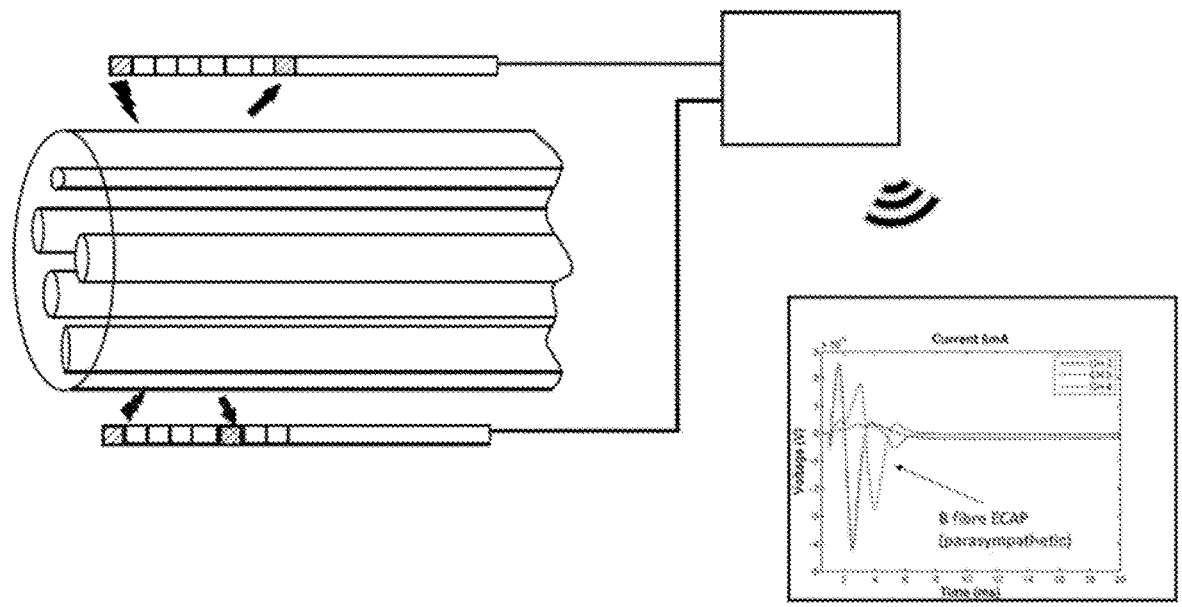
FIG. 15 illustrates another embodiment of the invention employing multiple electrode leads for fibre type targeting.

In other embodiments, such as those of FIGS. 13 and 15, a device is provided to optimise lead positioning and stimulus parameter selection for stimulation of a mixed nerve using a plurality of electrodes with different characteristics. This uses more than 1 lead placed near the target nerve. The selection of stimulus parameters is then carried out for more than 1 lead. In the case of a multitude of conditions, such as overactive bladder (OAB) as well as pelvic pain, electrode selection will be done so that either 1 or several electrodes on either one or several leads maximises the B fibre activation (for OAB relief) and the Aβfibre activation (for pain relief). Once again, it is to be noted that the present invention is not limited by theory of mechanism as the fibre type targeting may be performed in respect of any suitable fibre which achieves a therapeutic benefit irrespective of the theorised mechanism of action.

In other embodiments, the nerves of a plexus can be stimulated in turn to determine which branch of the plexus contains the desired fibres using recordings of evoked electrophysiological responses. The therapy is then optimised on the best candidate branch of the plexus.

Furthermore, the recording of ECAPs for a given stimulus electrode does not have to be done on the same lead. The recording site can be optimised (maximising signal amplitude) and any electrode close to the target nerve can be chosen. This is useful as the fascicles in mixed nerves do not run parallel inside the nerve (as is shown simply for illustrative simplicity in FIGS. 13 to 15, but cross, merge, and split as shown in FIG. 6.

Figure 16:
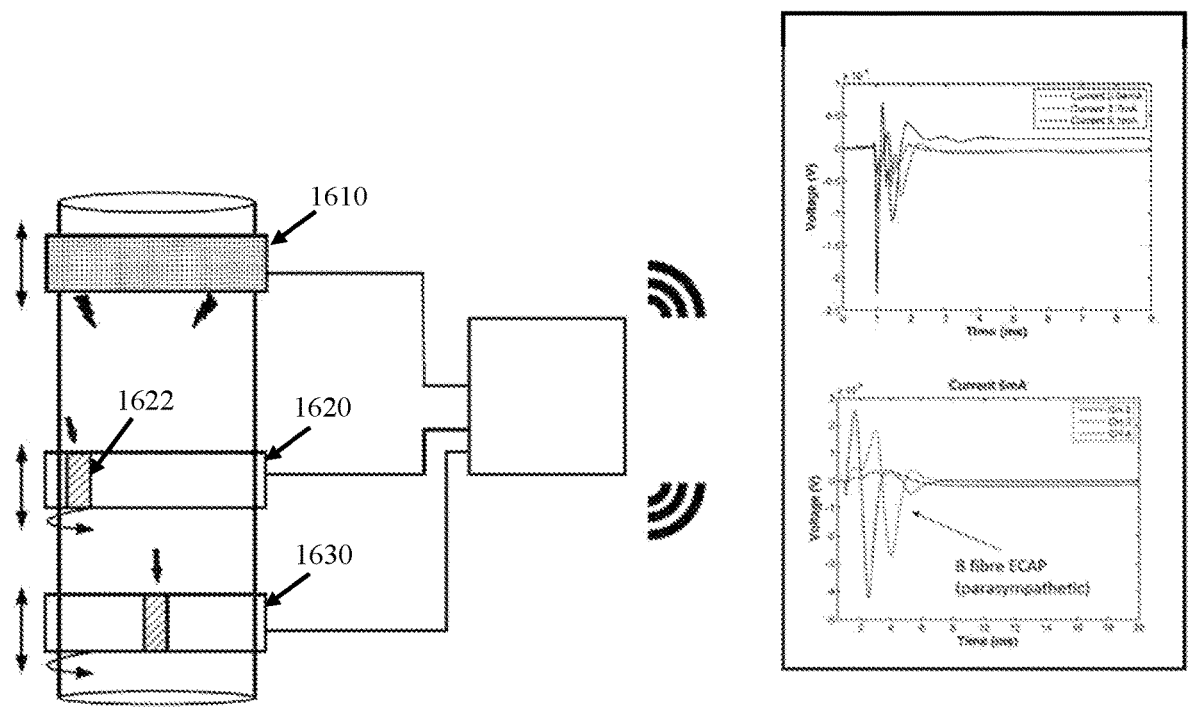
FIG. 16 illustrates an embodiment of the invention employing cuff electrodes for fibre type targeting.
Figure 17:
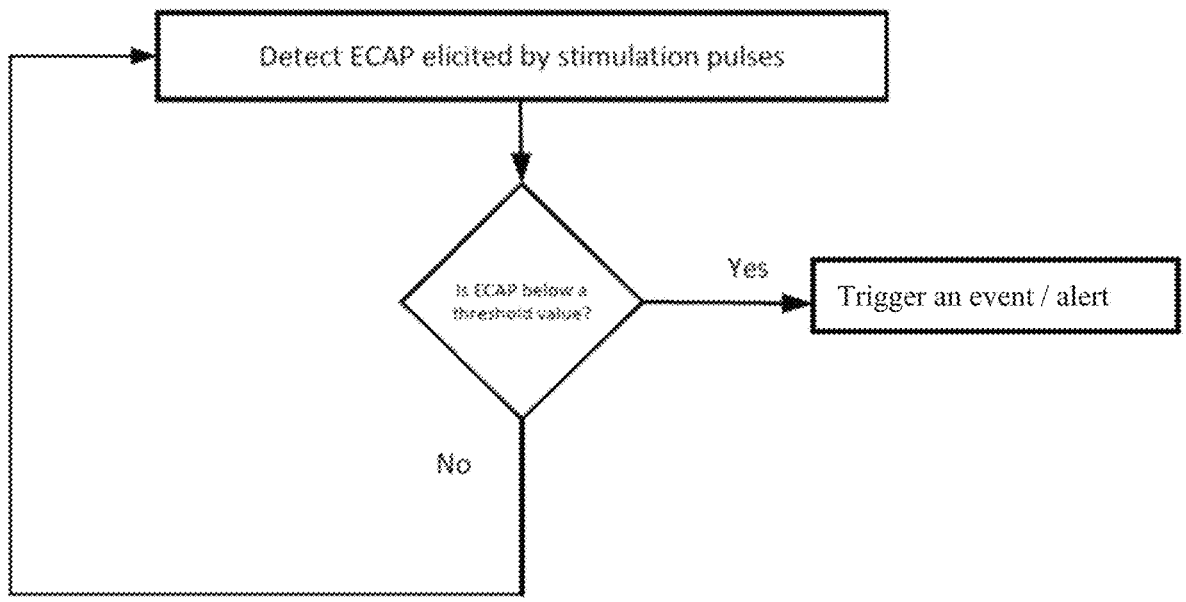
FIGS. 17 and 18 illustrate fibre type targeting flowcharts.
Figure 18:
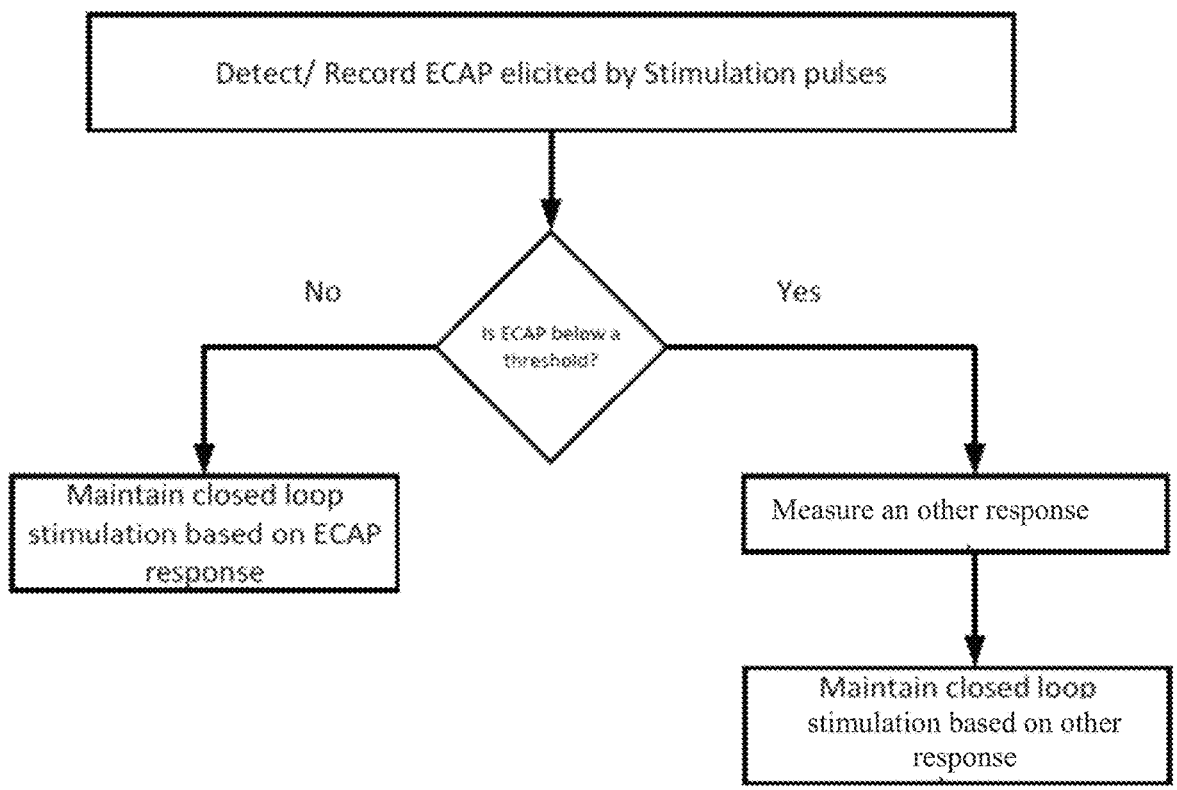

Another embodiment of this device will consist in implanting cuff electrodes instead of epidural leads, as shown in FIG. 16. The cuff electrodes will consist of several distinct contacts each (as opposed to some cuff electrodes that have one continuous electrode running along the entire cuff), and the 2 or more cuff electrodes can be rotated and moved up and down along the mixed nerve to find a position that optimises the discrete stimulation and recording of separate fascicles. In one embodiment the arrangement of FIG. 16 can be used for spatial targeting of a selected fibre type. This involves the cuff electrode 1610 applying a supramaximal stimulus around substantially an entire circumference of the nerve, in order to recruit all fibres of the nerve. Electrode 1610 may be a non-segmented electrode extending continuously around the nerve or may be a segmented electrode with the stimulus being applied simultaneously by all segments of the electrode 1610 to ensure all fibres are recruited. The recruited responses resulting from the stimulus can then be observed at selected circumferential positions by using a selected segment (e.g. segment 1622 of a segmented cuff electrode 1620 (other segments not shown for clarity). The response observed at segment 1622 in particular can then be analysed to determine a dominant fibre type which is adjacent to that segment 1622. This knowledge can then be used to identify which fibre type(s) are adjacent all segments of each segmented cuff electrode. In turn, this knowledge can be used to preferentially use a given segment, such as segment 1622, to deliver stimulation which will preferentially recruit the fibre type which is known to be adjacent to that segment. Other embodiments may derive the same knowledge by instead using segment 1622 to apply stimuli which are only just above a stimulus threshold and which therefore only recruit fibres proximal to segment 1622. The responses may then be observed at cuff electrode 1610 and analysed to determine the type of fibres being recruited by segment 1622 and thus the types of fibres which are adjacent to 1622. A survey may be carried out over multiple segments to thereby determine the fibre type(s)

adjacent to all such electrode segments, and spatial fibre type targeting may then be applied by using such knowledge as a lookup table.

Additionally, the responses can be used to optimise stimulus parameters in order to minimise power consumption. As long as the desired responses are observed, the parameters requiring the least power to achieve this should be used.

More generically, different lead shapes can be used, paddle leads, percutaneous leads, cuff electrodes, while effecting fibre type targeting in accordance with the present invention.

In some embodiments, the device is connected externally to the electrodes, in other embodiments, the device is fully implantable. In some embodiments, the electrodes can be on a single lead, or multiple leads placed in proximity to the stimulus target, each lead can contain a multitude of electrodes. In other embodiments, some electrodes can be located distally to the target nerve to serve as reference electrode for the measurement or return electrode for the stimulation. In the case where the device is a fully implantable system, the body of the implant can be used as one electrode.

In some embodiments, the leads can be epidural, similar to those used in sacral nerve stimulation or spinal cord stimulation. In other embodiments, the leads can be paddle leads, or cuff electrodes. In some embodiments, the electrodes can further be segmented. In one example, a cuff electrode can in some cases be a ring electrode surrounding the nerve, and in some cases it can be a segmented ring whereby electrically distinct portions of the cuff electrode take distinct positions around the circumference of the nerve, allowing distinct circumferential positions around the nerve to be selectively targeted by stimulating from a selected segment or to be selectively observed by recording from a selected segment. In one example, an epidural lead can have circular electrode contacts, in other examples the contacts can be segmented.

In some embodiments, the stimulation and recording are performed on the same electrodes, in other embodiments the stimulation and recording are done on distinct electrodes whether on the same electrode lead or electrode array, or a different electrode lead or array. In some embodiments, some electrodes implanted near the target span an area small enough to avoid merging or branching of fibre tracts within the nerve. For example, in some embodiments, electrodes implanted near the sacral nerve can span a distance of less than 5 centimetres, preferably less than 2 centimetres.

In some embodiments, the external device may be used to analyse neural response during lead insertion. The external device may be used to deliver stimulation pulses to a target nerve in a patient. The external device may include a control unit, a display module and a stimulation module. The stimulation unit is configured to deliver stimulation pulses to a desired nerve and analyse the neural response generated. Thereafter, the control unit is adapted to analyse the neural response and differentiate the recruited nerves based on one or more parameters. The control unit is configured to transmit information to display the neural recruitment in one or more modes. In a first mode, the neural recruitment is displayed in the form of a collection of ECAP waveforms and myoelectric waveforms. In a second mode, the neural recruitment is displayed as waveforms which are labelled with the corresponding fibre types. In a third mode, the neural recruitment is displayed as waveforms with timing partitions to indicate the fibre types which were recruited. In a fourth mode, the neural recruitment is displayed along with characteristics of the fibres such as conduction velocity etc.

In some embodiments, the external device is adapted to operate one or more electrodes. The external device is adapted to deliver pulses via paddle leads, cylindrical leads and cuff electrodes. Further, the external device is configured to operate in any combination of the aforementioned electrodes.

Implantable device: In some embodiments, the implantable device is configured to perform all the functions as the external device except that it is implanted within the body of the patient.

In some embodiments, the electrophysiological responses elicited by the stimulation can be displayed in real time. In some embodiments, these responses can further be processed to increase the signal to noise ratio. For example, averaging can be used to decrease the random noise found on each individual response, and fit-and-remove algorithms can be used to decrease the artefact component in the signal. These signals can be used to recognise the activation of a certain fibre type or certain fibre types. The stimulus parameters can then be modified whether by trial and error, brute force exploration or any suitable search technique of the stimulus parameter space, so as to optimise fibre activation of the desired subsets of fibres as indicated by the displayed responses.

In some embodiments, the axes of the electrophysiological response graph can be labelled to facilitate the interpretation of the responses. For example, based on the stimulus and recording electrode configurations, the axes of the response graph can be labelled to indicate the times at which the response of a given fibre type should be recorded if present.

In some embodiments, the neural responses can be marked and/or labelled to help identify the fibre types being recruited by the stimulation. For example, the peaks of the response can be labelled with their time and amplitude parameters.

In some embodiments, a change in morphology of the response with varying stimulus parameters can be used to identify fibre type contributions in an ECAP in which the peaks are poorly defined. In one example, the current is slowly ramped up and the ECAP shape observed or automatically processed. Initially, the largest fibres will respond to external stimuli first, a change in ECAP morphology at higher amplitudes could indicate the recruitment of a second, slower fibre type. In another example, the frequency of the stimulation can be increased to an appropriate level, and the responses observed over time. The small fibres will fatigue first, the larger fibres last. The change in morphology over time can be used to determine which part of the ECAP is associated with which fibre type. Further, a decrease in amplitude of the myoelectric response at increasing stimulus frequency could be due to muscle fatigue, or depression of the H-reflex. These properties and others can be used to determine the fibre types being stimulated.

In some embodiments, processing can be done on the recorded neural responses to display an estimate of the conduction velocity of the different elements of the recording of the electrophysiological response.

In some embodiments, the recording(s) of the electrophysiological response can be processed such that an estimate of the number of fibres of each type being recruited is displayed. The estimate could in some instances give a proportion of fibre types or an absolute estimate of the number of fibres being activated.

In some embodiments, stimulation can be performed in a way to approach a constant neural recruitment by adapting the stimulus parameters automatically in a feedback arrangement in order to approach a target electrophysiological response. In one example, B fibres are preferentially targeted in a mixed nerve. After selecting the stimulus electrodes and parameters that optimise B fibre recruitment, the current (or another parameter) could be automatically adjusted to maintain a constant response amplitude. In another example, the late response can be used as a proxy measure for motor fibre activation, the stimulus can then be automatically adjusted to maintain a constant late response amplitude.

The amplitude of the electrophysiological response or a part of it could be done by assessing peak amplitudes, peak-peak amplitudes, the area under the curve, a convolution with a filter, or any other method.

In some embodiments, an implantable device may be configured to establish closed-loop stimulation on a targeted fibre type. For instance, the feedback loop may be established on the neural response of the B fibres in a mixed nerve. The methods disclosed herein enable the implantable device to establish a feedback loop on the neural response of certain fibre types. Since the implantable device is configured to determine the fibre types based on the neural response, the implantable device can maintain closed loop stimulation based on the response of the targeted fibre type. The implantable device may maintain closed-loop stimulation on at least one or more of the fibre types which include, but not limited to, A$\alpha$, A$\beta$, A$\delta$, B and C fibres. In some cases, closed-loop stimulation may be maintained on the myoelectric response elicited by the stimulation. If the desired response is not observable, another response can be used as a proxy measure for establishing and maintaining closed-loop stimulation.

In some embodiments, the neural recruitment can be automatically monitored for large variations that could be indicative of, for example, lead migration. In one example, a change in electrode position that would lead to loss of efficacy could be tested by the device by varying the current amplitude to a small degree and monitoring the response profile. If no change is observed with variations in stimulus amplitude, a warning signal is sent to the user, or stimulation is stopped or other suitable action occurs.

In some further embodiments, the implantable device may be configured to check the fibre types which are recruited by the stimulation pulses. This feature may be used to ensure that the desired fibre types are recruited for the majority of the stimulus duration. In some cases, when the implantable device fails to detect the response of a fibre type for a duration which exceeds a threshold, the implantable device may trigger an alert to the patient that the desired fibre type is no longer recruited. In such a case, the physician may consider the possible causes and take remedial action. In other embodiments, alternative actions may be triggered in such an event, such as automatic reconfiguration of the stimulus paradigm. Such functions may alternatively be carried out by an external device such as a clinician's programmer device.

In some embodiments, continuous monitoring can be used to both maintain a near constant neural recruitment, as well as to warn of a substantial change in lead placement or nerve properties. Further embodiments may provide for testing the feedback loop integrity before applying the next corrective stim pulse. This could be done by making sure that if the current is increased, the response also increases. This would keep the loop from diverging when the signal is lost (as can occur when the signal is lost when changing posture, or when the charger or another interfering source is applied).

In some embodiments, the method and device may be applied to vagus nerve stimulation, dorsal root stimulation, sacral nerve stimulation, or ventral root stimulation. In some embodiments, the method and device can be used in more than one location, simultaneously or in tandem. For example, the device could be used in the sacral nerve and the lower thoracic or upper lumbar ventral roots which innervate the bladder and bowel. Without being limited by theory, it is proposed that such a device can stimulate both the sympathetic and parasympathetic nervous system in locations specific for bladder and bowel control. Stimulating the ventral roots of the spinal cord and/or the vagus nerve, and/or the sacral nerve can lead to similar embodiments in which the target is different from the bladder and bowel, such as any one or more of the heart, larynx, trachea, bronchi, oesophagus, stomach, liver, pancreas, small intestine, spleen, large intestine, kidney or sexual organs. For example, sympathetic and parasympathetic stimulation of the liver could be achieved by stimulating the sympathetic fibres in the thoracic sections T5-T12 and the parasympathetic fibres originating in the vagus nerve. Vagus nerve stimulation may be improved by some embodiments of the present invention may selectively avoiding stimulation of fibre types which in past solutions cause fatigue of the throat, swallowing muscles, vocal chords, and the like, which in past solutions are unnecessarily recruited. Note also partial lesions of the spinal cord might be best healed by targeting specific fibres.

In other embodiments the programming and display module does not have to be part of the implanted device. In such embodiments the implanted stimulator itself only executes the program that was set by the control module, and the responses are observed in real time or later only on an external programmer, and not on the implanted device.

The preceding thus reveals large inter-patient variability in fibre type recruitment and significant posture-related effects on the number of fibres recruited. Further, there was a clear distinction between fibre type recruited and trial outcome. These first-in-human results show that recordings of an electrophysiological response can be used to identify the type of fibres recruited by SNS therapy and that the type of fibre may correlate with therapeutic effectiveness. These results pave the way for improved targeting as well as closed-loop SNS that has the potential to greatly improve the therapy.

Notably, the fibre targeting of the present invention allowed some subjects to achieve effective therapy at stimulation levels which were orders of magnitude less than a muscle response threshold or sensory response threshold which would conventionally have been used to set a stimulation level. This would lead to a many multiples increase in battery lifetime.

Embodiments undertaking fibre type targeting on an ongoing basis to control a feedback process have the further advantage of being responsive to lead movement relative to the nerve, as occurs with posture changes, coughs, sneezes and the like. In contrast to conventional approaches which fix the stimulation at a single high level, the use of feedback based on electrophysiological measurements allows stimulation to be constantly revised to ensure that the desired fibre type continues to be recruited by suitably refining the stimulation parameters on an ongoing basis. Similar benefits can be obtained even in simpler embodiments which simply detect a loss of recruitment of the desired fibre type and issue an alert to the user to, for example, seek clinical assistance. Alternatively, automatic modification of the stimulus paradigm could be performed in some embodiments in the event in which the determined stimulus paradigm fails to recruit the desired fibre types.

It is to be understood that the fibres types named in the examples are based on current understanding and should not be considered limiting in the application of the present invention.

The described electronic functionality can be implemented by discrete components mounted on a printed circuit board, and/or by a combination of integrated circuits, and/or by an application-specific integrated circuit (ASIC).

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not limiting or restrictive.

The invention claimed is:

1. A method of neurostimulation of a mixed nerve comprising a plurality of nerve fibre types, the method comprising:
   positioning an implantable electrode array proximal to a mixed nerve comprising a plurality of nerve fibre types, the implantable electrode array comprising a plurality of electrodes;
   delivering an electrical stimulus from at least one nominal stimulus electrode of the implantable electrode array, the electrical stimulus being delivered in accordance with a set of stimulus parameters;
   obtaining from at least one nominal recording electrode of the implantable electrode array a recording of an electrophysiological response evoked by the electrical stimulus;
   analysing the recording of the electrophysiological response by assessing one or more selected characteristics of the recording, and identifying from the assessed selected characteristics a level of recruitment of a first fibre type recruited by the electrical stimulus; and
   refining the stimulus parameters in a manner to effect selective recruitment of first fibre types relative to other fibre types of the mixed nerve,
   wherein the stimulus parameters are post-operatively refinable stimulus parameters.

2. The method of claim 1 wherein the stimulus parameters are refined in a manner to effect selective recruitment of the first fibre type while further effecting selective non-recruitment or diminished recruitment of at least one other fibre type.

3. The method of claim 1 wherein the stimulus parameters which are refined to effect selective recruitment of the first fibre type comprise one or more of: stimulus frequency; stimulus amplitude; stimulus waveform; stimulus pulse width; stimulus electrode(s) selection, stimulus phase; and stimulus polarity.

4. The method of claim 1 wherein the one or more selected characteristics of the recording from which the level of recruitment by the electrical stimulus of the first fibre type is identified comprise one or more of: one or more electrophysiological response inflexion points; one or more electrophysiological response peak positions; one or more electrophysiological response peak amplitudes; electrophysiological response propagation velocity; propagation or non-propagation of the electrophysiological response; electrophysiological response duration; refractory period; strength-duration curve characteristics including chronaxie or rheobase; growth curve characteristics including threshold and slope; number of electrophysiological response peaks with increasing stimulus current; presence, amplitude and/or latency of a late response, response properties of the electrophysiological response to varying stimulus frequencies, zero crossings of the electrophysiological response, a width of lobes of the electrophysiological response.

5. The method of claim 1 wherein the selected characteristic is conduction velocity, and the fibre type recruited is determined from a relationship between the diameter of a myelinated fibre and the conduction velocity.

6. The method of claim 1, where the selected characteristic is conduction velocity, and the conduction velocity is measured by determining a propagation time from the stimulus site to a single measurement electrode a known distance from the stimulus site.

7. The method of claim 1 where the selected characteristic is conduction velocity, and wherein the conduction velocity is measured by observing a neural response at a first measurement electrode and at a second measurement electrode, and determining a propagation time between the first and second measurement electrodes.

8. The method of claim 1 wherein the selected characteristic is determined by analysis of recordings of the electrophysiological response obtained from two or more spaced apart measurement electrodes, observing a single electrophysiological response.

9. The method of claim 1 comprising delivering therapy on the basis of recruitment of fibres unrelated to muscle activation.

10. The method of claim 1 wherein the selected characteristic includes a non-propagating characteristic of the recording, arising from activation of motor fibres causing far field muscle activation.

11. The method of claim 1 wherein the selected characteristic is taken to indicate activation of A$\alpha$ fibres or Ia fibres and comprises at least one of: a response arising less than 1 ms after the stimulus, and a response having a conduction velocity in the range 80-120 m/s.

12. The method of claim 1 wherein the selected characteristic is taken to indicate activation of B fibres and comprises at least one of: a response arising less than 6 ms after the stimulus, and a response having a conduction velocity in the range 3-15 m/s.

13. The method of claim 1 wherein the selected characteristic is taken to indicate activation of C fibres and comprises at least one of: a response arising less than 6 ms after the stimulus; a response having a conduction velocity in the range 0.5-2 m/s; and a response having a duration of over 10 ms.

14. The method of claim 1 wherein the selected characteristic is taken to indicate activation of A$\beta$ fibres and comprises at least one of: a response arising within 3 ms after the stimulus; and a response having a conduction velocity in the range 30-80 m/s.

15. The method of claim 1 wherein more than one selected characteristic of the recording of the electrophysiological response is assessed in order to determine a level of recruitment of each of two or more fibre types recruited by the electrical stimulus.

16. The method of claim 15 wherein the two or more fibre types are targeted for the purpose of treating a single condition.

17. The method of claim 15 wherein the two or more fibre types are targeted for the purpose of treating two or more co-existing or comorbid conditions.

18. The method of claim 1 wherein a machine learning classifier is applied in order to classify assessed neural responses by fibre type(s) present.

19. The method of claim 1 wherein the at least one nominal recording electrode, and the at least one nominal stimulus electrode, are positioned adjacent to a single branch of the mixed nerve, being a segment of the mixed nerve in which no neural branching or neural merging occurs upon the nerve between the nominal recording electrode(s) and the nominal stimulus electrode(s).

20. The method of claim 1 wherein the nominal recording electrode(s) and the nominal stimulus electrode(s) are positioned less than 60 mm apart.

21. The method of claim 20 wherein the nominal recording electrode(s) and the nominal stimulus electrode(s) are positioned less than 30 mm apart.

22. The method of claim 21 wherein the nominal recording electrode(s) and the nominal stimulus electrode(s) are positioned less than 20 mm apart.

23. The method of claim 1 wherein the mixed nerve comprises at least two fibre types comprising two or more of $A\alpha$, $A\beta$, $A\delta$, $A\gamma$, B and C fibre types, or other naming system fibre types.

24. The method of claim 1 wherein the mixed nerve comprises a vagus nerve.

25. The method of claim 24 wherein the first fibre type comprises parasympathetic fibres to provide a therapy for one or more of a brain related condition such as refractory epilepsy or depression or serve a therapeutic effect in the periphery or viscera.

26. The method of claim 25 providing a therapy for a heart, larynx, trachea, bronchi, oesophagus, stomach, liver, pancreas, small intestine, spleen, large intestine or kidney.

27. The method of claim 1 wherein the mixed nerve comprises a sacral nerve.

28. The method of claim 27 to provide a therapy for one or more of fecal incontinence (FI), Urinary Retention (UR), Urinary Urge Incontinence (UUI), intractable constipation, and chronic pelvic pain.

29. The method of claim 1 wherein the mixed nerve comprises a root of a spinal nerve.

30. The method of claim 29 wherein the first fibre type comprises parasympathetic fibres to provide a therapy for any one or more of the large intestine, bladder, and genitalia.

31. The method of claim 29 wherein the first fibre type comprises sympathetic fibres to provide a therapy for the heart and/or larynx by stimulating the sympathetic fibres in one or more of the ventral roots of thoracic segments T1-T4.

32. The method of claim 29 wherein the first fibre type comprises sympathetic fibres to provide a therapy for the stomach, liver, pancreas, adrenal gland, spleen, and/or small intestine by stimulating the sympathetic fibres in one or more of the ventral roots of thoracic segments T5-T12.

33. The method of claim 29 wherein the first fibre type comprises sympathetic fibres to provide a therapy for the kidney, bladder, genitalia, and/or lower intestine by stimulating the sympathetic fibres in one or more of the ventral roots of thoracic segment T12 and the lumbar segments L1-L3.

34. The method of claim 1, comprising spatially targeting the first fibre type by applying a supramaximal stimulus from a first electrode to recruit all fibres of the nerve, observing the recruited responses at selected circumferential positions by using a selected electrode segment for recording at the selected circumferential position, analysing the recorded response to determine one or more fibre types which are adjacent to that position, and subsequently applying stimuli from the selected electrode segment at times when it is desired to recruit the first fibre type among the one or more fibre types so identified.

35. The method of claim 1, comprising spatially targeting the selected fibre type by using a selected electrode segment at a selected circumferential position to apply stimuli which are only just above a stimulus threshold to recruit fibres proximal to that segment, observing recruited responses at a second electrode, and analysing the recordings to determine the type of fibres being recruited by the stimuli from the selected electrode segment.

36. A non-transitory computer readable medium for neurostimulation of a mixed nerve comprising a plurality of nerve fibre types, comprising instructions which, when executed by one or more processors, causes performance of the following:
delivering an electrical stimulus from at least one nominal stimulus electrode of an implantable electrode array proximal to a mixed nerve comprising a plurality of nerve fibre types, the implantable electrode array comprising a plurality of electrodes, the electrical stimulus being delivered in accordance with a set of stimulus parameters;
obtaining from at least one nominal recording electrode of the implantable electrode array a recording of the electrophysiological response evoked by the electrical stimulus;
analysing the recording of the electrophysiological response by assessing one or more selected characteristics of the recording, and identifying from the assessed selected characteristics the levels of recruitment of the fibre types recruited by the electrical stimulus; and
post-operatively refining the stimulus parameters in a manner to effect selective recruitment of a first fibre type relative to other fibre types of the mixed nerve.

37. A neurostimulation device comprising:
an implantable electrode array configured to be implanted proximal to a mixed nerve comprising a plurality of nerve fibre types, the implantable electrode array comprising a plurality of electrodes; and
a control unit configured to deliver an electrical stimulus from at least one nominal stimulus electrode of the implantable electrode array, the electrical stimulus being delivered in accordance with a set of stimulus parameters; the control unit further configured to obtain from at least one nominal recording electrode of the implantable electrode array a recording of an electrophysiological response evoked by the electrical stimulus; the control unit further configured to analyse the recording by assessing one or more selected characteristics of the recording, and identify from the assessed selected characteristics a level of recruitment of at least a first fibre type recruited by the electrical stimulus, and the control unit further configured to post-operatively refine the stimulus parameters in a manner to effect selective recruitment of the first fibre types relative to other fibre types of the mixed nerve.

* * * * *